United States Patent [19]

Daly et al.

[11] Patent Number: 5,789,539

[45] Date of Patent: Aug. 4, 1998

[54] CHEMOKINE-LIKE PROTEINS AND METHODS OF USE

[75] Inventors: Thomas J. Daly, Framingham; Gregory J. LaRosa, Boston, both of Mass.

[73] Assignee: Repligen Corporation, Cambridge, Mass.

[21] Appl. No.: 482,111

[22] Filed: Jun. 7, 1995

Related U.S. Application Data

[63] Continuation-in-part of Ser. No. 330,163, Oct. 26, 1994.

[51] Int. Cl.$^6$ .................. C07K 14/54; A61K 38/20; C12N 15/24

[52] U.S. Cl. ............. 530/324; 424/85.2; 435/69.52; 435/70.1; 435/71.1; 435/172.3; 514/2; 514/12; 514/885

[58] Field of Search ................ 530/324; 424/85.2; 435/69.52, 70.1, 71.1, 71.2, 172.3, 252.3, 320.1; 514/2, 12, 885

[56] References Cited

U.S. PATENT DOCUMENTS

| | | | |
|---|---|---|---|
| 5,149,544 | 9/1992 | Gentile et al. | 424/577 |
| 5,185,323 | 2/1993 | Gewirtz | 514/12 |
| 5,294,544 | 3/1994 | Gentile et al. | 435/70.4 |

FOREIGN PATENT DOCUMENTS

| | | |
|---|---|---|
| PCT/US95/13897 | of 0000 | WIPO . |
| WO 93/11159 | 6/1993 | WIPO . |
| WO 94/13321 | 6/1994 | WIPO . |

OTHER PUBLICATIONS

Beall et al., "Conversion of Monocyte Chemoattractant Protein–1 into a Neutrophil Attractant by Substitution of Two Amino Acids", *J. Biol. Chem.*, 267 :3455–3459 (1992).

Broxmeyer et al., "Enhancing and Suppressing Effects of Recombinant Murine Macrophage Inflammatory Proteins on Colony Formation In Vitro by Bone Marrow Myeloid Progenitor Cells", *Blood*, 76 :1110–1116 (1990).

Broxmeyer et al., Macrophage Inflammatory Protein (MIP)–1β Abrogates the Capacity of 1α To Suppress Myeloid Progenitor Cell Growth:, *J. Immunol.*, 147 :2586–2594 (1991).

Broxmeyer et al., "Comparative Analysis of the Human Macrophage Inflammatory Protein Family of Cytokines (Chemokines) on Proliferation of Hyman Myeloid Progenitor Cells", *J. Immunol.*, 150 :3448–3458 (1993).

Clark–Lewis et al., "Platelet factor 4 binds to interlukin 8 receptors and activates neutrophils when its N terminus is modified with Glu–Leu–Arg", *Proc. Natl. Acad. Sci. USA*, 90 :3574–3577 (1993).

Cooper et al., "Myelosuppressive effects in vivo with very low dosages of monomeric recombinant murine macrophage inflammatory protein–1α", *Experimental Hematology*, 22 :186–193 (1994).

Dunlop et al., "Demonstration of Stem Cell Inhibition and Myeloprotective Effects of SCI/rhMIP1α In Vivo", *Blood*, 79 :2221–2225 (1992).

Graham et al., "Identification and Characterization of an Inhibitor of Haemopoietic Stem Cell Proliferation" *Nature*, 344:442–444 (1990).

Gewirtz et al., "Inhibition of Human Megakaryocytopoiesis In Vitro by Platelet Factor 4 (PF4) and a Synthetic COOH–Terminal PF4 Peptide", *J. Clin. Invest.* 83 :1477–1486 (1989).

Han et al., "Platelet Factor 4 Inhibits Human Megakaryocytopoiesis In Vitro", *Blood*, 75 :1234–1239 (1990).

Hebert et al., "Scanning Mutagenesis of Interleukin–8 Identifies a Cluster of Residues Required for Receptor Binding", *J. Biol. Chem.*, 266 :18989–18994 (1991).

Lord et al., "Macrophage–Inflammatory Protein Protects Multipotent Hematopoietic Cells from the Cytotoxic Effects of Hydroxyurea In Vivo", *Blood*, 79 :2605–2609 (1992).

Mantel et al., "Polymerization of murine macrophage inflammatory protein 1α inactivates its myelosuppressive effects in vitro: The active form is a monomer", *Proc. Natl. Acad. Sci. USA*, 90 :2232–2236 (1993).

Maze et al., "Myelosuppressive Effects In Vivo of Purified Recombinant Murine Macrophage Inflammatory Protein–1α", *J. Immunol.* 149 :1004–1009 (1992).

Moser et al., Interleukin–8 Antagonists Generated by N–terminal Modification,: *J. Biol. Chem.*, 268 :7125–7128 (1993).

Oppenheim et al., "Properties of the Novel Proinflammatory Supergene 'Intercrine' Cytokine Family", *Ann. Rev. Immunol.*, 9 :617–648 (1991).

Rajarathram et al., "Neutrophil Activation of Monomeric Interleukin–8", *Science*, 264 :90–90 (1994).

Tekamp–Olson et al., "Cloning and Characterization of cDNAs for Murine Macrophage Inflammatory Protein 2 and its Human Homologues", *J. Exp. Med.*, 172:911–919 (1990).

Wolpe et al., "Macrophage infimmatory proteins 1 and 2: members of a novel superfamily of cytokines", FASEB, 3:2565–2573 (1989).

Bidlingmeyer et al., "Rapid Analysis of Amino Acids Using Pre–Column Derivatization" *J. Chrom.*, 336 :93–104 (1984).

Smith et al., "Measurement of Protein Using Bicinchoninic Acid", *Anal. Biochemistry*, 150 :76–85 (1985).

(List continued on next page.)

*Primary Examiner*—John Ulm
*Assistant Examiner*—Prema Mertz
*Attorney, Agent, or Firm*—Fish & Richardson P.C.

[57] ABSTRACT

The invention relates to novel chemokine-like proteins that include two or more newly discovered active domains from different chemokines. Active domains are regions of several contiguous amino acids that are necessary for chemokines' ability to suppress the proliferation of actively dividing myeloid cells, e.g., myeloid progenitor cells, myeloid stem cells, and leukemic cells. The new chemokine-like proteins provide higher myelosuppressive activity than naturally occurring, wild-type chemokines.

19 Claims, 24 Drawing Sheets

OTHER PUBLICATIONS

Poncz et al., "Cloning and Characterization of Platelet Factor 4 cDNA Derived from a Human Erythroleukemic Cell Line", *Blood*, 69:219–223 (1987).

Hebert et al., "Endothelial and Leukocyte Forms of IL-8; Conversion by Thrombin and Interactions with Neutrophils", *J. Immunol.*, 145:3033–3040 (1990).

Clark-Lewis et al., "Chemical Synthesis, Purification, and Characterization of Two Inflammatory Proteins, Neutrophil Activating Peptide 1 (Interleukin-8) and Neutrophil Activating Peptide 2", *Biochemistry 30*:3128–3135 (1991).

Thomas et al., "The Interleukin-8 Receptor is Encoded by a Neutrophil-specific cDNA clone, F3R", *J. Biol. Chem.*, 266:14839–14841 (1991).

LaRosa et al., "Amino Terminus of the Interleukin-8 Receptor is a Major Determinant of Receptor Subtype Specificity", *J. Biol. Chem.*, 267:25402–25406 (1992).

Caen et al., "Platelet Factor 4 (PF4) and a Dodecapeptide Related to PF4 Protect Hematopoietic Precursor Cells from Chemotherapy", *Blood*, 82:162a, Abstract No. 635 (1993).

Hecht, *Drug and Market Development*, 4 (3):49 (1993).

Johnson et al., "Cloning of Two Rabbit GRO Homologues and Their Expression in Alveolar Macrophages", *Gene*, 151:337–338, (1994).

Power et al., "Cloning of a Full-Length cDNA Encoding the Neutrophil-activating Peptide ENA-78 from Human Platelets", *Gene*, 151:333–334, (1994).

```
IL-8mono  SAKELRCQCIKTYSKPFHPKFIKELRVIESGPHCANTEIIVKL.SDGRELCLDPKENWVQRVVEKFLKRAENS  (SEQ ID NO:1)
Groα      ASVATELRCQCLQTLQ.GIHPKNIQSVNVKSPGPHCAQTEVIATL.KNGRKACLNPASPIVKKIIEKMLNSDKSN  (SEQ ID NO:2)
Groβ      APLATELRCQCLQTLQ.GIHLKNIQSVNVKSPGPHCAQTEVIATL.KNGQKACLNPASPMVKKIIEKMEKNGKSN  (SEQ ID NO:3)
Groγ      ASVVTELRCQCLQTLQ.GIHLKNIQSVNVRSPGPHCAQTEVIATL.KNGKKACLNPASPMVQKIIEKILNKGSTN  (SEQ ID NO:4)
NAP2      AELRCHCIKTTS.GIHPKNIQSLEVIGKGTHCNQVEVIATL.KDGRKICLDPDAPRIKKIVQKKLAGDESAD    (SEQ ID NO:5)
PF4       EAEEDGDLQCLCVKTTS.QVRPRHITSLEVIKAGPHCPTAQLIATL.KNGRKICIDLQAPLYKKIIKKLLES    (SEQ ID NO:6)
LIP10     VPLSRTVRCTCISNQPVNPRSLEKLEIIPASQFCPRVEIIATMKKKGEKRCLNPESKAIKNLLKAVSKEMSKRSP (SEQ ID NO:7)
ENA 78    AGPAAAVLRELRCVCLQTTQ.GVHPKMISNLQVFAIGPQCSKVEVVASL.KNGKEICLDPEAPFLKKVIQKILDGGNKEN (SEQ ID NO:8)
βTG       GKEESLDSDLYAELRCMCIKTTS.GIHPKNIQSLEVIGKGTHCNQVEVIATL.KDGRKICLDPDAPRIKKIVQKKLAGDESA  (SEQ ID NO:9)
CTAP-III  NLAKGKEESLDSDLYAELRCMCIKTTS.GIHPKNIQSLEVIGKGTHCNQVEVIATL.KDGRKICLDPDAPRIKKIVQKKLAGDESAD (SEQ ID NO:10)
PBP       SSTKGQTKRNLAKGKEESLDSDLYAELRCMCIKTTS.GIHPKNIQSLEVIGKGTHCNQVEVIATL.KDGRKICLDPDAPRIKKIVQKKLAGDESAD
                                                                                         (SEQ ID NO:11)
MCP-1     .HMQPDAINAPVTCCYNF.TNRKISVQRLASYRRITSSKCPK.EAVI..FKTIVAKEICADPKQKWVQDSM.DHLDKQTQTPKT  (SEQ ID NO:12)
MIP-1α    FSASLAADTPTACCFSY.TSRQIPQNFIADYF.ETSSQCSKP.GVI..FLTKRSRQVCADPSEEWVQKYVSDLELSA  (SEQ ID NO:13)
RANTES    PYSSDTTPCCFAY.IARPLDRAHIKEYF.YTSGKCSNP.AVV..FVTRKNRQVCANPEKKWYREYINSLEM  (SEQ ID NO:14)
MIP-1β    GSDPPTACCFSY.TARKLPRNFVVDYY.ETSSLCSQP.AVV..FQTKRSKQVCADPSESWVQEYVYDLEL  (SEQ ID NO:15)
```

FIG. 1

```
IL-8   SAKELRCQCIKTYSKPFHPKFIKELRVIESGPHCANTEIIVKLSDGRELCLDPKENWVQRVVEKFLKRAENS   (SEQ ID NO:1)
M1     SAKDLQCQCIKTYSKPFHPKFIKELRVIESGPHCANTEIIVKLSDGRELCLDPKENWVQRVVEKFLKRAENS   (SEQ ID NO:16)
M3     SAKELRCQCIKTYSKPFHPKFIKEYRIESGPHCANTEIIVKLSDGRELCLDPKENWVQRVVEKFLKRAENS    (SEQ ID NO:17)
M4     SAKELRCQCIKTYSKPFHPKFIKELERVIESGPHCANTEIIVKLSDGRELCLDPKENWVQRVVEKFLKRAENS  (SEQ ID NO:18)
M6     SAKELRCQCIKTYSKPFHPKFIKELRAIESGPHCANTEIIVKLSDGRELCLDPKENWVQRVVEKFLKRAENS   (SEQ ID NO:19)
M7     SAKELRCQCIKTYSKPFHPKFIKELRVIESGPHCANTEIIVKLSDGRELCLDQAPLYKKIIKKLLES        (SEQ ID NO:20)
M8     SAKELQCQCIKTYSKPFHPKFIKELRVIESGPHCANTEIIVKLSDGRELCLDPKENWVQRVVEKFLKRAENS   (SEQ ID NO:47)
M9     SAKELRCQCIKTYSKPFHPKFIKELRVIESGPHCANTEIIVKLSDGRELCLDPKENWVQRVVEKFLKRAENS   (SEQ ID NO:48)
M10    SAKDINCQCIKTYSKPFHPKFIKELRVIESGPHCANTEIIVKLSDGRELCLDPKENWVQRVVEKFLKRAENS   (SEQ ID NO:49)
M64    SAKELRCQCIKTYSKPFHPKFIKELRVIESGPHCANTEIIVKLSDGRELCLDPKENWVQRVVEK           (SEQ ID NO:21)

PF4    EAEEDGDLQCLCVKTTSQVRPRHITSLEVIKAGPHCPTAQLIATLKNGRKICLDLQAPLYKKIIKKLLES     (SEQ ID NO:6)
M2     SAKELRCQCVKTTSQVRPRHITSLEVIKAGPHCPTAQLIATLKNGRKICLDLQAPLYKKIIKKLLES        (SEQ ID NO:22)
411    EAEEDGDLRCLCVKTTSQVRPRHITSLEVIKAGPHCPTAQLIATLKNGRKICLDLQAPLYKKIIKKLLES     (SEQ ID NO:23)
412    EAEEDGDLQCLCVKTTSQVRPRHITSLEVIKAGPHCPTAQLIATLKNGRKLCLDPKENWVKKIIKKLLES     (SEQ ID NO:24)
413    EAEEDGDLQCLCVKTTSQVRPRHITSLEVIKAGPHCPTAQLIATLKNGRKICLDPDAPRIKKIIKKLLES     (SEQ ID NO:25)
414    EAEEDGDLQCLCVKTTSQVRPRHITSLEVIKAGPHCPTAQLIATLKNGRKACLNPASPIVKIIKKLLES      (SEQ ID NO:26)
421    EAEEDGDLQCLCVKTTSQVRPRHIKELRVIEAGPHCPTAQLIATLKNGRKICLDLQAPLYKKIIKKLLES     (SEQ ID NO:27)
426    EAEEDGDLQCLCVKTTSQVPQHITSLEVIKAGPHCPTAQLIATLKNGQKICLDLQAPLYKKIIKKLLES      (SEQ ID NO:28)
```

FIG. 2

FIG. 3A (SEQ ID NO:29)

```
     ccgcagcatgagctccgcagccgggttctgcgcctcacgccccgggctgctgttcctggg
1    ------------+---------+---------+---------+---------+---------+    60
     ggcgtcgtactcgaggcgtcggcccaagacgcggagtgcggggcccgacgacaaggaccc

M  S  S  A  A  G  F  C  A  S  R  P  G  L  L  F  L  G       (18)

|_____PF4-1_____
     gttgctgctcctgccacttgtggtcgccttcgccagcgctgaagctgaagaagatgggga
61   ------------+---------+---------+---------+---------+---------+   120
     caacgacgaggacggtgaacaccagcggaagcggtcgcgacttcgacttcttctaccct L  L  L  L  P  L  V  V  A  F  A  S  A/ E  A  E  E  D  G  D     (38)
                                          (SEQ ID NO:66)
     _____PF4-1_____| (SEQ ID NO:30)
     cctgcagtgcctgtgtgtgaagaccacctccaggtccgtcccaggcacatcaccagcct
121  ------------+---------+---------+---------+---------+---------+   180
     ggacgtcacggacacacacttctggtggagggtccaggcagggtccgtgtagtggtcgga
                                      |========================PF4-2============
                                                   (SEQ ID NO:31)
       L  Q  C  L  C  V  K  T  T  S  Q  V  R  P  R  H  I  T  S  L     (58)

|-·-·-·-·-·-·-·-PF4-3-·-·-·-·-·-·-·-
     ggaggtgatcaaggccggacccactgccccactgcccaactgatagccacgctgaagaa
181  ------------+---------+---------+---------+---------+---------+   240
     cctccactagttccggcctggggtgacggggtgacgggttgactatcggtgcgacttctt
     ==================PF4-2=================================

E  V  I  K  A  G  P  H  C  P  T  A  Q  L  I  A  T  L  K  N     (78)

·-·-·-·-   -·-·-·-·-·-·-·-·-·-·-·-PF4-3-·-·-·-·-·-·-·-·-·-·-·
     tggaaggaaaatttgcttggacctgcaagcccgctgtacaagaaaataattaagaaact
241  ------------+---------+---------+---------+---------+---------+   300
     accttcctttaaacgaacctggacgttcgggcgacatgttcttttattaattctttga
                     (SEQ ID NO:33) |************PF4-4*********

G  R  K  I  C  L  D  L  Q  A  P  L  Y  K  K  I  I  K  K  L     (98)

-·•| PF4-3 (SEQ ID NO:32)
     tttggagagttag (SEQ ID NO:29)
301  ------------+---                                                  313
     aaacctctcaatc
     **PF4-4**

L  E  S (SEQ ID NO:6)                                          (101)
```

FIG. 3B (SEQ ID NO:34)

```
                               (SEQ ID NO:35)
                     _____PF4M2-1_____▶
        ATGAGTGCTAAAGAACTTAGATGTCAGTGCGTGAAGACCACCTCCCAGGTCCGTCCCAGG
  70    +---------+---------+---------+---------+---------+---------  130
        TACTCACGATTTCTTGAATCTACAGTCACGCACTTCTGGTGGAGGGTCCAGGCAGGGTCC

M  S  A  K  E  L  R  C  Q  C  V  K  T  T  S  Q  V  R  P  R  -

CACATCACCAGCCTGGAGGTGATCAAGGCCGGACCCCACTGCCCCACTGCTCAGCTGATA
  131   +---------+---------+---------+---------+---------+---------  190
        GTGTAGTGGTCGGACCTCCACTAGTTCCGGCCTGGGGTGACGGGGTGACGAGTCGACTAT

H  I  T  S  L  E  V  I  K  A  G  P  H  C  P  T  A  Q  L  I  -

GCCACGCTGAAGAATGGAAGGAAAATTTGCTTGGACCTGCAAGCCCCGCTGTACAAGAAA
  191   +---------+---------+---------+---------+---------+---------  250
        CGGTGCGACTTCTTACCTTCCTTTTAAACGAACCTGGACGTTCGGGGCGACATGTTCTTT
                                                (SEQ ID NO:33) ◄===========
         A  T  L  K  N  G  R  K  I  C  L  D  L  Q  A  P  L  Y  K  K  -

ATAATTAAGAAACTTTTGGAGAGTTAG  (SEQ ID NO:34)
  251   +---------+---------+------- 277
        TATTAATTCTTTGAAAACCTCTCAATC
        ========PF4-4============

I  I  K  K  L  L  E  S   - (SEQ ID NO:67)
```

FIG. 3C (SEQ ID NO:57)

```
     ccgcagcatgagctccgcagccgggttctgcgcctcacgccccgggctgctgttcctggg
  1  ------------+---------+---------+---------+---------+---------+   60
     ggcgtcgtactcgaggcgtcggcccaagacgcggagtgcggggcccgacgacaaggaccc

M  S  S  A  A  G  F  C  A  S  R  P  G  L  L  F  L  G     (18)

|————PF4-1————————
     gttgctgctcctgccacttgtggtcgccttcgccagcgctgaagctgaagaagatgggga
 61  ------------+---------+---------+---------+---------+---------+  120
     caacgacgaggacggtgaacaccagcggaagcggtcgcgacttcgacttcttctaccct L  L  L  P  L  V  V  A  F  A /E  A  E  E  D  G  D          (38)
                              (SEQ ID NO:66)
     ————————PF4-1——————————————————————→| (SEQ ID NO:30)
     cctgcagtgcctgtgtgtgaagaccacctcccaggtccgtcccaggcacatcaccagcct
121  ------------+---------+---------+---------+---------+---------+  180
     ggacgtcacggacacacacttctggtggagggtccaggcagggtccgtgtagtggtcgga
     |◄===================================PF4-2==============
                                     (SEQ ID NO:31)

L  Q  C  L  C  V  K  T  T  S  Q  V  R  P  R  H  I  T  S  L  (58)

-·-·-·-·-·-·-·-PF4-3-·-·-·-·-·-·-·-·-·-·-·-·
     ggaggtgatcaaggccggaccccactgccccactgcccaactgatagccacgctcaagaa
181  ------------+---------+---------+---------+---------+---------+  240
     cctccactagttccggcctggggtgacggggtgacgggttgactatcggtgcgagttctt
     =====================PF4-2===================|◄*********

E  V  I  K  A  G  P  H  C  P  T  A  Q  L  I  A  T  L  K  N  (78)

-·-·-·-·-·-·-·-·-·-·-PF4-3-·-·-·-·-·-·-·-·-·-·-·-·-·-·-·-·-·
     tggaaggaaagcttgcttgaacccggcatccccgattgtcaagaaaataattaagaaact
241  ------------+---------+---------+---------+---------+---------+  300
     accttcctttcgaacgaacttgggccgtaggggctaacagttcttttattaattctttga
     ***********************************************PF4-414-1*******

G  R  K  A  C  L  N  P  A  S  P  I  V  K  K  I  I  K  K  L  (98)

-·►| PF4-3 (SEQ ID NO:32)
     tttggagagttag (SEQ ID NO:57)
301  ------------+---                                                   313
     aaacctctcaatc
     ****PF414-1** (SEQ ID NO:58)

L  E  S  (SEQ ID NO:26)                                      (101)
```

FIG. 3D (SEQ ID NO:59)

```
                            |_____PF4-426-1_____
                    gtggatatcaagcttcatatggaagctgaagaagatgggga
                    +---------+---------+---------+---------+     120
                    cacctatagttcgaagtatacctcgacttcttctaccct
                                    M  E  A  E  E  D  G  D        (38)

_____PF4-426-1_____| (SEQ ID NO:60)
    cctgcagtgcctgtgtgtgaagaccacctcccaggtccagccccagcacatcaccagcct
121 ----------+---------+---------+---------+---------+---------+  180
    ggacgtcacggacacacacttctggtggagggtccaggtcggggtcgtgtagtggtcgga
                        |=================PF4-426-2===========
                                            (SEQ ID NO:61)
    L  Q  C  L  C  V  K  T  T  S  Q  V  Q  P  Q  H  I  T  S  L   (58)

-·-·-·-·-·-·-·-·-·-·-·PF4-426-3-·-·-·-·-·-·-·-·-·-·-·-
    ggaggtgatcaaggccggacccactgccccactgcccaactgatagccacgctgaagaa
181 ----------+---------+---------+---------+---------+---------+  240
    cctccactagttccggcctggggtgacggggtgacgggttgactatcggtgcgacttctt
    ================PF4-426-2=============

E  V  I  K  A  G  P  H  C  P  T  A  Q  L  I  A  T  L  K  N  (78)

-·-·-·-·-·-·-·-·-·-·-·PF4-426-3-·-·-·-·-·-·-·| SEQ ID NO:62)
    tggacagaaaattgcttggacctgcaagccccgctgtacaagaaaataattaagaaact
241 ----------+---------+---------+---------+---------+---------+  300
    acctgtcttttaaacgaacctggacgttcggggcgacatgttcttttattaattctttga
                    (SEQ ID NO:33) |*************PF4-4*********

G  Q  K  I  C  L  D  L  Q  A  P  L  Y  K  K  I  I  K  K  L  (98)

tttggagagttag (SEQ ID NO:59)
301 ----------+---                                                  313
    aaacctctcaatc
    **PF4-4**

L  E  S  (SEQ ID NO:68)                                        (101)
```

FIG. 4A (SEQ ID NO:36)

```
                             (SEQ ID NO:37)
                    _____IL-8-1_____▶
        atgagtgctaaagaacttagatgtcagtgcataaagacatactccaaacctttccacccc
     1  ------------+---------+---------+---------+---------+---------+ 60
        tactcacgatttcttgaatctacagtcacgtatttctgtatgaggtttggaaaggtgggg
                              (SEQ ID NO:38) ◄......IL-8-2......

M  S  A  K  E  L  R  C  Q  C  I  K  T  Y  S  K  P  F  H  P  -

--·IL-8-3-·--•
        aaatttatcaaagaactgagagtgattgagagtggaccacactgcgccaacacagaaatt
    61  ---------+---------+---------+---------+---------+---------+ 120
        tttaaatagtttcttgactctcactaactctcacctggtgtgacgcggttgtgtctttaa
        ..........................IL-8-2..........................

K  F  I  K  E  L  R  V  I  E  S  G  P  H  C  A  N  T  E  I  -

-·-·-·-·-·-·-·-·-·-·-IL-8-3-·-·-·-·-·-·-·-·-·-·-·-·-·-·-·-·-
        attgtaaagctttctgatggaagagagctctgtctggaccccaaggaaaactgggtgcag
   121  ---------+---------+---------+---------+---------+---------+
        taacatttcgaaagactaccttctctcgagacagacctggggttccttttgacccacgtc
        .....IL-8-2.........

I  V  K  L  S  D  G  R  E  L  C  L  D  P  K  E  N  W  V  Q  -

·-·-·-·-·-·-·-·-IL-8-3-·-·-·-·-·▶ (SEQ ID NO:39)
        agggttgtggagaagttttgaagagggctgagaattca (SEQ ID NO:36)
   181  ---------+---------+---------+--------- 219
        tcccaacacctcttcaaaaacttctcccgactcttaagt
           ◄===============IL-8-4===============
                    (SEQ ID NO:40)
         R  V  V  E  K  F  L  K  R  A  E  N  S  (SEQ ID NO:69)
```

FIG. 4B (SEQ ID NO:41)

```
                  _____IL-8M1-1_____►|  (SEQ ID NO:42)
        ATGAGTGCTAAAGACCTGCAGTGTCAGTGCATAAAGACATACTCCAAACCTTTCCACCCC
    4   ------------+---------+---------+---------+---------+---------+---  63
        TACTCACGATTTCTGGACGTCACAGTCACGTATTTCTGTATGAGGTTTGGAAAGGTGGGG

M  S  A  K  D  L  Q  C  Q  C  I  K  T  Y  S  K  P  F  H  P  -

AAATTTATCAAAGAACTGAGAGTGATTGAGAGTGGACCACACTGCGCCAACACAGAAATT
   64   ------------+---------+---------+---------+---------+---------+---  123
        TTTAAATAGTTTCTTGACTCTCACTAACTCTCACCTGGTGTGACGCGGTTGTGTCTTTAA

K  F  I  K  E  L  R  V  I  E  S  G  P  H  C  A  N  T  E  I  -

ATTGTAAAGCTAAGCGATGGAAGAGAGCTGTGTCTGGACCCCAAGGAAAACTGGGTGCAG
  124   ------------+---------+---------+---------+---------+---------+---  183
        TAACATTTCGATTCGCTACCTTCTCTCGACACAGACCTGGGGTTCCTTTTGACCCACGTC

I  V  K  L  S  D  G  R  E  L  C  L  D  P  K  E  N  W  V  Q  -

AGGGTTGTGGAGAAGTTTTTGAAGAGGGCTGAGAATTCA   (SEQ ID NO:41)
  184   ------------+---------+---------+---  222
        TCCCAACACCTCTTCAAAAACTTCTCCCGACTCTTAAGT
                |◄===============IL-8-4===============
                        (SEQ ID NO:40)
         R  V  V  E  K  F  L  K  R  A  E  N  S    (SEQ ID NO:70)
```

FIG. 4C (SEQ ID NO:52)

```
         _____IL-8M8-1_____| (SEQ ID NO:53)
         caagctcatatgagtgctaaagaactgcagtgtcagtgcataaagacatactccaaacctttccacccc
      1  ----------+---------+---------+---------+---------+---------+--------- 69
         gttcgagtatactcacgatttcttgacgtcacagtcacgtatttctgtatgaggtttggaaaggtgggg M   S   A   K   E   L   Q   C   Q   C   I   K   T   Y   S   K   P   F   H   P   - aaatttatcaaagaactgagagtgattgagagtggaccacactgcgccaacacagaaatt
     70  ----------+---------+---------+---------+---------+---------+--------- 129
         tttaaatagtttcttgactctcactaactctcacctggtgtgacgcggttgtgtctttaa K   F   I   K   E   L   R   V   I   E   S   G   P   H   C   A   N   T   E   I   - attgtaaagctaagcgatggaagagagctgtgtctggaccccaaggaaaactgggtgcag
    130  ----------+---------+---------+---------+---------+---------+--------- 189
         taacattcgattcgctaccttctctcgacacagacctggggttccttttgacccacgtc I   V   K   L   S   D   G   R   E   L   C   L   D   P   K   E   N   W   V   Q   - agggttgtggagaagttttgaagagggctgagaattca (SEQ ID NO:52)
    190  ----------+---------+---------+--------- 228
         tcccaacacctcttcaaaaacttctcccgactcttaagt
                   |==============IL-8-4==============  (SEQ ID NO:40)

R   V   V   E   K   F   L   K   R   A   E   N   S       (SEQ ID NO:63)
```

FIG. 4D (SEQ ID NO:54)

```
                    ___IL-8M9-1_____→|  (SEQ ID NO:55)
      caagcttcatatgagtgctaaagatctgcgttgtcagtgcataaagacatactccaaacctttccacccc
   1  ----------+---------+---------+---------+---------+---------+ 70
      gttcgaagtatactcacgatttctagacgcaacagtcacgtatttctgtatgaggtttggaaaggtgggg

M  S  A  K  D  L  R  C  Q  C  I  K  T  Y  S  K  P  F  H  P   - aaatttatcaaagaactgagagtgattgagagtggaccacactgcgccaacacagaaatt
  71  ----------+---------+---------+---------+---------+ 150
      tttaaatagtttcttgactctcactaactctcacctggtgtgacgcggttgtgtctttaa

K  F  I  K  E  L  R  V  I  E  S  G  P  H  C  A  N  T  E  I    - attgtaaagctaagcgatggaagagagctgtgtctggaccccaaggaaaactgggtgcag
 151  ----------+---------+---------+---------+---------+ 210
      taacatttcgattcgctaccttctctcgacacagacctggggttccttttgacccacgtc

I  V  K  L  S  D  G  R  E  L  C  L  D  P  K  E  N  W  V  Q    - agggttgtggagaagttttgaagagggctgagaattca  (SEQ ID NO:54)
 211  ----------+---------+---------+---------- 229
      tcccaacacctcttcaaaaacttctcccgactcttaagt
             |←================IL-8-4=============  (SEQ ID NO:40)

R  V  V  E  K  F  L  K  R  A  E  N  S   - (SEQ ID NO:64)
```

FIG. 4E (SEQ ID NO:50)

```
                    |_____IL-8M10-1_____>| (SEQ ID NO:51)
      caagcttcatatgagtgctaaagacctgaactgtcagtgcataaagacatactccaaacctttccacccc
  1   ----------+----------+----------+----------+----------+----------+  70
      gttcgaagtactcacgatttctggacttcacagtcacgtatttctgtatgaggtttggaaaggtgggg

M  S  A  K  D  L  N  C  Q  C  I  K  T  Y  S  K  P  F  H  P  - aaatttatcaaagaactgagagtgattgagagtggaccacactgcgccaacacagaaatt
 71   ----------+----------+----------+----------+----------+----------+ 130
      tttaaatagtttcttgactctcactaactctcacctggtgtgacgcggttgtgtctttaa

K  F  I  K  E  L  R  V  I  E  S  G  P  H  C  A  N  T  E  I    - attgtaaagctaagcgatggaagagagctgtgtctggaccccaaggaaaactgggtgcag
131   ----------+----------+----------+----------+----------+----------+ 190
      taacatttcgattcgctaccttctctcgacacagacctggggttccttttgacccacgtc

I  V  K  L  S  D  G  R  E  L  C  L  D  P  K  E  N  W  V  Q    - agggttgtggagaagttttgaagagggctgagaattca   (SEQ ID NO:50)
191   ----------+----------+----------+--------  229
      tcccaacacctcttcaaaaacttctcccgactcttaagt
                   |<========IL-8-4==========  (SEQ ID NO:40)

R  V  V  E  K  F  L  K  R  A  E  N  S   -  (SEQ ID NO:65)
```

```
 80 ATGAGTGCTAAAGAACTTAGAGATGTCAGTGCATAAAGACATACTCCAAACC 129
    ||||||||||||||||||||||||||||||||||||||||||||||||||||
293 ATGAGTGCTAAAGAACTTAGAGATGTCAGTGCATAAAGACATACTCCAAACC 244

130 TTTCCACCCCAAATTTATCAAAGAATACAGACGTATTGAGAGTGGACCAC 179
    |||||||||||||||||||||||||||||||||||||||||||||||||
243 TTTCCACCCCAAATTTATCAAAGAATACAGACGTATTGAGAGTGGACCAC 194

180 ACTGCGCCAACACAGAAAATTATTGTAAAGCTAAGCGATGAAGAGAGCTG 229
    |||||||||||||||||||||||||||||||||||||||||||||||||
193 ACTGCGCCAACACAGAAAATTATTGTAAAGCTAAGCGATGAAGAGAGCTG 144

230 TGTCTGGACCCCAAGGAAAACTGGGTGCAGAGGGTTGTGAGAAGTTTTT 279
    |||||||||||||||||||||||||||||||||||||||||||||||||
143 TGTCTGGACCCCAAGGAAAACTGGGTGCAGAGGGTTGTGAGAAGTTTTT 94

280 GAAGAGGGCTGAGAATTCATAGTAAGGATCC 310
    |||||||||||||||||||||||||||||||    (SEQ ID NO: 56)
 93 GAAGAGGGCTGAGAATTCATAGTAAGGATCC 63
```

FIG. 4F

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser  Ala  Lys  Glu  Leu  Arg  Cys  Gln  Cys  Ile  Lys  Thr  Tyr  Ser  Lys  Pro
1              5                        10                       15

Phe  His  Pro  Lys  Phe  Ile  Lys  Glu  Leu  Arg  Val  Ile  Glu  Ser  Gly  Pro
               20                       25                       30

His  Cys  Ala  Asn  Thr  Glu  Ile  Ile  Val  Lys  Leu  Ser  Asp  Gly  Arg  Glu
          35                        40                      45

Leu  Cys  Leu  Asp  Pro  Lys  Glu  Asn  Trp  Val  Gln  Arg  Val  Val  Glu  Lys
     50                       55                      60

Phe  Leu  Lys  Arg  Ala  Glu  Asn  Ser
65                       70
```

( 2 ) INFORMATION FOR SEQ ID NO:2:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ala  Ser  Val  Ala  Thr  Glu  Leu  Arg  Cys  Gln  Cys  Leu  Gln  Thr  Leu  Gln
1              5                        10                       15

Gly  Ile  His  Pro  Lys  Asn  Ile  Gln  Ser  Val  Asn  Val  Lys  Ser  Pro  Gly
               20                       25                       30

Pro  His  Cys  Ala  Gln  Thr  Glu  Val  Ile  Ala  Thr  Leu  Lys  Asn  Gly  Arg
          35                        40                      45

Lys  Ala  Cys  Leu  Asn  Pro  Ala  Ser  Pro  Ile  Val  Lys  Lys  Ile  Ile  Glu
     50                       55                      60

Lys  Met  Leu  Asn  Ser  Asp  Lys  Ser  Asn
65                       70
```

( 2 ) INFORMATION FOR SEQ ID NO:3:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ala  Pro  Leu  Ala  Thr  Glu  Leu  Arg  Cys  Gln  Cys  Leu  Gln  Thr  Leu  Gln
1              5                        10                       15

Gly  Ile  His  Leu  Lys  Asn  Ile  Gln  Ser  Val  Asn  Val  Lys  Ser  Pro  Gly
               20                       25                       30

Pro  His  Cys  Ala  Gln  Thr  Glu  Val  Ile  Ala  Thr  Leu  Lys  Asn  Gly  Gln
          35                        40                      45

Lys  Ala  Cys  Leu  Asn  Pro  Ala  Ser  Pro  Met  Val  Lys  Lys  Ile  Ile  Glu
     50                       55                      60

Lys  Met  Glu  Lys  Asn  Gly  Lys  Ser  Asn
65                       70
```

( 2 ) INFORMATION FOR SEQ ID NO:4:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

| Ala | Ser | Val | Val | Thr | Glu | Leu | Arg | Cys | Gln | Cys | Leu | Gln | Thr | Leu | Gln |
|---|---|---|---|---|---|---|---|---|---|---|---|---|---|---|---|
| 1 | | | | 5 | | | | | 10 | | | | | 15 | |

| Gly | Ile | His | Leu | Lys | Asn | Ile | Gln | Ser | Val | Asn | Val | Arg | Ser | Pro | Gly |
|---|---|---|---|---|---|---|---|---|---|---|---|---|---|---|---|
| | | | 20 | | | | 25 | | | | | 30 | | | |

| Pro | His | Cys | Ala | Gln | Thr | Glu | Val | Ile | Ala | Thr | Leu | Lys | Asn | Gly | Lys |
|---|---|---|---|---|---|---|---|---|---|---|---|---|---|---|---|
| | | 35 | | | | 40 | | | | | 45 | | | | |

| Lys | Ala | Cys | Leu | Asn | Pro | Ala | Ser | Pro | Met | Val | Gln | Lys | Ile | Ile | Glu |
|---|---|---|---|---|---|---|---|---|---|---|---|---|---|---|---|
| | 50 | | | | | 55 | | | | | 60 | | | | |

| Lys | Ile | Leu | Asn | Lys | Gly | Ser | Thr | Asn |
|---|---|---|---|---|---|---|---|---|
| 65 | | | | | 70 | | | |

( 2 ) INFORMATION FOR SEQ ID NO:5:

( i ) SEQUENCE CHARACTERISTICS:
       ( A ) LENGTH: 70 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:5:

| Ala | Glu | Leu | Arg | Cys | His | Cys | Ile | Lys | Thr | Thr | Ser | Gly | Ile | His | Pro |
|---|---|---|---|---|---|---|---|---|---|---|---|---|---|---|---|
| 1 | | | | 5 | | | | | 10 | | | | | 15 | |

| Lys | Asn | Ile | Gln | Ser | Leu | Glu | Val | Ile | Gly | Lys | Gly | Thr | His | Cys | Asn |
|---|---|---|---|---|---|---|---|---|---|---|---|---|---|---|---|
| | | | 20 | | | | 25 | | | | | 30 | | | |

| Gln | Val | Glu | Val | Ile | Ala | Thr | Leu | Lys | Asp | Gly | Arg | Lys | Ile | Cys | Leu |
|---|---|---|---|---|---|---|---|---|---|---|---|---|---|---|---|
| | | 35 | | | | 40 | | | | | 45 | | | | |

| Asp | Pro | Asp | Ala | Pro | Arg | Ile | Lys | Lys | Ile | Val | Gln | Lys | Lys | Leu | Ala |
|---|---|---|---|---|---|---|---|---|---|---|---|---|---|---|---|
| | 50 | | | | | 55 | | | | | 60 | | | | |

| Gly | Asp | Glu | Ser | Ala | Asp |
|---|---|---|---|---|---|
| 65 | | | | | 70 |

( 2 ) INFORMATION FOR SEQ ID NO:6:

( i ) SEQUENCE CHARACTERISTICS:
       ( A ) LENGTH: 70 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:6:

| Glu | Ala | Glu | Glu | Asp | Gly | Asp | Leu | Gln | Cys | Leu | Cys | Val | Lys | Thr | Thr |
|---|---|---|---|---|---|---|---|---|---|---|---|---|---|---|---|
| 1 | | | | 5 | | | | | 10 | | | | | 15 | |

| Ser | Gln | Val | Arg | Pro | Arg | His | Ile | Thr | Ser | Leu | Glu | Val | Ile | Lys | Ala |
|---|---|---|---|---|---|---|---|---|---|---|---|---|---|---|---|
| | | | 20 | | | | 25 | | | | | 30 | | | |

| Gly | Pro | His | Cys | Pro | Thr | Ala | Gln | Leu | Ile | Ala | Thr | Leu | Lys | Asn | Gly |
|---|---|---|---|---|---|---|---|---|---|---|---|---|---|---|---|
| | | 35 | | | | 40 | | | | | 45 | | | | |

| Arg | Lys | Ile | Cys | Leu | Asp | Leu | Gln | Ala | Pro | Leu | Tyr | Lys | Lys | Ile | Ile |
|---|---|---|---|---|---|---|---|---|---|---|---|---|---|---|---|
| | 50 | | | | | 55 | | | | | 60 | | | | |

| Lys | Lys | Leu | Leu | Glu | Ser |
|---|---|---|---|---|---|
| 65 | | | | | 70 |

( 2 ) INFORMATION FOR SEQ ID NO:7:

( i ) SEQUENCE CHARACTERISTICS:

(A) LENGTH: 77 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

| Val | Pro | Leu | Ser | Arg | Thr | Val | Arg | Cys | Thr | Cys | Ile | Ser | Ile | Ser | Asn |
|---|---|---|---|---|---|---|---|---|---|---|---|---|---|---|---|
| 1 | | | | 5 | | | | | 10 | | | | | 15 | |

| Gln | Pro | Val | Asn | Pro | Arg | Ser | Leu | Glu | Lys | Leu | Glu | Ile | Ile | Pro | Ala |
|---|---|---|---|---|---|---|---|---|---|---|---|---|---|---|---|
| | | | 20 | | | | | 25 | | | | | 30 | | |

| Ser | Gln | Phe | Cys | Pro | Arg | Val | Glu | Ile | Ile | Ala | Thr | Met | Lys | Lys | Lys |
|---|---|---|---|---|---|---|---|---|---|---|---|---|---|---|---|
| | | 35 | | | | | 40 | | | | | 45 | | | |

| Gly | Glu | Lys | Arg | Cys | Leu | Asn | Pro | Glu | Ser | Lys | Ala | Ile | Lys | Asn | Leu |
|---|---|---|---|---|---|---|---|---|---|---|---|---|---|---|---|
| | 50 | | | | | 55 | | | | | 60 | | | | |

| Leu | Lys | Ala | Val | Ser | Lys | Glu | Met | Ser | Lys | Arg | Ser | Pro |
|---|---|---|---|---|---|---|---|---|---|---|---|---|
| 65 | | | | | 70 | | | | | 75 | | |

(2) INFORMATION FOR SEQ ID NO:8:

(i) SEQUENCE CHARACTERISTICS:
(A) LENGTH: 78 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

| Ala | Gly | Pro | Ala | Ala | Ala | Val | Leu | Arg | Glu | Leu | Arg | Cys | Val | Cys | Leu |
|---|---|---|---|---|---|---|---|---|---|---|---|---|---|---|---|
| 1 | | | | 5 | | | | | 10 | | | | | 15 | |

| Gln | Thr | Thr | Gln | Gly | Val | His | Pro | Lys | Met | Ile | Ser | Asn | Leu | Gln | Val |
|---|---|---|---|---|---|---|---|---|---|---|---|---|---|---|---|
| | | | 20 | | | | | 25 | | | | | 30 | | |

| Phe | Ala | Ile | Gly | Pro | Gln | Cys | Ser | Lys | Val | Glu | Val | Val | Ala | Ser | Leu |
|---|---|---|---|---|---|---|---|---|---|---|---|---|---|---|---|
| | | 35 | | | | | 40 | | | | | 45 | | | |

| Lys | Asn | Gly | Lys | Glu | Ile | Cys | Leu | Asp | Pro | Glu | Ala | Pro | Phe | Leu | Lys |
|---|---|---|---|---|---|---|---|---|---|---|---|---|---|---|---|
| | 50 | | | | | 55 | | | | | 60 | | | | |

| Lys | Val | Ile | Gln | Lys | Ile | Leu | Asp | Gly | Gly | Asn | Lys | Glu | Asn |
|---|---|---|---|---|---|---|---|---|---|---|---|---|---|
| 65 | | | | | 70 | | | | | 75 | | | |

(2) INFORMATION FOR SEQ ID NO:9:

(i) SEQUENCE CHARACTERISTICS:
(A) LENGTH: 81 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

| Gly | Lys | Glu | Glu | Ser | Leu | Asp | Ser | Asp | Leu | Tyr | Ala | Glu | Leu | Arg | Cys |
|---|---|---|---|---|---|---|---|---|---|---|---|---|---|---|---|
| 1 | | | | 5 | | | | | 10 | | | | | 15 | |

| Met | Cys | Ile | Lys | Thr | Thr | Ser | Gly | Ile | His | Pro | Lys | Asn | Ile | Gln | Ser |
|---|---|---|---|---|---|---|---|---|---|---|---|---|---|---|---|
| | | | 20 | | | | | 25 | | | | | 30 | | |

| Leu | Glu | Val | Ile | Gly | Lys | Gly | Thr | His | Cys | Asn | Gln | Val | Glu | Val | Ile |
|---|---|---|---|---|---|---|---|---|---|---|---|---|---|---|---|
| | | 35 | | | | | 40 | | | | | 45 | | | |

| Ala | Thr | Leu | Lys | Asp | Gly | Arg | Lys | Ile | Cys | Leu | Asp | Pro | Asp | Ala | Pro |
|---|---|---|---|---|---|---|---|---|---|---|---|---|---|---|---|
| | 50 | | | | | 55 | | | | | 60 | | | | |

| Arg | Ile | Lys | Lys | Ile | Val | Gln | Lys | Lys | Leu | Ala | Gly | Asp | Glu | Ser | Ala |
|---|---|---|---|---|---|---|---|---|---|---|---|---|---|---|---|
| 65 | | | | | 70 | | | | | 75 | | | | | 80 |

Asp ( 2 ) INFORMATION FOR SEQ ID NO:10:

( i ) SEQUENCE CHARACTERISTICS:
        ( A ) LENGTH: 84 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Asn Leu Ala Lys Gly Lys Glu Glu Ser Leu Asp Ser Asp Leu Tyr Ala
 1               5                  10                  15
Glu Leu Arg Cys Met Cys Ile Lys Thr Thr Ser Gly Ile His Pro Lys
             20                  25                  30
Asn Ile Gln Ser Leu Glu Val Ile Gly Lys Gly Thr His Cys Asn Gln
                 35                  40                  45
Val Glu Val Ile Ala Thr Leu Lys Asp Gly Arg Lys Ile Cys Leu Asp
             50                  55                  60
Pro Asp Ala Pro Arg Ile Lys Lys Ile Val Gln Lys Lys Leu Ala Gly
 65                  70                  75                  80
Asp Glu Ser Ala
```

( 2 ) INFORMATION FOR SEQ ID NO:11:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ser Ser Thr Lys Gly Gln Thr Lys Arg Asn Leu Ala Lys Gly Lys Glu
 1               5                  10                  15
Glu Ser Leu Asp Ser Asp Leu Tyr Ala Glu Leu Arg Cys Met Cys Ile
             20                  25                  30
Lys Thr Thr Ser Gly Ile His Pro Lys Asn Ile Gln Ser Leu Glu Val
             35                  40                  45
Ile Gly Lys Gly Thr His Cys Asn Gln Val Glu Val Ile Ala Thr Leu
         50                  55                  60
Lys Asp Gly Arg Lys Ile Cys Leu Asp Pro Asp Ala Pro Arg Ile Lys
 65                  70                  75                  80
Lys Ile Val Gln Lys Lys Leu Ala Gly Asp Glu Ser Ala Asp
                 85                  90
```

( 2 ) INFORMATION FOR SEQ ID NO:12:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
His Met Gln Pro Asp Ala Ile Asn Ala Pro Val Thr Cys Cys Tyr Asn
 1               5                  10                  15
Phe Thr Asn Arg Lys Ile Ser Val Gln Arg Leu Ala Ser Tyr Arg Arg
```

|    |    |     |     |     |     |     | 20  |     |     |     |     | 25  |     |     |     |     | 30  |     |     |
|----|----|-----|-----|-----|-----|-----|-----|-----|-----|-----|-----|-----|-----|-----|-----|-----|-----|-----|-----|

Ile Thr Ser Ser Lys Cys Pro Lys Glu Ala Val Ile Phe Lys Thr Ile
        35                40                45

Val Ala Lys Glu Ile Cys Ala Asp Pro Lys Gln Lys Trp Val Gln Asp
50                    55                60

Ser Met Asp His Leu Asp Lys Gln Thr Gln Thr Pro Lys Thr
65                  70                75

( 2 ) INFORMATION FOR SEQ ID NO:13:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Phe Ser Ala Ser Leu Ala Ala Asp Thr Pro Thr Ala Cys Cys Phe Ser
1                5                10                15

Tyr Thr Ser Arg Gln Ile Pro Gln Asn Phe Ile Ala Asp Tyr Phe Glu
        20                25              30

Thr Ser Ser Gln Cys Ser Lys Pro Gly Val Ile Phe Leu Thr Lys Arg
        35                40              45

Ser Arg Gln Val Cys Ala Asp Pro Ser Glu Glu Trp Val Gln Lys Tyr
    50                55                60

Val Ser Asp Leu Glu Leu Ser Ala
65                  70

( 2 ) INFORMATION FOR SEQ ID NO:14:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Pro Tyr Ser Ser Asp Thr Thr Pro Cys Cys Phe Ala Tyr Ile Ala Arg
1                5                10                15

Pro Leu Asp Arg Ala His Ile Lys Glu Tyr Phe Tyr Thr Ser Gly Lys
        20                25              30

Cys Ser Asn Pro Ala Val Val Phe Val Thr Arg Lys Asn Arg Gln Val
        35                40              45

Cys Ala Asn Pro Glu Lys Lys Trp Tyr Arg Glu Tyr Ile Asn Ser Leu
    50                55                60

Glu Met
65

( 2 ) INFORMATION FOR SEQ ID NO:15:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Gly Ser Asp Pro Pro Thr Ala Cys Cys Phe Ser Tyr Thr Ala Arg Lys
  1               5                  10                     15

Leu Pro Arg Asn Phe Val Val Asp Tyr Tyr Glu Thr Ser Ser Leu Cys
             20                  25                  30

Ser Gln Pro Ala Val Val Phe Gln Thr Lys Arg Ser Lys Gln Val Cys
             35                  40                  45

Ala Asp Pro Ser Glu Ser Trp Val Gln Glu Tyr Val Tyr Asp Leu Glu
         50                  55                  60

Leu
 65
```

(2) INFORMATION FOR SEQ ID NO:16:

(i) SEQUENCE CHARACTERISTICS:
(A) LENGTH: 72 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:16:

```
Ser Ala Lys Asp Leu Gln Cys Gln Cys Ile Lys Thr Tyr Ser Lys Pro
  1               5                  10                     15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
             35                  40                  45

Leu Cys Leu Asp Pro Lys Glu Asn Trp Val Gln Arg Val Val Glu Lys
         50                  55                  60

Phe Leu Lys Arg Ala Glu Asn Ser
 65                  70
```

(2) INFORMATION FOR SEQ ID NO:17:

(i) SEQUENCE CHARACTERISTICS:
(A) LENGTH: 72 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

```
Ser Ala Lys Glu Leu Arg Cys Gln Cys Ile Lys Thr Tyr Ser Lys Pro
  1               5                  10                     15

Phe His Pro Lys Phe Ile Lys Glu Tyr Arg Arg Ile Glu Ser Gly Pro
             20                  25                  30

His Cys Ala Asn Thr Glu Ile Ile Val Lys Leu Ser Asp Gly Arg Glu
             35                  40                  45

Leu Cys Leu Asp Pro Lys Glu Asn Trp Val Gln Arg Val Val Glu Lys
         50                  55                  60

Phe Leu Lys Arg Ala Glu Asn Ser
 65                  70
```

(2) INFORMATION FOR SEQ ID NO:18:

(i) SEQUENCE CHARACTERISTICS:
(A) LENGTH: 72 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

| Ser | Ala | Lys | Glu | Leu | Arg | Cys | Gln | Cys | Ile | Lys | Thr | Tyr | Ser | Lys | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | His | Pro | Lys | Phe | Ile | Lys | Leu | Glu | Arg | Val | Ile | Glu | Ser | Gly | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Cys | Ala | Asn | Thr | Glu | Ile | Ile | Val | Lys | Leu | Ser | Asp | Gly | Arg | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Leu | Cys | Leu | Asp | Pro | Lys | Glu | Asn | Trp | Val | Gln | Arg | Val | Val | Glu | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Phe | Leu | Lys | Arg | Ala | Glu | Asn | Ser |
|-----|-----|-----|-----|-----|-----|-----|-----|
| 65  |     |     |     |     | 70  |     |     |

(2) INFORMATION FOR SEQ ID NO:19:

(i) SEQUENCE CHARACTERISTICS:
  (A) LENGTH: 72 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:19:

| Ser | Ala | Lys | Glu | Leu | Arg | Cys | Gln | Cys | Ile | Lys | Thr | Tyr | Ser | Lys | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | His | Pro | Lys | Phe | Ile | Lys | Glu | Leu | Arg | Ala | Ile | Glu | Ser | Gly | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Cys | Ala | Asn | Thr | Glu | Ile | Ile | Val | Lys | Leu | Ser | Asp | Gly | Arg | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Leu | Cys | Leu | Asp | Pro | Lys | Glu | Asn | Trp | Val | Gln | Arg | Val | Val | Glu | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Phe | Leu | Lys | Arg | Ala | Glu | Asn | Ser |
|-----|-----|-----|-----|-----|-----|-----|-----|
| 65  |     |     |     |     | 70  |     |     |

(2) INFORMATION FOR SEQ ID NO:20:

(i) SEQUENCE CHARACTERISTICS:
  (A) LENGTH: 68 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:20:

| Ser | Ala | Lys | Glu | Leu | Arg | Cys | Gln | Cys | Ile | Lys | Thr | Tyr | Ser | Lys | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | His | Pro | Lys | Phe | Ile | Lys | Glu | Leu | Arg | Val | Ile | Glu | Ser | Gly | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Cys | Ala | Asn | Thr | Glu | Ile | Ile | Val | Lys | Leu | Ser | Asp | Gly | Arg | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Leu | Cys | Leu | Asp | Leu | Gln | Ala | Pro | Leu | Tyr | Lys | Lys | Ile | Ile | Lys | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Leu | Leu | Glu | Ser |
|-----|-----|-----|-----|
| 65  |     |     |     |

(2) INFORMATION FOR SEQ ID NO:21:

(i) SEQUENCE CHARACTERISTICS:

(A) LENGTH: 64 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:21:

```
Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
    50                  55                  60
```

(2) INFORMATION FOR SEQ ID NO:22:

(i) SEQUENCE CHARACTERISTICS:
(A) LENGTH: 67 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

```
Ser Ala Lys Glu Leu Arg Cys Gln Cys Val Lys Thr Thr Ser Gln Val
 1               5                  10                  15

Arg Pro Arg His Ile Thr Ser Leu Glu Val Ile Lys Ala Gly Pro His
                20                  25                  30

Cys Pro Thr Ala Gln Leu Ile Ala Thr Leu Lys Asn Gly Arg Lys Ile
            35                  40                  45

Cys Leu Asp Leu Gln Ala Pro Leu Tyr Lys Lys Ile Ile Lys Lys Leu
    50                  55                  60

Leu Glu Ser
65
```

(2) INFORMATION FOR SEQ ID NO:23:

(i) SEQUENCE CHARACTERISTICS:
(A) LENGTH: 70 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:23:

```
Glu Ala Glu Glu Asp Gly Asp Leu Arg Cys Leu Cys Val Lys Thr Thr
 1               5                  10                  15

Ser Gln Val Arg Pro Arg His Ile Thr Ser Leu Glu Val Ile Lys Ala
                20                  25                  30

Gly Pro His Cys Pro Thr Ala Gln Leu Ile Ala Thr Leu Lys Asn Gly
            35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70
```

(2) INFORMATION FOR SEQ ID NO:24:

( i ) SEQUENCE CHARACTERISTICS:
  ( A ) LENGTH: 70 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:24:

```
Glu Ala Glu Glu Asp Gly Asp Leu Gln Cys Leu Cys Val Lys Thr Thr
1               5                   10                  15
Ser Gln Val Arg Pro Arg His Ile Thr Ser Leu Glu Val Ile Lys Ala
            20                  25                  30
Gly Pro His Cys Pro Thr Ala Gln Leu Ile Ala Thr Leu Lys Asn Gly
        35                  40                  45
Arg Lys Leu Cys Leu Asp Pro Lys Glu Asn Trp Val Lys Lys Ile Ile
    50                  55                  60
Lys Lys Leu Leu Glu Ser
65                  70
```

( 2 ) INFORMATION FOR SEQ ID NO:25:

( i ) SEQUENCE CHARACTERISTICS:
  ( A ) LENGTH: 70 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:25:

```
Glu Ala Glu Glu Asp Gly Asp Leu Gln Cys Leu Cys Val Lys Thr Thr
1               5                   10                  15
Ser Gln Val Arg Pro Arg His Ile Thr Ser Leu Glu Val Ile Lys Ala
            20                  25                  30
Gly Pro His Cys Pro Thr Ala Gln Leu Ile Ala Thr Leu Lys Asn Gly
        35                  40                  45
Arg Lys Ile Cys Leu Asp Pro Asp Ala Pro Arg Ile Lys Lys Ile Ile
    50                  55                  60
Lys Lys Leu Leu Glu Ser
65                  70
```

( 2 ) INFORMATION FOR SEQ ID NO:26:

( i ) SEQUENCE CHARACTERISTICS:
  ( A ) LENGTH: 70 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:26:

```
Glu Ala Glu Glu Asp Gly Asp Leu Gln Cys Leu Cys Val Lys Thr Thr
1               5                   10                  15
Ser Gln Val Arg Pro Arg His Ile Thr Ser Leu Glu Val Ile Lys Ala
            20                  25                  30
Gly Pro His Cys Pro Thr Ala Gln Leu Ile Ala Thr Leu Lys Asn Gly
        35                  40                  45
Arg Lys Ala Cys Leu Asn Pro Ala Ser Pro Ile Val Lys Lys Ile Ile
    50                  55                  60
Lys Lys Leu Leu Glu Ser
65                  70
```

( 2 ) INFORMATION FOR SEQ ID NO:27:

( i ) SEQUENCE CHARACTERISTICS:
      ( A ) LENGTH: 70 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:27:

```
Glu Ala Glu Glu Asp Gly Asp Leu Gln Cys Leu Cys Val Lys Thr Thr
 1               5                  10                  15

Ser Gln Val Arg Pro Arg His Ile Lys Glu Leu Arg Val Ile Glu Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70
```

( 2 ) INFORMATION FOR SEQ ID NO:28:

( i ) SEQUENCE CHARACTERISTICS:
      ( A ) LENGTH: 70 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:28:

```
Glu Ala Glu Glu Asp Gly Asp Leu Gln Cys Leu Cys Val Lys Thr Thr
 1               5                  10                  15

Ser Gln Val Gln Pro Gln His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Gln Lys Ile Cys Leu Asp Leu Gln Ala Pro Leu Tyr Lys Lys Ile Ile
    50                  55                  60

Lys Lys Leu Leu Glu Ser
65                  70
```

( 2 ) INFORMATION FOR SEQ ID NO:29:

( i ) SEQUENCE CHARACTERISTICS:
      ( A ) LENGTH: 310 base pairs
      ( B ) TYPE: nucleic acid
      ( C ) STRANDEDNESS: double
      ( D ) TOPOLOGY: linear ( i i ) MOLECULE TYPE: DNA ( x i ) SEQUENCE DESCRIPTION: SEQ ID NO:29:

```
CCGCAGCATG AGCTCCGCAG CCGGGTTCTG CGCCTCACGC CCCGGGCTGC TGTTCCTGGG    60

GTTGCTGCTC CTGCCACTTG TGGTCGCCTT CGCCAGCGCT GAAGCTGAAG AAGATGGGGA   120

CCTGCAGTGC CTGTGTGTGA AGACCACCTC CCAGGTCCGT CCCAGGCACA TCACCAGCCT   180

GGAGGTGATC AAGGCCGGAC CCCACTGCCC CACTGCCCAA CTGATAGCCA CGCTGAAGAA   240

TGGAAGGAAA ATTTGCTTGG ACCTGCAAGC CCCGCTGTAC AAGAAAATAA TTAAGAAACT   300
```

TTTGGAGAGT 310

(2) INFORMATION FOR SEQ ID NO:30:

(i) SEQUENCE CHARACTERISTICS:
  (A) LENGTH: 57 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:30:

GAAGCTGAAG AAGATGGGGA CCTGCAGTGC CTGTGTGTGA AGACCACCTC CCAGGTC 57

(2) INFORMATION FOR SEQ ID NO:31:

(i) SEQUENCE CHARACTERISTICS:
  (A) LENGTH: 100 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:31:

CGTGGCTATC AGTTGGGCAG TGGGGCAGTG GGGTCCGGCC TTGATCACCT CCAGGCTGGT 60

GATGTGCCTG GGACGGACCT GGGAGGTGGT CTTCACACAC 100

(2) INFORMATION FOR SEQ ID NO:32:

(i) SEQUENCE CHARACTERISTICS:
  (A) LENGTH: 99 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:32:

CTGCCCCACT GCCCAACTGA TAGCCACGCT GAAGAATGGA AGGAAAATTT GCTTGGACCT 60

GCAAGCCCCG CTGTACAAGA AATAATTAA GAAACTTTT 99

(2) INFORMATION FOR SEQ ID NO:33:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:33:

CTAACTCTCC AAAAGTTTCT TAATTATTTT CTTGTACAGC 40

(2) INFORMATION FOR SEQ ID NO:34:

(i) SEQUENCE CHARACTERISTICS:
  (A) LENGTH: 207 base pairs
  (B) TYPE: nucleic acid
  (C) STRANDEDNESS: double
  (D) TOPOLOGY: linear (ii) MOLECULE TYPE: DNA (xi) SEQUENCE DESCRIPTION: SEQ ID NO:34:

ATGAGTGCTA AAGAACTTAG ATGTCAGTGC GTGAAGACCA CCTCCCAGGT CCGTCCCAGG 60

```
CACATCACCA  GCCTGGAGGT  GATCAAGGCC  GGACCCCACT  GCCCCACTGC  TCAGCTGATA        120

GCCACGCTGA  AGAATGGAAG  GAAAATTTGC  TTGGACCTGC  AAGCCCCGCT  GTACAAGAAA        180

ATAATTAAGA  AACTTTTGGA  GAGTTAG                                               207
```

( 2 ) INFORMATION FOR SEQ ID NO:35:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

```
ATGAGTGCTA  AAGAACTTAG  ATGTCAGTGC  GTGAAGACCA  CCTCCCAGGT  CCGTCCC           57
```

( 2 ) INFORMATION FOR SEQ ID NO:36:

( i ) SEQUENCE CHARACTERISTICS:
        ( A ) LENGTH: 219 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:36:

```
ATGAGTGCTA  AAGAACTTAG  ATGTCAGTGC  ATAAAGACAT  ACTCCAAACC  TTTCCACCCC        60

AAATTTATCA  AAGAACTGAG  AGTGATTGAG  AGTGGACCAC  ACTGCGCCAA  CACAGAAATT        120

ATTGTAAAGC  TTTCTGATGG  AAGAGAGCTC  TGTCTGGACC  CCAAGGAAAA  CTGGGTGCAG        180

AGGGTTGTGG  AGAAGTTTTT  GAAGAGGGCT  GAGAATTCA                                 219
```

( 2 ) INFORMATION FOR SEQ ID NO:37:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

```
ATGAGTGCTA  AAGAACTTAG  ATGTCAGTGC  ATAAAGACAT  ACTCCAAACC  TTTCCACCC         59
```

( 2 ) INFORMATION FOR SEQ ID NO:38:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

```
CCATCAGAAA  GCTTTACAAT  AATTTCTGTG  TTGGCGCAGT  GTGGTCCACT  CTCAATCACT        60

CTCAGTTCTT  TGATAAATTT  GGGGTGGAAA  GGTTTGGAG                                 99
```

( 2 ) INFORMATION FOR SEQ ID NO:39:

( i ) SEQUENCE CHARACTERISTICS:
        ( A ) LENGTH: 99 base pairs (B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:39:

| AACACAGAAA | TTATTGTAAA | GCTTTCTGAT | GGAAGAGAGC | TCTGTCTGGA | CCCCAAGGAA | 60 |
| AACTGGGTGC | AGAGGGTTGT | GGAGAAGTTT | TTGAAGAGG | | | 99 |

(2) INFORMATION FOR SEQ ID NO:40:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:40:

| TGAATTCTCA | GCCCTCTTCA | AAAACTTCTC | CACAACC | 37 |

(2) INFORMATION FOR SEQ ID NO:41:

(i) SEQUENCE CHARACTERISTICS:
        (A) LENGTH: 219 base pairs
        (B) TYPE: nucleic acid
        (C) STRANDEDNESS: double
        (D) TOPOLOGY: linear (i i) MOLECULE TYPE: DNA (x i) SEQUENCE DESCRIPTION: SEQ ID NO:41:

| ATGAGTGCTA | AAGACCTGCA | GTGTCAGTGC | ATAAAGACAT | ACTCCAAACC | TTTCCACCCC | 60 |
| AAATTTATCA | AAGAACTGAG | AGTGATTGAG | AGTGGACCAC | ACTGCGCCAA | CACAGAAATT | 120 |
| ATTGTAAAGC | TAAGCGATGG | AAGAGAGCTG | TGTCTGGACC | CCAAGGAAAA | CTGGGTGCAG | 180 |
| AGGGTTGTGG | AGAAGTTTTT | GAAGAGGGCT | GAGAATTCA | | | 219 |

(2) INFORMATION FOR SEQ ID NO:42:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:42:

| ATGAGTGCTA | AAGACCTGCA | GTGTCAGTGC | ATAAAGACAT | ACTCCAA | 47 |

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:43:

Ile Ala Thr Leu Lys Asn Gly Gln Lys
1               5

( 2 ) INFORMATION FOR SEQ ID NO:44:

( i ) SEQUENCE CHARACTERISTICS:
　　　　　　　　( A ) LENGTH: 11 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: peptide ( x i ) SEQUENCE DESCRIPTION: SEQ ID NO:44:

```
Ala  Cys  Leu  Asn  Pro  Ala  Ser  Pro  Ile  Val  Lys
1                  5                        10
```

( 2 ) INFORMATION FOR SEQ ID NO:45:

( i ) SEQUENCE CHARACTERISTICS:
　　　　　　　　( A ) LENGTH: 10 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: peptide ( x i ) SEQUENCE DESCRIPTION: SEQ ID NO:45:

```
Met  Ser  Ala  Lys  Glu  Leu  Arg  Cys  Gln  Cys
1                  5                        10
```

( 2 ) INFORMATION FOR SEQ ID NO:46:

( i ) SEQUENCE CHARACTERISTICS:
　　　　　　　　( A ) LENGTH: 12 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: peptide ( x i ) SEQUENCE DESCRIPTION: SEQ ID NO:46:

```
Glu  Ala  Glu  Glu  Asp  Gly  Asp  Leu  Gln  Cys  Leu  Gln
1                  5                        10
```

( 2 ) INFORMATION FOR SEQ ID NO:47:

( i ) SEQUENCE CHARACTERISTICS:
　　　　　　　　( A ) LENGTH: 72 amino acids
　　　　　　　　( B ) TYPE: amino acid
　　　　　　　　( C ) STRANDEDNESS: Not Relevant
　　　　　　　　( D ) TOPOLOGY: linear ( i i ) MOLECULE TYPE: protein ( x i ) SEQUENCE DESCRIPTION: SEQ ID NO:47:

```
Ser  Ala  Lys  Glu  Leu  Gln  Cys  Gln  Cys  Ile  Lys  Thr  Tyr  Ser  Lys  Pro
1                  5                        10                            15

Phe  His  Pro  Lys  Phe  Ile  Lys  Glu  Leu  Arg  Val  Ile  Glu  Ser  Gly  Pro
              20                        25                        30

His  Cys  Ala  Asn  Thr  Glu  Ile  Ile  Val  Lys  Leu  Ser  Asp  Gly  Arg  Glu
                   35                   40                        45

Leu  Cys  Leu  Asp  Pro  Lys  Glu  Asn  Trp  Val  Gln  Arg  Val  Val  Glu  Lys
         50                   55                        60

Phe  Leu  Lys  Arg  Ala  Glu  Asn  Ser
65                        70
```

( 2 ) INFORMATION FOR SEQ ID NO:48:

( i ) SEQUENCE CHARACTERISTICS:
　　　　　　　　( A ) LENGTH: 52 amino acids ( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:48:

```
Ser Ala Lys Asp Leu Arg Cys Gln Cys Ile Lys Thr Tyr Ser Lys Pro
 1               5                  10                  15
Phe His Pro Lys Phe Ile Lys Glu Leu Arg Val Ile Glu Ser Gly Pro
                20                  25                  30
His Cys Ala Asn Thr Glu Ile Arg Val Val Glu Lys Phe Leu Lys Arg
            35                  40                  45
Ala Glu Asn Ser
            50
```

( 2 ) INFORMATION FOR SEQ ID NO:49:

( i ) SEQUENCE CHARACTERISTICS:
( A ) LENGTH: 72 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:49:

```
Ser Ala Lys Asp Leu Asn Cys Gln Cys Ile Lys Thr Tyr Ser Lys Pro
 1               5                  10                  15
Phe His Pro Lys Phe Ile Lys Glu Leu Arg Val Ile Glu Ser Gly Pro
                20                  25                  30
His Cys Ala Asn Thr Glu Ile Ile Val Lys Leu Ser Asp Gly Arg Glu
            35                  40                  45
Leu Cys Leu Asp Pro Lys Glu Asn Trp Val Gln Arg Val Val Glu Lys
        50                  55                  60
Phe Leu Lys Arg Ala Glu Asn Ser
65              70
```

( 2 ) INFORMATION FOR SEQ ID NO:50:

( i ) SEQUENCE CHARACTERISTICS:
( A ) LENGTH: 229 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:50:

```
CAAGCTTCAT ATGAGTGCTA AAGACCTGAA CTGTCAGTGC ATAAAGACAT ACTCCAAACC      60
TTTCCACCCC AAATTTATCA AGAACTGAG AGTGATTGAG AGTGGACCAC ACTGCGCCAA      120
CACAGAAATT ATTGTAAAGC TAAGCGATGG AAGAGAGCTG TGTCTGGACC CCAAGGAAAA     180
CTGGGTGCAG AGGGTTGTGG AGAAGTTTTT GAAGAGGGCT GAGAATTCA                 229
```

( 2 ) INFORMATION FOR SEQ ID NO:51:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: protein ( x i ) SEQUENCE DESCRIPTION: SEQ ID NO:51:

CAAGCTTCAT ATGAGTGCTA AAGACCTGAA CTGTCAG    37

( 2 ) INFORMATION FOR SEQ ID NO:52:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

CAAGCTCATA TGAGTGCTAA AGAACTGCAG TGTCAGTGCA TAAAGACATA CTCCAAACCT    60

TTCCACCCCA AATTTATCAA AGAACTGAGA GTGATTGAGA GTGGACCACA CTGCGCCAAC    120

ACAGAAATTA TTGTAAAGCT AAGCGATGGA AGAGAGCTGT GTCTGGACCC CAAGGAAAAC    180

TGGGTGCAGA GGGTTGTGGA GAAGTTTTTG AAGAGGGCTG AGAATTCA    228

( 2 ) INFORMATION FOR SEQ ID NO:53:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

CAAGCTCATA TGAGTGCTAA AGAACTGCAG TGTCAGTGCA    40

( 2 ) INFORMATION FOR SEQ ID NO:54:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

CAAGCTTCAT ATGAGTGCTA AAGATCTGCG TTGTCAGTGC ATAAAGACAT ACTCCAAACC    60

TTTCCACCCC AAATTTATCA AGAACTGAG AGTGATTGAG AGTGGACCAC ACTGCGCCAA    120

CACAGAAATT ATTGTAAAGC TAAGCGATGG AAGAGAGCTG TGTCTGGACC CCAAGGAAAA    180

CTGGGTGCAG AGGGTTGTGG AGAGTTTTT GAAGAGGGCT GAGAATTCA    228

( 2 ) INFORMATION FOR SEQ ID NO:55:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

CAAGCTTCAT ATGAGTGCTA AAGATCTGCG TTGTCAG    37

( 2 ) INFORMATION FOR SEQ ID NO:56:

( i ) SEQUENCE CHARACTERISTICS:

(A) LENGTH: 231 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:56:

| | | | | | |
|---|---|---|---|---|---|
| ATGAGTGCTA | AAGAACTTAG | ATGTCAGTGC | ATAAAGACAT | ACTCCAAACC | TTTCCACCCC | 60 |
| AAATTTATCA | AAGAATACAG | ACGTATTGAG | AGTGGACCAC | ACTGCGCCAA | CACAGAAATT | 120 |
| ATTGTAAAGC | TAAGCGATGG | AAGAGAGCTG | TGTCTGGACC | CCAAGGAAAA | CTGGGTGCAG | 180 |
| AGGGTTGTGG | AGAAGTTTTT | GAAGAGGGCT | GAGAATTCAT | AGTAAGGATC | C | 231 |

(2) INFORMATION FOR SEQ ID NO:57:

(i) SEQUENCE CHARACTERISTICS:
(A) LENGTH: 313 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:57:

| | | | | | |
|---|---|---|---|---|---|
| CCGCAGCATG | AGCTCCGCAG | CCGGGTTCTG | CGCCTCACGC | CCCGGGCTGC | TGTTCCTGGG | 60 |
| GTTGCTGCTC | CTGCCACTTG | TGGTCGCCTT | CGCCAGCGCT | GAAGCTGAAG | AAGATGGGGA | 120 |
| CCTGCAGTGC | CTGTGTGTGA | AGACCACCTC | CCAGGTCCGT | CCCAGGCACA | TCACCAGCCT | 180 |
| GGAGGTGATC | AAGGCCGGAC | CCCACTGCCC | CACTGCCCAA | CTGATAGCCA | CGCTCAAGAA | 240 |
| TGGAAGGAAA | GCTTGCTTGA | ACCCGGCATC | CCCGATTGTC | AAGAAAATAA | TTAAGAAACT | 300 |
| TTTGGAGAGT | TAG | | | | | 313 |

(2) INFORMATION FOR SEQ ID NO:58:

(i) SEQUENCE CHARACTERISTICS:
(A) LENGTH: 83 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:58:

| | | | | | |
|---|---|---|---|---|---|
| CTAACTCTCC | AAAAGTTTCT | TAATTATTTT | CTTGACAATC | GGGGATGCCG | GGTTCAAGCA | 60 |
| AGCTTTCCTT | CCATTCTTGA | GCG | | | | 83 |

(2) INFORMATION FOR SEQ ID NO:59:

(i) SEQUENCE CHARACTERISTICS:
(A) LENGTH: 234 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:59:

| | | | | | |
|---|---|---|---|---|---|
| GTGGATATCA | AGCTTCATAT | GGAAGCTGAA | GAAGATGGGG | ACCTGCAGTG | CCTGTGTGTG | 60 |
| AAGACCACCT | CCCAGGTCCA | GCCCAGCAC | ATCACCAGCC | TGGAGGTGAT | CAAGGCCGGA | 120 |
| CCCCACTGCC | CCACTGCCCA | ACTGATAGCC | ACGCTGAAGA | ATGGACAGAA | AATTTGCTTG | 180 |
| GACCTGCAAG | CCCCGCTGTA | CAAGAAAATA | ATTAAGAAAC | TTTTGGAGAG | TTAG | 234 |

( 2 ) INFORMATION FOR SEQ ID NO:60:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

```
TGGAAGCTGA AGAAGATGGG GACCTGCAGT GCCTGTGTGT GAAGACCACC TCCCAGGTCC    60
AGCCCCA                                                              67
```

( 2 ) INFORMATION FOR SEQ ID NO:61:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

```
GGCAGTGGGG CAGTGGGGTC CGGCCTTGAT CACCTCCAGG CTGGTGATGT GCTGGGGCTG    60
GACCTGGGAG GTGGT                                                     75
```

( 2 ) INFORMATION FOR SEQ ID NO:62:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

```
GGCCGGACCC CACTGCCCCA CTGCCCAACT GATAGCCACG CTGAAGAATG GACAGAAAAT    60
TTGCTTGGAC CTGCAAGCCC CGCTGTAC                                       88
```

( 2 ) INFORMATION FOR SEQ ID NO:63:

( i ) SEQUENCE CHARACTERISTICS:
        ( A ) LENGTH: 73 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:63:

```
Met Ser Ala Lys Glu Leu Gln Cys Gln Cys Ile Lys Thr Tyr Ser Lys
 1               5                  10                  15
Pro Phe His Pro Lys Phe Ile Lys Glu Leu Arg Val Ile Glu Ser Gly
                20                  25                  30
Pro His Cys Ala Asn Thr Glu Ile Ile Val Lys Leu Ser Asp Gly Arg
            35                  40                  45
Glu Leu Cys Leu Asp Pro Lys Glu Asn Trp Val Gln Arg Val Val Glu
        50                  55                  60
Lys Phe Leu Lys Arg Ala Glu Asn Ser
    65                  70
```

( 2 ) INFORMATION FOR SEQ ID NO:64:

( i ) SEQUENCE CHARACTERISTICS:
        ( A ) LENGTH: 53 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:64:

```
Met Ser Ala Lys Asp Leu Arg Cys Gln Cys Ile Lys Thr Tyr Ser Lys
1               5                   10                  15

Pro Phe His Pro Lys Phe Ile Lys Glu Leu Arg Val Ile Glu Ser Gly
            20                  25                  30

Pro His Cys Ala Asn Thr Glu Ile Arg Val Val Glu Lys Phe Leu Lys
        35                  40                  45

Arg Ala Glu Asn Ser
        50
```

( 2 ) INFORMATION FOR SEQ ID NO:65:

( i ) SEQUENCE CHARACTERISTICS:
        ( A ) LENGTH: 73 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:65:

```
Met Ser Ala Lys Asp Leu Asn Cys Gln Cys Ile Lys Thr Tyr Ser Lys
1               5                   10                  15

Pro Phe His Pro Lys Phe Ile Lys Glu Leu Arg Val Ile Glu Ser Gly
            20                  25                  30

Pro His Cys Ala Asn Thr Glu Ile Ile Val Lys Leu Ser Asp Gly Arg
        35                  40                  45

Glu Leu Cys Leu Asp Pro Lys Glu Asn Trp Val Gln Arg Val Val Glu
        50                  55                  60

Lys Phe Leu Lys Arg Ala Glu Asn Ser
65                  70
```

( 2 ) INFORMATION FOR SEQ ID NO:66:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:66:

```
Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala
            20                  25                  30
```

( 2 ) INFORMATION FOR SEQ ID NO:67:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:67:

| Met | Ser | Ala | Lys | Glu | Leu | Arg | Cys | Gln | Cys | Val | Lys | Thr | Thr | Ser | Gln |
| 1 | | | | 5 | | | | | 10 | | | | | 15 | |

| Val | Arg | Pro | Arg | His | Ile | Thr | Ser | Leu | Glu | Val | Ile | Lys | Ala | Gly | Pro |
| | | | 20 | | | | | 25 | | | | | 30 | | |

| His | Cys | Pro | Thr | Ala | Gln | Leu | Ile | Ala | Thr | Leu | Lys | Asn | Gly | Arg | Lys |
| | | 35 | | | | | 40 | | | | | 45 | | | |

| Ile | Cys | Leu | Asp | Leu | Gln | Ala | Pro | Leu | Tyr | Lys | Lys | Ile | Ile | Lys | Lys |
| | 50 | | | | | 55 | | | | | 60 | | | | |

| Leu | Leu | Glu | Ser |
| 65 | | | |

( 2 ) INFORMATION FOR SEQ ID NO:68:

( i ) SEQUENCE CHARACTERISTICS:
 ( A ) LENGTH: 71 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:68:

| Met | Glu | Ala | Glu | Glu | Asp | Gly | Asp | Leu | Gln | Cys | Leu | Cys | Val | Lys | Thr |
| 1 | | | | 5 | | | | | 10 | | | | | 15 | |

| Thr | Ser | Gln | Val | Arg | Pro | Arg | His | Ile | Thr | Ser | Leu | Glu | Val | Ile | Lys |
| | | | 20 | | | | | 25 | | | | | 30 | | |

| Ala | Gly | Pro | His | Cys | Pro | Thr | Ala | Gln | Leu | Ile | Ala | Thr | Leu | Lys | Asn |
| | | 35 | | | | | 40 | | | | | 45 | | | |

| Gly | Arg | Lys | Ile | Cys | Leu | Asp | Leu | Gln | Ala | Pro | Leu | Tyr | Lys | Lys | Ile |
| | 50 | | | | | 55 | | | | | 60 | | | | |

| Ile | Lys | Lys | Leu | Leu | Glu | Ser |
| 65 | | | | | 70 | |

( 2 ) INFORMATION FOR SEQ ID NO:69:

( i ) SEQUENCE CHARACTERISTICS:
 ( A ) LENGTH: 73 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:69:

| Met | Ser | Ala | Lys | Glu | Leu | Arg | Cys | Gln | Cys | Ile | Lys | Thr | Tyr | Ser | Lys |
| 1 | | | | 5 | | | | | 10 | | | | | 15 | |

| Pro | Phe | His | Pro | Lys | Phe | Ile | Lys | Glu | Leu | Arg | Val | Ile | Glu | Ser | Gly |
| | | | 20 | | | | | 25 | | | | | 30 | | |

| Pro | His | Cys | Ala | Asn | Thr | Glu | Ile | Ile | Val | Lys | Leu | Ser | Asp | Gly | Arg |
| | | 35 | | | | | 40 | | | | | 45 | | | |

| Glu | Leu | Cys | Leu | Asp | Pro | Lys | Glu | Asn | Trp | Val | Gln | Arg | Val | Val | Glu |
| | 50 | | | | | 55 | | | | | 60 | | | | |

| Lys | Phe | Leu | Lys | Arg | Ala | Glu | Asn | Ser |
| 65 | | | | | 70 | | | |

( 2 ) INFORMATION FOR SEQ ID NO:70:

( i ) SEQUENCE CHARACTERISTICS:
 ( A ) LENGTH: 73 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:70:

```
Met Ser Ala Lys Asp Leu Gln Cys Gln Cys Ile Lys Thr Tyr Ser Lys
 1            5                   10                      15
Pro Phe His Pro Lys Phe Ile Lys Glu Leu Arg Val Ile Glu Ser Gly
             20                   25                  30
Pro His Cys Ala Asn Thr Glu Ile Ile Val Lys Leu Ser Asp Gly Arg
         35                  40                  45
Glu Leu Cys Leu Asp Pro Lys Glu Asn Trp Val Gln Arg Val Val Glu
     50                  55                      60
Lys Phe Leu Lys Arg Ala Glu Asn Ser
 65                  70
```

CHEMOKINE-LIKE PROTEINS AND METHODS OF USE

This application is a continuation-in-part of U.S. application Ser. No. 08/330,163, filed Oct. 26, 1994.

BACKGROUND OF THE INVENTION

The invention relates to novel chemokine-like proteins and their use to suppress the proliferation of actively dividing myeloid cells, e.g., myeloid progenitor cells, myeloid stem cells, and leukemic cells, and to mobilize progenitor cells from the bone marrow to the peripheral blood.

Each year approximately 173,000 of the people who undergo chemotherapy become neutropenic, which causes them to become susceptible to infection and anemia (Hecht, *Drug and Market Development*, 4:49, 1993). One method of treatment for neutropenia, e.g., chemotherapy-induced neutropenia, includes stimulation of progenitor cells with differentiation factors including granulocyte macrophage-colony stimulating factor (GM-CSF), granulocyte-colony stimulating factor (G-CSF), and erythropoietin (EPO) as a method of salvaging cells surviving chemotherapy. Approximately 100,000 patients annually are suitable for receiving G-CSF for this purpose. G-CSF is used to stimulate growth of white blood cell progenitors, and EPO has been used to stimulate production of red blood cells, however, there are no megakaryocyte progenitor stimulating factors currently available.

An alternative approach for preventing neutropenia is to inhibit cell proliferation with low doses of various chemokines, which inhibits cell cycling, thereby protecting the progenitor cells from the effects of chemotherapy and/or radiation therapy. After chemotherapy has ended, the chemokine treatment is also stopped, which allows the progenitor cells to resume normal proliferation.

Chemokines are small inducible proteins that are related by amino acid homology, chromosome location, and structural similarities, including the presence of four position-invariant cysteine residues in their primary amino acid sequence that form two disulfide bonds. The amino acid sequences of various naturally occurring, wild-type chemokine proteins are shown in FIG. 1.

Certain chemokines, known as beta chemokines, have a Cys-Cys pair as the first two cysteines, and include macrophage inflammatory protein-1 alpha (MIP-1α), MIP-1β, macrophage chemotactic and activating factor (MCAF, also known as monocyte chemo-attractant protein-1 (MCP-1)), MCP-3, and Regulated on Activation, Normal T-cell Expressed and Secreted protein (RANTES). The beta chemokines are potent chemoattractants for a variety of blood cell components, including monocytes, eosinophils, and T-lymphocytes, but not neutrophils.

Other chemokines, known as alpha chemokines, have a Cys-X-Cys triplet as the first two cysteines (X can be any amino acid other than cysteine), and include the human-derived proteins interleukin-8 (IL-8), GRO-α (also called melanoma-growth stimulating activity (MGSA/GRO), MIP-2α (also known as GRO-β), MIP-2β (also known as GRO-γ), neutrophil activating peptide-2 (NAP-2), platelet factor 4 (PF4), gamma interferon inducible protein 10 (γIP-10), Epithelial derived Neutrophil Activating protein (78 amino acids in length)(ENA-78), β-thromboglobulin (βTG), connective tissue-activating peptide-III (CTAP-III), and platelet basic protein (PBP). The alpha chemokines are potent chemoattractants and all except PF4 and γIP-10 activate neutrophils.

Chemokines have been shown to regulate proliferation and/or differentiation of hematopoietic stem and progenitor cells in vitro and in vivo. For example, MIP-1α, γIP-10, IL-8, Gro-β, PF4, and MCP-1 have been shown to inhibit the proliferation of colony forming unit-granulocyte macrophage (CFU-GM), burst forming unit-erythroid cells (BRU-E), and colony forming unit-multipotential progenitor cells (CFU-GEMM), at concentrations greater than 25 ng/ml when administered to mice. See, e.g., Broxmeyer et al., *J. Immunol.*, 150:3448–3458 (1993).

On the other hand, several members of the chemokine family, including NAP-2, Gro-α, Gro-γ, RANTES, and MIP-1β have been shown not to possess such inhibitory activities, but Gro-α and Gro-γ have been shown to interfere with the inhibitory activity of IL-8 and PF4. Furthermore, Broxmeyer et al., WO 94/13321, states that combinations of any two of MCAF, MIP-1α, MIP-2α, IL-8, γIP-10 and PF4 provide a decrease in the concentrations required for suppressing progenitor cell proliferation.

Several groups have also examined the ability of chemokines to inhibit the proliferation of progenitor cells in vivo. For example, Maze et al., *J. Immunol.*, 149:1004 (1992), observed that murine MIP-1α suppressed proliferation and absolute numbers of granulocyte-macrophage, erythroid, and multipotential progenitor cells from mice femurs and spleens at doses between 2 and 10 µg per mouse, injected intravenously. Murine MIP-1β, which was unable to inhibit cell proliferation in vitro, displayed no biological activity in vivo either.

Recombinant human chemokines have also been demonstrated to inhibit proliferation of CFU-GM, CFU-GEMM, and BFU-E following intravenous injection into mice. Furthermore, active chemokines cause a significant decrease in the number of progenitor cells in S-phase. For example, Dunlop et al., *Blood*, 79:2221 (1992), observed that recombinant human MIP-1α was able to suppress CFU-S in a dose dependent manner in vitro, and to reduce the high proliferative state of the CFU-S compartment to a quiescent state in vivo.

Human MIP-1a has been shown to protect progenitor cells in vivo from the cytotoxic effects of the chemotherapeutic drug cytosine arabinoside (ARA-C), and Caen et al., *Blood*, 82:162a (1993), has reported that PF4, at doses between 1 and 5 µg/mouse, protected hematopoietic precursor cells from the adverse effects of the chemotherapeutic, 5-fluorouracil. Lord et al., *Blood*, 79:2605–2609 (1992), also observed that MIP-1α protected myeloid progenitors in a murine system from the cytotoxic effects of hydroxyurea.

In addition, Gewirtz et al., *J. Clin. Invest.*, 68:56 (1989), observed that a peptide from PF4 containing the C-terminal 24 amino acids inhibited proliferation of megakaryocyte progenitors in vitro at a concentration of 25 µg/ml. A shorter peptide containing only the last 13 amino acids from PF4 was found to be inactive in the assay. Similarly, a peptide containing the C-terminal 18 amino acids from β-thromboglobulin did not inhibit proliferation.

Recently, Caen et al., *Blood*, 82:162a (1993), reported that a dodecapeptide, Asn-Gly-Arg-Lys-Ile-Cys-Leu-Asp-Leu-Glu-Ala-Pro, which is able to inhibit human and murine megakaryocyte and platelet production, can also protect hematopoietic precursor cells in vivo (1–5 µg/mouse) during 5-fluorouracil chemotherapy.

Although G-CSFs are the drugs most commonly used to treat chemically-induced neutropenia, they have certain drawbacks. For example, G-CSFs do not prevent a drop in white blood cell count, i.e., they do not avoid neutropenia, but merely shorten the low point or nadir in the blood count. G-CSFs also fail to stimulate platelet development, and thus do not protect platelets. Moreover, G-CSFs are expensive, and are therefore often administered only after the white cell count drops below about 1000.

SUMMARY OF THE INVENTION

The present invention is based on the discovery that the ability of chemokines to suppress the proliferation of actively dividing myeloid cells (e.g., myeloid progenitor cells, myeloid stem cells, and leukemic cells) is associated with the presence of at least two "active domains." "Active domains" are defined herein as regions of several contiguous amino acids in chemokines that, in combinations of two or more active domains, are necessary for myelosuppressive activity. The present inventors have determined the amino acid sequences of five of these active domains: 1) ELR (derived from IL-8), 2) ELRV (derived from IL-8), 3) DLQ (one of the two DLQ domains from PF4), 4) IATLKNGQK (SEQ ID NO:43) (derived from Groβ), and 5) ACLN-PASPIVK (SEQ ID NO:44) (derived from Groα). Various mutations of these sequences can serve as these active domains.

Based on these discoveries, the invention includes novel chemokine-like proteins that are based upon a wild-type chemokine amino acid sequence (the "template" chemokine) and modified to include at least one heterologous active domain, e.g., an active domain from a chemokine other than the template chemokine. The novel chemokine-like proteins thus contain at least two active domains, and exhibit myelosuppressive activity (i.e., suppress the proliferation of actively dividing myeloid cells). Certain of these new chemokine-like proteins have a much higher myelosuppressive activity than naturally occurring, wild-type chemokines.

Further based on these discoveries, the invention features the new proteins and methods to treat chemotherapy-induced, as well as radiation-induced, neutropenia. The invention also features new methods of screening and treating patients with certain myelogenous leukemias as well as other hyperproliferative blood diseases. In addition, the new proteins can be used to identify, purify, and expand progenitor-specific cell populations in an ex vivo setting for re-introduction into a patient following radiation or chemotherapy.

In general, the invention features a protein having the amino acid sequence of a wild-type chemokine having four cysteine residues, the amino acid sequence containing an active domain selected from: ELR, DLN, ELQ, DLR, ELRV, DLQ, IATLKNGQK (SEQ ID NO:43), and ACLN-PASPIVK (SEQ ID NO:44). Preferably, the active domain replaces a number of amino acids identical to the number of amino acids in the active domain, and is positioned in the protein such that the active domain is: 1) on the N-terminus side of and proximal the first cysteine residue of the wild-type chemokine; 2) on the N-terminus side of and within 11 amino acids of the third cysteine residue of the wild-type chemokine; 3) on the N-terminus side of and within 11 amino acids of the fourth cysteine residue of the wild-type chemokine; or 4) on the C-terminus side of and within 11 amino acids of the fourth cysteine residue of the wild-type chemokine.

In general, the invention features a protein having the amino acid sequence of a wild-type chemokine, e.g., IL-8, having four cysteine residues, with the following modifications: a) amino acids DLQ as the 3 contiguous amino acids on the N-terminus side of and proximal to the first cysteine residue of the wild-type chemokine; and b) amino acids $ELXVX_1X_2X_3X_4X_5X_6$ as the 10 amino acids on the N-terminus side of and proximal to the third cysteine of the wild-type chemokine, wherein X is any amino acid, e.g., R, N, E, or Q, and $X_1X_2X_3X_4X_5X_6$ can be any six consecutive amino acids on the N-terminus side of and proximal to the third cysteine of the wild-type chemokine. In particular, the protein can have the amino acid sequence SAKDLQC-QCIKTYSKPFHPKFIKELRVIESGPH-CANTEIIVKLSDGRELCLDPKEN-WVQRVVEKFLKRAENS (SEQ ID NO:16).

The invention additionally features a protein having the amino acid sequence of a wild-type chemokine, e.g., IL-8, having four cysteine residues, with the following modifications: a) amino acids ELQ as the 3 contiguous amino acids on the N-terminus side of and proximal to the first cysteine residue of the wild-type chemokine; and b) amino acids $ELXVX_1X_2X_3X_4X_5X_6$ as the 10 amino acids on the N-terminus side of and proximal to the third cysteine of the wild-type chemokine, wherein X is any amino acid, e.g., R, N, E, or Q, and $X_1X_2X_3X_4X_5X_6$ can be any six consecutive amino acids on the N-terminus side of and proximal to the third cysteine of the wild-type chemokine. In particular, the protein can have the amino acid sequence SAKELQCQCIK-TYSKPFHPKFIKELRVIESGPHCANTEI-IVKLSDGRELCLDPKENWVQR VVEKFLKRAENS (SEQ ID NO:47).

The invention additionally features a protein having the amino acid sequence of a wild-type chemokine, e.g., IL-8, having four cysteine residues, with the following modifications: a) amino acids DLR as the 3 contiguous amino acids on the N-terminus side of and proximal to the first cysteine residue of the wild-type chemokine; and b) amino acids $ELXVX_1X_2X_3X_4X_5X_6$ as the 10 amino acids on the N-terminus side of and proximal to the third cysteine of the wild-type chemokine, wherein X is any amino acid, e.g., R, N, E, or Q, and $X_1X_2X_3X_4X_5X_6$ can be any six consecutive amino acids on the N-terminus side of and proximal to the third cysteine of the wild-type chemokine. In particular, the protein can have the amino acid sequence SAKDLRCQCIK-TYSKPFHPKFIKELRVIESGPHCANTEI-IVKLSDGRELCLDPKENWVQRVVEKFLKRAENS (SEQ ID NO:48).

The invention additionally features a protein having the amino acid sequence of a wild-type chemokine, e.g., IL-8, having four cysteine residues, with the following modifications: a) amino acids DLN as the 3 contiguous amino acids on the N-terminus side of and proximal to the first cysteine residue of the wild-type chemokine; and b) amino acids $ELXVX_1X_2X_3X_4X_5X_6$ as the 10 amino acids on the N-terminus side of and proximal to the third cysteine of the wild-type chemokine, wherein X is any amino acid, e.g., R, N, E, or Q, and $X_1X_2X_3X_4X_5X_6$ can be any six consecutive amino acids on the N-terminus side of and proximal to the third cysteine of the wild-type chemokine. In particular, the protein can have the amino acid sequence SAKDLNC-QCIKTYSKPFHPKFIKELRVIESGPH-CANTEIIVKLSDGRELCLDPKEN-WVQRVVEKFLKRAENS (SEQ ID NO:49).

The invention further features a protein having the amino acid sequence of a wild-type chemokine, e.g., PF-4, having four cysteine residues, with the following modifications: a) amino acids ELR as the 3 contiguous amino acids on the N-terminus side of and proximal to the first cysteine residue of the wild-type chemokine; and b) amino acids XDLQ as the 4 amino acids on the C-terminus side of and proximal to the fourth cysteine of the wild-type chemokine; wherein X can be any amino acid, e.g., L. In particular, the protein can have the amino acid sequence SAKELRCQCVKTTSQVR-PRHITSLEVIKAGPHCPTAQLIATLKN-GRKICLDLQAPLYKKI IKKLLES (SEQ ID NO:22).

In addition, the invention features a protein having the amino acid sequence of a wild-type chemokine, e.g., PF4, having four cysteine residues, with the following modifications: a) amino acids DLQ as the 3 contiguous amino acids on the N-terminus side of and proximal to the first cysteine residue of the wild-type chemokine; and b) amino acids ACLNPASPIVK (SEQ ID NO:44) replacing 11 amino acids including the fourth cysteine of the wild-type chemokine, wherein the C in ACLNPASPIVK corresponds to the fourth cysteine residue. In particular, the protein can have the amino acid sequence EAEEDGDLQCLCVKTTSQVR-PRHITSLEVIKAGPHCPTAQLIATLKN-GRKACLNPASPIVKKIIKKLLES (SEQ ID NO:26).

The invention further features a protein having the amino acid sequence of a wild-type chemokine, e.g. PF4, having four cysteine residues, with the following modifications: a) amino acids DLQ as the 3 contiguous amino acids on the N-terminus side of and proximal to the first cysteine residue of the wild-type chemokine; and b) amino acids IATLKNGQK (SEQ ID NO:43) and Z as the 10 amino acids on the N-terminus side of and proximal to the fourth cysteine of the wild-type chemokine, wherein Z is any amino acid, e.g., I, A, L, or R. In particular, the protein can have the amino acid sequence EAEEDGDLQ-CLCVKTTSQVQPQHITSLEVIKAGPH-CPTAQLIATLKNGQKICLDLQAPLYKKIIKKLLES (SEQ ID NO:28).

In any of these new proteins, the wild-type chemokine can be, e.g., IL-8, GRO-α, MIP-2α, MIP-1α, PF4, NAP-2, ENA-78, PBP, CTAP-III, βTG, γIP-10, MCAF, or RANTES.

The invention also feature a protein having the amino acid sequence SAKELRCQCIKTYSKPFHPKFIKEYR-RIESGPHCANTEIIVKLSDGRELCLDP-KENWVQRVVEKFL (SEQ ID NO:17).

The invention also features a method of suppressing proliferation of an actively dividing myeloid cell by contacting the cell with an effective amount of any of the new chemokine-like proteins of the invention. The cell can be cultured in vitro, or ex vivo, or the cell can be in vivo.

Furthermore, the invention features an adjunctive method for use with chemotherapy or radiation therapy in a patient by administering an effective amount of a chemokine-like protein of the invention to the patient, and administering chemotherapy or radiation therapy to the patient in conjunction with the administration of the protein. As used herein, "in conjunction with" means before, during, or after, or any combination thereof.

The invention also features a method of treating a hyperproliferative myeloid disease, e.g., chronic myelogenous leukemia, polycythemia vera, or a hypermegakaryocytopoietic disorder, in a patient by administering to the patient an effective amount of a chemokine-like protein of the invention.

In addition, the invention features methods of detecting and/or isolating $CD34^+$ myeloid cells in a sample of cells by obtaining a sample of cells, contacting the sample with a chemokine-like protein under conditions that allow the protein to bind to any $CD34^+$ myeloid cells in the sample to form bound complexes, and detecting any bound complexes in the sample as an indication of the presence of $CD34^+$ myeloid cells in the sample, or removing any bound complexes from the sample, and separating $CD34^+$ myeloid cells from the bound complexes to isolate the $CD34^+$ myeloid cells from the sample.

The invention additionally features a method of isolating $CD34^+$ myeloid cells from the peripheral blood of a patient by administering an effective amount of a chemokine-like protein to the patient, and isolating $CD34^+$ myeloid cells from a peripheral blood sample from the patient.

The invention further features nucleic acids encoding the chemokine-like proteins of the invention, such as nucleic acids having the sequence of SEQ ID NO:34 or SEQ ID NO:41.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description including the drawings, and from the claims.

DRAWINGS

FIG. 1 is a representation of the wild-type amino acid sequences of representative members of the human chemokine family of proteins (SEQ ID NOS:1–15).

FIG. 2 is a representation of the amino acid sequences of novel chemokine-like proteins of the invention (SEQ ID NOS:16–28 and 47–49) compared to the wild-type amino acid sequences of IL-8 (SEQ ID NO:1) and PF4 (SEQ ID NO:6).

FIG. 3A is a representation of the nucleotide sequence of human PF4 CDNA (SEQ ID NO:29) and the translated amino acid sequence, (SEQ ID NOS:66 and 6) as well as the sequences of the four amplimers used for its synthesis (SEQ ID NOS:30–33).

FIG. 3B is a representation of the nucleotide sequence of the cDNA of new chemokine-like protein PF4M2 (SEQ ID NO:34) and the translated amino acid sequence, as well as the sequences of the two amplimers used for its synthesis (SEQ ID NOS:33 and 35).

FIG. 3C is a representation of the nucleotide sequence of the CDNA of new chemokine-like protein PF4-414 (SEQ ID NO:57) and the translated amino acid sequence, as well as the sequences of the amplimers used for its synthesis (SEQ ID NOS:58 and 30–32).

FIG. 3D is a representation of the nucleotide sequence of the cDNA of new chemokine-like protein PF4-426 (SEQ ID NO:59) and the translated amino acid sequence, as well as the sequences of the amplimers used for its synthesis (SEQ ID NOS:33 and 60–62).

FIG. 4A is a representation of the nucleotide sequence of human IL-8 cDNA (SEQ ID NO:36) and the translated amino acid sequence (SEQ ID NO:69), as well as the sequences of the four amplimers used for its synthesis (SEQ ID NOS:37–40).

FIG. 4B is a representation of the nucleotide sequence of the cDNA of new chemokine-like protein IL-8M1 (SEQ ID NO:70) and the translated amino acid sequence, as well as the sequences of the two amplimers used for its synthesis (SEQ ID NOS:40 and 42).

FIG. 4C is a representation of the nucleotide sequence of the cDNA of the IL-8 polypeptide antagonist IL-8M8 (SEQ ID NO:52) and its translated amino acid sequence (SEQ ID NO:63), as well as the two amplimers used for its synthesis (SEQ ID NOS:40 and 53).

FIG. 4D is a representation of the nucleotide sequence of the CDNA of the IL-8 polypeptide antagonist IL-8M9 (SEQ ID NO:54) and its translated amino acid sequence (SEQ ID NO:64), as well as the two amplimers used for its synthesis (SEQ ID NOS:40 and 55).

FIG. 4E is a representation of the nucleotide sequence of the cDNA of the IL-8 polypeptide antagonist IL-8M10 (SEQ ID NO:50) and its translated amino acid sequence (SEQ ID NO:65), as well as the two amplimers used for its synthesis (SEQ ID NOS:40 and 51).

FIG. 4F is a representation of the nucleotide sequence encoding IL-8M3 (SEQ ID NO:56).

DETAILED DESCRIPTION

Figure 5:
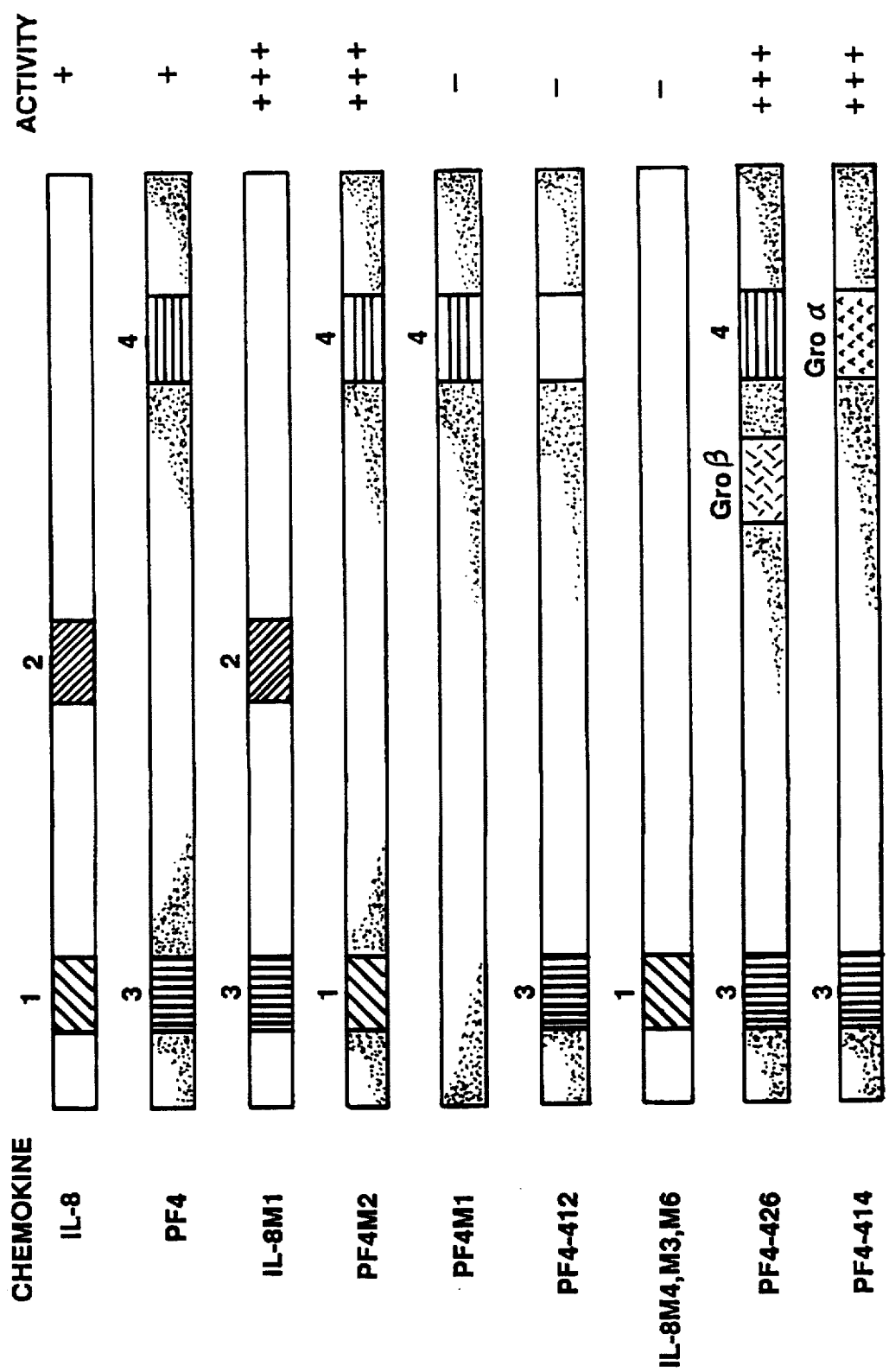
FIG. 5 is a schematic of the chemokine active domains necessary for myelosuppression and their locations in wild-type IL-8 and PF4, and in new chemokine-like proteins.

A series of new chemokine-like proteins were made using wild-type amino acid sequences of known chemokines as templates, and including at least two active domains, with at least one of the new active domains originating from a chemokine other than the template chemokine. Other new proteins that included only one active domain were used as controls. These new chemokine-like proteins were then tested for myelosuppressive activity in in vitro assays and in in vivo animal models described below. In addition, several of these new proteins were found not to activate neutrophils, and thus are not inflammatory.

The amino acid sequences of the new chemokine-like proteins are shown in FIG. 2, in which the bold amino acids represent active domains that have been discovered to be required for the myelosuppressive activity of the wild-type chemokines and new chemokine-like proteins. Underlined amino acids are different from those normally found at that location in the wild-type chemokine template. Variations of these new chemokine-like proteins can be made and tested as described below.

Chemokines

Chemokines having normal, wild-type amino acid sequences are available in natural or recombinant form. For example, natural PF4 can be isolated from human platelet extracts. Natural IL-8 has been isolated from either stimulated human endothelial cells or human monocytes. Other chemokines such as PBP or βTG can be isolated from various human cell sources. The wild-type amino acid sequences of several representative members of the human chemokine family are shown in FIG. 1. As used herein, the term "chemokine" or "wild-type chemokine" includes both the natural and recombinant forms of the proteins that have a wild-type amino acid sequence.

Recombinant MIP-1α (rMIP-1α), rMIP-1β, rMIP-2α, and rMIP-2β are produced using yeast expression vectors as described in Tekamp-Olson et al., J. Exp. Med., 172:911 (1990), or can be obtained from Peprotech (Rocky Hills, N.J.). Recombinant IL-8 (rIL-8), PF4 (rPF4), NAP-2 (rNAP-2), CTAP-III (rCTAP-III), GROα (rGRO-α), and GROβ (rGROβ) were cloned and expressed in E. coli at Repligen (Cambridge, Mass.). Both the 77- and 72-amino acid forms of IL-8 were cloned and expressed at Repligen, and can be purchased from Pepro Tech, Rocky Hills, N.J. The 77-amino acid form of rIL-8 and the natural form of PF4 can also be purchased from Sigma Chemical Co. (St. Louis, Mo.). Recombinant preparations of IL-8, MCAF and RANTES are available from PeproTech (Rocky Hills, N.J.). Recombinant NAP-2 (rNAP-2) can be purchased from Bachem Bioscience, Philadelphia, Pa. Other cytokines, including recombinant EPO (rEPO) can be purchased from Amgen Corporation (Thousand Oaks, Calif.). Human rGM-CSF, rGROα, IL-3, and SLF (also called mast cell growth factor, stem cell factor, and c-kit ligand) can be obtained from Immunex Corporation (Seattle, Wash.).

Human chemokines were purified prior to use and no endotoxin was detected in these samples using a standard limulus lysate assay.

Human Bone Narrow Progenitor Cells

Human bone marrow cells were obtained by aspiration from the posterior iliac crest of healthy volunteers. Low density (LD) cells (<1.077 g/cm$^3$) were retrieved after density cut separation on FICOLL-HYPAQUE™ (Pharmacia Fine Chemicals, Piscataway, N.J.).

Methods of Making Chemokine-Like Proteins

New chemokine-like proteins can be made using standard synthetic techniques, or can be generated using recombinant DNA technology and expressed in bacterial, yeast, or mammalian cells using standard techniques.

Chemical Synthesis

Chemokine-like proteins can be synthesized based on the amino acid sequences described herein and variations thereof by standard solid-phase methods using the tert-butyloxy-carbonyl and benzyl protection strategy described in Clark-Lewis et al., P.N.A.S. USA, 90:3574–3577 (1993) and Clark-Lewis et al., Biochemistry, 30:3128–3135 (1991). After deprotection with hydrogen fluoride, the proteins are folded by air oxidation and purified by reverse-phase HPLC. Purity is determined by reverse-phase HPLC and isoelectric focusing. Amino acid incorporation is monitored during synthesis, and the final composition is determined by amino acid analysis. The correct covalent structure of the protein can be confirmed using ion-spray mass spectrometry (SCIEX APIII).

Recombinant Expression of Chemokine-Like Proteins

New chemokine-like proteins can also be generated using recombinant DNA techniques. For example, mutant chemokine genes were generated using standard polymerase chain reaction (PCR) amplification of synthetic oligonucleotide primers, e.g., as described in Mullis et al., U.S. Pat. No. 4,800,159. The primers were designed to be less than 100 bases in length with a minimal overlap of at least 25 bases, and were synthesized using an Applied Biosystems 394

DNA/RNA synthesizer. A large (10 to 40 base) region upstream of a restriction site was included to facilitate restriction endonuclease digestion and to enhance visualization of endonuclease digested DNA versus undigested DNA on an agarose gel. Oligonucleotide primers were amplified by 25 to 30 cycles of PCR using standard reaction conditions. Outside primer concentration was 0.4 pmoles/µl and all inside primer concentrations were 0.004 pmoles/µl in the reaction. Following amplification, the selected gene was digested with restriction endonucleases Bam HI and Nde I and electrophoresed on a 1% LMP agarose/3% NuSieve gel containing 40 mM Tris, acetate, 2 mM $Na_2EDTA.2H_2O$ (TAE) buffer. Bands corresponding to the doubly cut gene were excised from the gel and used in ligation reactions.

The digested DNA was ligated into the pMEK vector (derivatized pET 9a vector, Novagen, Madison, Wis.) and was selected for by kanamycin resistance. This vector permits protein expression only following induction of the cells with isopropyl-β-D-thiogalactoside (IPTG). Following the ligation reaction, the vector including the gene segment was electroporated into XL1 Blue E. coli cells and screened on agar-kanamycin plates. Colonies were chosen and the correct inserts were screened by restriction digests of DNA mini-preps (5 colonies per plate). The DNA sequences of positive clones were confirmed using an Applied Biosystems Prism Taq Dye Deoxy Terminator sequencing kit and an Applied Biosystems 373A DNA sequencer.

Following sequence confirmation, the resulting plasmids were electroporated into BL21 (DE3) E. coli cells. Colonies were screened on kanamycin plates and grown in 50 ml cultures for examination of expression levels following induction with IPTG.

Platelet Factor 4 (PF4)

The following general methods were used to synthesize, clone, and express a PF4 gene. First, the gene for PF4 was obtained by directing the bacterial expression of the protein. As shown in FIG. 3A (SEQ ID NO:29, /=signal peptide cleavage site), four partially complementary oligonucleotides (amplimers) were synthesized (PF4-1 to PF4-4). Amplimer PF4-1 (SEQ ID NO:30) was a 99 mer and included an Nde I restriction site, the ATG translation start codon, and sense strand nucleotides 101 to 157 of the published human PF4 cDNA (Poncz et al., Blood, 69:219–223 (1987)) [codons $Glu_{32}$ to $Val_{50}$ of the precursor ($Glu_1$ to $Val_{19}$ of the mature secreted form)]. PF4-2 (SEQ ID NO:31), also a 99 mer, contained the antisense nucleotides 231 to 133, extending to the first two positions of codon $Thr_{75}$ of the precursor ($Thr_{44}$ of the secreted form), with the 3' 25 nucleotides being complementary to the 3' 25 nucleotides of PF4-1. PF4-3 (SEQ ID NO:32), also a 99 mer, contained sense nucleotides 205 to 303, extending to the coding strand sequence of $Leu_{99}$ of the precursor ($Leu_{68}$ of the mature secreted form), with positions 1 through 27 being complementary to positions 1 though 27 of PF4-2. PF4-4 (SEQ ID NO:33), a 70 mer, contained antisense nucleotides 313 to 274, extending to the $TAG_{102}$ translation stop of the precursor ($TAG_{71}$ of the mature secreted form), and contained additional nucleotides for restriction sites for cloning.

The sequence of these amplimers were such that the final double-stranded DNA fragment would encode the amino acid sequence of human PF4 as shown in FIG. 3A (SEQ ID NO:29).

The four amplimers were annealed to create a gapped PF4 gene, and PCR amplification was then used to fill in the gaps and amplify the full-length gene so that it could be cloned into an expression vector for production of the protein. The four amplimers were mixed at final concentrations of 5 µM of PF4-1, 0.05 µM of PF4-2, 0.05 µM of PF4-3, and 5 µM of PF4-4. This mixture was diluted 6.25-fold and amplified using Pfu polymerase (Stratagene, La Jolla, Calif.) per the manufacturer's conditions without adding any template in addition to the amplimer mixture. The reaction was subjected to 35 cycles of amplification at 98° C. for 1 minute, 50° C. for 1 minute, and 72° C. for 3 minutes. The success of the amplification was verified by agarose gel electrophoresis of a portion of the PCR reaction mixture.

The amplified PF4 DNA fragment was purified and concentrated from the remainder of the reaction using a Quiagen PCR Purification kit (Quiagen, Inc., Chatsworth, Calif.). One half of the purified PF4 DNA fragment was digested with 60 units each of the restriction enzymes NdeI and BamHI in a 50 µl reaction volume. The digested fragment was purified by low melting point agarose gel electrophoresis and ligated with gel purified NdeI/BamHI-digested pET3a (Novagen, Madison, Wis.) to create the E. coli expression plasmid pETPF4-1. The pET3a backbone was derived from the plasmid pARVH which consisted of the pET3a vector with an MGSA/Gro-related sequence cloned in the NdeI to BamHI restriction site. This plasmid was digested with NdeI and BamHI to remove the MGSA/Gro fragment so that the PF4 fragment could be inserted. The PF4 DNA fragment insert of the resulting pETPF4-1 plasmid was sequenced in its entirety, which confirmed that the correct sequence was present.

For initial expression, the plasmid pETPF4-1 was used to transform E. coli strain BL21. The transformants were grown to an OD of 1.2, and then induced to express the PF4 gene by the addition of 0.4 mM IPTG to the culture medium. After 2 hours, the cells were pelleted, and a small portion was examined by SDS-PAGE and Western blotting to confirm expression of PF4.

Interleukin-8

The gene for IL-8 was synthesized in a similar fashion except that the oligonucleotide amplimers were made such that the final sequence would encode the IL-8 amino acids (SEQ ID NO:69) as in FIG. 4A (SEQ ID NO:36). Amplimer IL-8-1 (SEQ ID NO:37) was a 99 mer and included an NdeI restriction site, the ATG translation start codon, and sense strand nucleotides 1–59 of the human IL-8 cDNA. IL-8-2 (SEQ ID NO:38) was a 99 mer and included antisense nucleotides 42 to 140 of the human IL-8 cDNA. IL-8-3 (SEQ ID NO:39), also a 99 mer, included sense strand nucleotides 109 to 207. IL-8-4 (SEQ ID NO:40), was a 70 mer, and included anti-sense strand nucleotides 183 to 219 of the IL-8 cDNA extending to the TAG translation stop of the gene and an additional stretch of nucleotides for restriction sites for cloning.

Purification

The synthetic genes for human PF4, IL-8, and new chemokine-like proteins were expressed in E. coli (BL21) cells and grown in 10 liter containers. Cells were grown for 4 hours at 37° C. followed by induction with IPTG (0.4 mM) overnight. Approximately 550 g of cell paste containing inclusion bodies was obtained, of which 100 g was suspended in lysis buffer (0.05M Tris-HCl, pH 8.0, 5 mM EDTA, 5 mM DTT, 0.1% Triton-X100) and lysed by DYNOMIL™ disruption in the presence of 0.1% α-toluenesulfonylfluoride (PMSF). The lysed preparation was treated with two aliquots of DNase I, concomitantly added with $MgCl_2$ and incubated for 0.5 hours at 4° C.

Following DNase I treatment, the suspension was centrifuged overnight at 4° C. at 13,000 rpm. The precipitate from the centrifugation step was extracted in 150 mls of 0.05M Tris-HCl, pH 8.0, 6M Guanidine-HCl, and 50 mM DTT overnight at 25° C. The extracted material was dialyzed against buffer containing 25 mM sodium acetate, pH 4.0, 8M urea, and 50 mM DTT and loaded onto a S-Sepharose column equilibrated with 25 mM sodium acetate, pH 4.0, 8M urea. The column, containing bound protein, was washed with 25 mm sodium acetate, pH 4.0, to remove the urea followed by a second buffer wash containing 25 mM sodium acetate, pH 4.0, 0.5M NaCl. The protein was then eluted with buffer containing 50 mM Tris-HCl, pH 8.0, 1M NaCl.

Fractions containing the appropriate chemokine or chemokine-like protein were refolded by overnight incubation in the presence of 1 mM oxidized/2 mM reduced glutathione at 25° C. The extent of refolding of the proteins was monitored using POROS™ analytical chromatography. The reduced protein species were observed to elute from the POROS™ column at different acetonitrile concentrations relative to the refolded species. Refolded fractions were pooled and rechromatographed by C4 semi-preparative reverse phase HPLC using a 0 to 100% acetonitrile gradient in 0.1% TFA:$H_2O$. Peak fractions were pooled and lyophilized for concentration determination.

Purity of the final proteins was assessed by Coomassie staining of SDS PAGE, analytical C4 reverse phase HPLC, and amino acid analysis. Protein concentrations were determined by amino acid analysis and an bicinchoninic acid (BCA) assay described by Smith et al., *Anal. Biochem.*, 150:76–85 (1985). Typically, several hundred milligrams of >95% pure material was isolated from 100 g of starting material.

For small scale purifications, cells were grown in a 500 ml shaker flask containing 300 µg/ml kanamycin until an absorbance of 0.6 at 600 nm was reached. Cells were then induced with IPTG for 3 hours at 37° C. followed by centrifugation at 14,000 x g for 30 minutes. The cell paste was resuspended in 20 ml of 1X phosphate buffered saline (PBS, Gibco) and sonicated for 3 minutes at 4° C. using a Braun-Sonic model 1510 sonicator at 200 W. The lysed material was centrifuged for 30 minutes at 13,000 x g, and the precipitated material was resuspended in buffer containing 6M Guanidine-HCl as described above. Small scale purification of chemokine proteins was identical to the purification described above for the large scale isolation of chemokines.

Determination of Protein Concentration

Protein concentrations were determined using the BCA protein assay described above and results were calculated based on concentrations obtained from a standard dilution series of bovine serum albumin. Amino acid analysis of chemokines was obtained following hydrolysis of the proteins for 24 hours at 90° C. in 12M HCl. Following hydrolysis, samples were derivatized and analyzed according to the method of Bidlingmeyer et al., *J. Chromatography*, 336:93–104 (1984).

Specific Chemokine-Like Proteins

The genes that express the new chemokine-like proteins can be made by either of two methods. In the first method, a wild-type chemokine gene, e.g., one of the IL-8 or PF4 genes described above, is used as a template, and the desired amino acid substitutions are made in this amino acid template by PCR amplification using, e.g., a sense 5' amplimer that contains the sequence for the desired modified codon(s). This results in the amplification of a new gene that encodes a new protein with the desired amino acid sequence.

Alternatively, genes encoding the new chemokine-like proteins can be synthesized without a template using the four overlapping amplimer strategy described above with amplimers containing appropriate sequence changes such that the final amplified DNA fragment will encode the desired amino acid sequence in the expressed new chemokine-like protein.

A variety of new chemokine-like proteins were made using the wild-type amino acid sequences of human PF4 and IL-8 (FIGS. 3A and 4A, respectively) as the template. As shown in FIG. 2, these new proteins are similar in amino acid sequence to certain wild-type chemokines, in this case IL-8 or PF4, but include specific amino acid substitutions and/or insertions that make these new proteins distinct and unique compared to the wild-type chemokines. In addition, these substitutions provide the new chemokine-like proteins with an unexpected enhanced myelosuppressive activity.

In particular, as shown in FIG. 4B, the cDNA (SEQ ID NO:41) encoding new protein IL-8M1 (SEQ ID NO:70) was synthesized using a 5' sense amplimer IL-8M1-1 (SEQ ID NO:42), which contains a nucleotide mutation designed to result in the substitution of the amino acid sequence DLQ (an active domain from PF4) for the sequence ELR in wild-type IL-8 in the amino terminus of the protein. Because the remainder of the IL-8M1 sequence was to be the same as the wild-type IL-8 sequence, the 3' antisense amplimer used was the same one used in the synthesis of the CDNA encoding wild-type IL-8 described above, amplimer IL-8-4 (SEQ ID NO:40). This amplimer was chosen because no other mutation was desired, and this amplimer will produce no further mutation in the wild-type IL-8 sequence.

The cDNA (SEQ ID NO:50) encoding the new protein IL-8M8 (SEQ ID NO:52) was synthesized as described above, except that the primer IL-M8-1 (SEQ ID NO:63) was used as the 5' amplimer. As shown in FIG. 4C, the IL-8M8-8 (SEQ ID NO:52) amplimer contains a nucleotide mutation designed to result in the substitution of the amino acid sequence $E_4L_5Q_6$ for the sequence $E_4L_5R_6$ in the N-terminus of wild-type IL-8. Because the remainder of the IL-8M8 sequence was to be the same as the wild-type IL-8 sequence, the 3' antisense amplimer used was the same one used in the synthesis of the cDNA encoding wild-type IL-8 described above, amplimer IL-8-4 (SEQ ID NO:40).

The cDNA (SEQ ID NO:54) encoding the new protein IL-8M9 (SEQ ID NO:64) was synthesized as described above, except that the primer IL-8M9-1 (SEQ ID NO:55) was used as the 5' amplimer. As shown in FIG. 4D, the IL-8M9-1 (SEQ ID NO:55) amplimer contains a nucleotide mutation designed to result in the substitution of the amino acid sequence $D_4L_5R_6$ for the sequence $E_4L_5R_6$ in the N-terminus of wild-type IL-8. Because the remainder of the IL-8M9 sequence was to be the same as the wild-type IL-8 sequence, the 3' antisense amplimer used was the same one used in the synthesis of the cDNA encoding wild-type IL-8 described above, amplimer IL-8-4 (SEQ ID NO:40).

The CDNA (SEQ ID NO:50) encoding the new protein IL-8M10 (SEQ ID NO65) was synthesized as described above, except that the primer IL-8M10-1 (SEQ ID NO:51) was used as the 5' amplimer. As shown in FIG. 4E, the IL-8M10-1 (SEQ ID NO:51) amplimer contains a nucleotide mutation designed to result in the substitution of the amino acid sequence $D_4L_5N_6$ for the sequence $E_4L_5R_6$ in the N-terminus of wild-type IL-8. Because the remainder of the IL-8M10 sequence was to be the same as the wild-type IL-8 sequence, the 3' antisense amplimer used was the same one used in the synthesis of the cDNA encoding wild-type IL-8 described above, amplimer IL-8-4 (SEQ ID NO:40).

The cDNA encoding IL-8M3 (SEQ ID NO:56) was synthesized in a manner similar to that described above for IL-8M1, IL-8M8, IL-8M9, and IL-8M10, except that the PCR amplification was designed to insert the amino acid sequence $E_{24}Y_{25}R_{26}R_{27}$ for the wild-type IL-8 sequence $E_{24}L_{25}R_{26}V_{27}$. The nucleotide sequence encoding IL-8M3 (SEQ ID NO:56) is shown in FIG. 4F.

As shown in FIG. 3B, the cDNA (SEQ ID NO:34) encoding new protein PF4M2 (SEQ ID NO:67) was synthesized using a 5' sense amplimer PF4M2-1 (SEQ ID NO:35), which contains a nucleotide mutation designed to result in the substitution of the amino acid sequence MSAKELRCQC (SEQ ID NO:45) for the sequence EAEEDGDLQCLQ (SEQ ID NO:46) in wild-type PF4 in the amino terminus of the protein. The second amplimer used was the same one used in the synthesis of the cDNA encoding wild-type PF4 described above, the 3' antisense amplimer PF4-4 (SEQ ID NO:33).

The chemokines PF4-414 and PF4-426 were synthesized using a similar techniques. The synthesis of PF4-414 is illustrated in FIG. 3C, using the amplimers for wild-type PF4 and substitution the amplimer PF414-1 (SEQ ID NO:58) for the antisense 3' amplimer. The synthesis of PF4-426 (SEQ ID NO:68) is illustrated in FIG. 3D using amplimers PF4-426-1 (SEQ ID NO:60), PF4-426-2 (SEQ ID NO:61), PF4-426-3 (SEQ ID NO:62), and the amplimer PF4-4 (SEQ ID NO:33).

Based on the methods, techniques, and assay results described herein, additional new proteins can be created using other wild-type chemokines as the template or structural basis. As described below and shown schematically in FIG. 5, the amino acid changes in a template based on a first wild-type chemokine must introduce at least one new myelosuppressive active domain from one region of a second wild-type chemokine into the template, while maintaining a myelosuppressive active domain of the first chemokine in another region of the template or introducing another active domain from the second or a third wild-type chemokine.

FIG. 5 shows that wild-type IL-8, having active domains 1 (ELR of IL-8) and 2 (ELRV of IL-8), provides a normal level of myelosuppressive activity. Wild-type PF4, having active domains 3 (the first DLQ of PF4) and 4 (the second DLQ of PF4), also provides a normal level of myelosuppressive activity. If either of these active domains are removed, the resulting protein loses its myelosuppressive activity. For example, PF4M1, which is missing domain 3; PF4-412, which is missing domain 4; and IL-8M4, M3, and M6, which are all missing domain 2; all lack myelosuppressive activity. On the other hand, new chemokine-like protein PF4M2 includes active domains 1 and 4, and has unexpectedly high myelosuppressive activity. Similarly, IL-8M1 includes domains 3 and 2, and has unexpectedly high myelosuppressive activity.

Examples of new chemokine-like proteins based on PF4 include PF4M1 and PF4M2. Testing of PF4M1 showed that destroying an active domain found in PF4 also destroys PF4's myelosuppressive activity. PF4M1 was generated by creating a point mutation in the N-terminal end of wild-type PF4 that changed the amino acids $D_7L_8Q_9$ (PF4's first active domain) proximal to and on the N-terminus side of the first cysteine to the amino acids DLR. As shown by the assay results described below, this change destroyed PF4's first active domain and resulted in a protein without myelosuppressive activity.

Testing of PF4M2 showed that replacing an active domain in PF4 with an active domain from a second chemokine creates a new highly myelosuppressive protein. PF4M2 was generated by replacing the entire N-terminus up to the first cysteine of wild-type PF4 with the corresponding N-terminus of wild-type IL-8. This change replaced PF4's first active domain with IL-8's first active domain ($E_4L_5R_6$) while maintaining PF4's second active domain ($D_{54}L_{55}Q_{56}$), and resulted in a highly active new protein.

New proteins PF4-412, PF4-413, and PF4-414 were generated by replacing amino acids 51 to 61 of wild-type PF4 with the corresponding amino acids from wild-type IL-8, NAP-2, or GROα, respectively. Of these new proteins, PF4-412 and PF4-413 were essentially inactive, because the substitution of the new domains from IL-8 and NAP-2 destroyed PF4's second active domain without introducing a new active domain. PF4-414 retained the first active domain of PF4 and included an active domain from GROα, and had a higher activity than wild-type PF4.

PF4-421 was generated from an exchange of amino acids 25 to 31 of wild-type PF4 with the corresponding amino acids from wild-type IL-8. This resulted in a new protein that maintained PF4's two active domains and introduced IL-8's second active domain ($E_{24}L_{25}R_{26}V_{27}$). This protein had about the same activity as wild-type PF4.

PF4-426 was created by replacing all three Arg (R) residues of wild-type PF4 with Glu residues (Q) to achieve a novel region at amino acids 42 to 50. These changes created a region in the new protein equivalent to a corresponding region in GROβ that includes an active domain, while maintaining the first active domain of PF4. As a result, PF4-426 was highly active.

Examples of new chemokine-like proteins based on IL-8 include IL-8M1, IL-8M3, IL-8M4, IL-8M6, IL-8M7, IL-8M8, IL-8M9, IL-8M10, and IL-8M64. IL-8M1 was generated by replacing the amino acids ELR proximal and on the N-terminus side of the first cysteine of normal IL-8 (IL-8's first active domain) with the amino acids DLQ from the corresponding location in wild-type PF4. Thus, this new protein included PF4's first active domain and IL-8's second active domain and was highly active.

IL-8M3, IL-8M4, and IL-8M6 were generated by creating one or two point mutations within the IL-8 dimer interface (IL-8's second active domain including the amino acids ELRV between the second and third cysteines in normal IL-8). These mutations destroyed IL-8's second active domain and, as expected, resulted in inactive proteins.

IL-8M7 was generated by replacing the entire C-terminus after the fourth cysteine of normal IL-8 with the corresponding C-terminus of normal PF4. This substitution resulted in a new protein having IL-8's first and second active domains and PF4's second active domain, and had about the same activity as wild-type IL-8.

IL-8M8, IL-8M9, and IL-8M10 were generated by creating one or two point mutations within the DNA encoding the amino acids ELR proximal and on the N-terminus side of the first cysteine of normal IL-8 (IL-8's first active domain). The IL-8M10 protein ($D_4L_5N_6$) exhibited myelosuppressive activity that was significantly enhanced relative to wild-type IL-8 activity, and comparable to the myelosuppressvie activity of IL-8M1. The mutations in IL-8M8 and IL-8M9 ($E_4L_5Q_6$ and $D_4L_5R_6$, respectively) resulted in proteins having myelosuppressive activities comparable to that of IL-8 and PF-4, suggesting that the double mutation within IL-8 is critical to the enhancement of myelosuppressive activity. These results also indicate that the amino acid sequences DLN, DLQ, and ELQ can also serve as "active domains," and can, in combination with another active domain, confer myelosuppressive activity upon the novel chemokine-like protein.

IL-8M64 was generated by truncating the last eight amino acids from the C-terminus of normal IL-8, which resulted in a new protein with about the same activity as wild-type IL-8.

Testing of Specific New Chemokine-Like Proteins

The different chemokine-like proteins shown in FIG. 2 were tested in both in vitro and in vivo assays to demonstrate their ability to inhibit proliferation of progenitor cells. Wild-type PF4 and IL-8 by themselves were shown to inhibit stem cell proliferation at concentrations as low as 25 ng/ml, whereas the new chemokine-like proteins were shown to have equivalent myelosuppressive activity at much lower concentrations.

while those data marked with a "$^c$" represent a significant change from control, p<0.05. The in vitro results are also shown in the graphs of FIGS. 6A to 6G.

TABLE IA

| | Chemokine concentration (ng/ml) | | | | | | | |
|---|---|---|---|---|---|---|---|---|
| Chemokine | 100 | 50 | 25 | 10 | 1 | 0.1 | 0.01 | 0.001 |
| PF4 WT | $-41 \pm 3^b$ | $-40 \pm 2^b$ | $-25 \pm 7^b$ | $-10 \pm 6$ | $-3 \pm 2$ | | | |
| PF4M1 | $-9 \pm 10$ | $-5 \pm 6$ | $-2 \pm 2$ | $-6 \pm 1$ | | | | |
| PF4M2 | $-43 \pm 2^b$ | $-44 \pm 2^b$ | $-42 \pm 3^b$ | $-46 \pm 2^b$ | $-47 \pm 2^b$ | $-42 \pm 5^b$ | $-19 \pm 8^c$ | $-3 \pm 2$ |
| PF4-412 | $-6 \pm 4$ | $-3 \pm 3$ | $-1 \pm 1$ | | | | | |
| PF4-413 | $-19 \pm 10^c$ | $-14 \pm 16$ | $-8 \pm 8$ | $-2 \pm 1$ | $+1 \pm 1$ | | | |
| PF4-414 | $-45 \pm 1^b$ | $-44 \pm 1^b$ | $-44 \pm 2^b$ | $-43 \pm 2^b$ | $-42 \pm 5^b$ | $-43 \pm 1^b$ | $-34 \pm 8^b$ | $-3 \pm 3$ |
| PF4-421 | $-42 \pm 6^b$ | $-40 \pm 4^b$ | $-29 \pm 3^b$ | $-25 \pm 9^c$ | $-8 \pm 4$ | $+1 \pm 1$ | | |
| PF4-426 | $-45 \pm 3^b$ | $-44 \pm 4^b$ | $-45 \pm 1^b$ | $-46 \pm 1^b$ | $-45 \pm 3^b$ | $-44 \pm 4^b$ | $-40 \pm 3^b$ | $-20 \pm 1^c$ |
| IL-8WT | $-42 \pm 2^b$ | $-43 \pm 2^b$ | $-21 \pm 5^b$ | $-4 \pm 2$ | $-3 \pm 6$ | | | |
| IL-8M1 | $-43 \pm 4^b$ | $-43 \pm 4^b$ | $-44 \pm 1^b$ | $-46 \pm 2^b$ | $-46 \pm 2^b$ | $-46 \pm 2^b$ | $-40 \pm 1^b$ | $-25 \pm 4^b$ |
| IL-8M3 | $-8 \pm 3$ | $-4 \pm 3$ | $-1 \pm 2$ | $-7 \pm 2$ | | | | |
| IL-8M4 | $-1 \pm 2$ | $-1 \pm 2$ | | | | | | |
| IL-8M6 | $-2 \pm 2$ | $-1 \pm 2$ | $+1 \pm 1$ | | | | | |
| IL-8M7 | $-43 \pm 4^b$ | $-45 \pm 2^b$ | $-25 \pm 2^b$ | $-2 \pm 3$ | $0 \pm 2$ | | | |
| IL-8M64 | $-43 \pm 1^b$ | $-43 \pm 2^b$ | $-27 \pm 5^b$ | $-10 \pm 7$ | $-8 \pm 5$ | $-5 \pm 1$ | | |

New Chemokine-Like Proteins Inhibit Progenitor Cell Proliferation In Vitro

Chemokine-like proteins made as described herein can be tested by standard in vitro assays to determine whether they inhibit formation of colony and cluster formation of granulocyte macrophages (termed colony forming unit-granulocyte macrophages (CFU-GM)). Such assays are well known and representative assays are described in Gentile et al., U.S. Pat. Nos. 5,149,544 and 5,294,544. In these assays, bone marrow or spleen cells are stimulated with, e.g., CSF, in an in vitro culture system. The inhibitory activity of the new chemokine-like protein is measured as the amount it decreases the CSF-stimulated colony and cluster formation.

In particular, the new proteins described above were tested for inhibition of GM colony formation as follows. LD cells were plated at a density of $5\times10^5$ cells in 0.3% agar culture medium with 10% FBS (Hyclone, Logan, Utah) for assessment of CFU-GM. CFU-GM colonies (>40 cells/ group) were stimulated by human rGM-CSF (100 U/ml) in combination with human rSLF (50 ng/ml). All colonies were tested in the absence or presence of different concentrations of new chemokine-like proteins to examine potency of inhibition of proliferation.

Colonies were scored after 14 days incubation at lowered (5%) $O_2$ tension, and 5% $CO_2$ in a humidified environment in an ESPEC $N_2$-$O_2$-$CO_2$ incubator BNP-210 (Taoi ESPEC Corp., South Plainfield, N.J.). Three plates were scored per determination. The results are expressed in Table IA below as a mean percent change from control ±1 S.E.M. for the number of experiments shown in experiments in which the control number of colonies per $1\times10^5$ cells/ml ranged from 115±5 (mean±1 S.E.M.) to 382±10. The inhibition shown, while partial inhibition of the total colony formation, is 90 to 100% inhibition of the steel factor enhanced colony formation.

In Table IA, those data marked with a "$^b$" represent a significant change from control, p<0.01 (Students t test), As shown in Table IA, wild-type PF4 and IL-8 were effective to inhibit colony formation by human bone marrow GM progenitor cells at concentrations of at least 25 ng/ml. At 10 ng/ml, neither one provided more than insignificant inhibition.

New chemokine-like protein PF4M1, in which the first active domain of PF4 was destroyed, was essentially inactive. PF4M2, however, which included the first active domain of wild-type IL-8 and the second active domain of wild-type PF4, had a much higher activity than wild-type PF4. Although PF4-412 and PF4-413 both retained PF4's first active domain, they were essentially inactive because they both lacked a second active domain. PF4-414, which retained PF4's two active domains and included a new active domain from GROα, had a higher activity than wild-type PF4. PF4-421, which retained PF4's two active domains and included the second active domain from wild-type IL-8, had a somewhat higher activity than wild-type PF4. PF4-426, which retained PF4's first active domain and included an active domain from wild-type GROβ, was highly active.

New chemokine-like protein IL-8M1, which included PF4's first active domain and IL-8's second active domain, was active down to 0.001 ng/ml. On the other hand, new proteins IL-8M3, IL-8M4, and IL-8M6 were essentially inactive, because each lacked an intact second active domain. IL-8M7, which included wild-type IL-8's first and second active domains and PF4's second active domain, had about the same activity as the wild-type IL-8. IL-8M64, which retained wild-type IL-8's first and second active sites, but which lacked the last 8 amino acids of wild-type IL-8, also had about the same activity as wild-type IL-8.

Figure 6A:
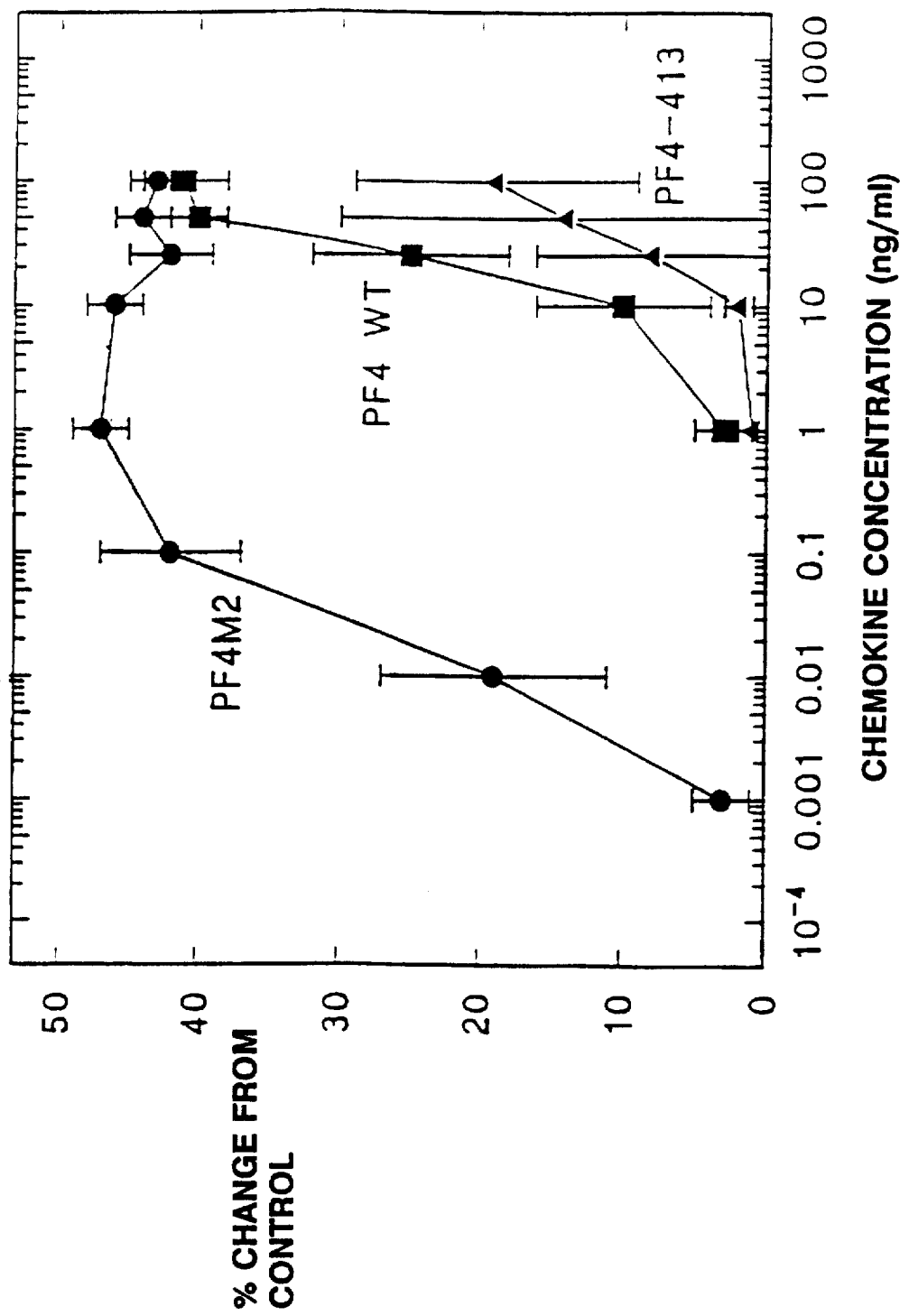
FIGS. 6A to 6H are graphs representing the inhibition of myeloid progenitor colony formation in in vitro assays of new chemokine-like proteins compared to wild-type PF4 and IL-8.
Figure 6B:
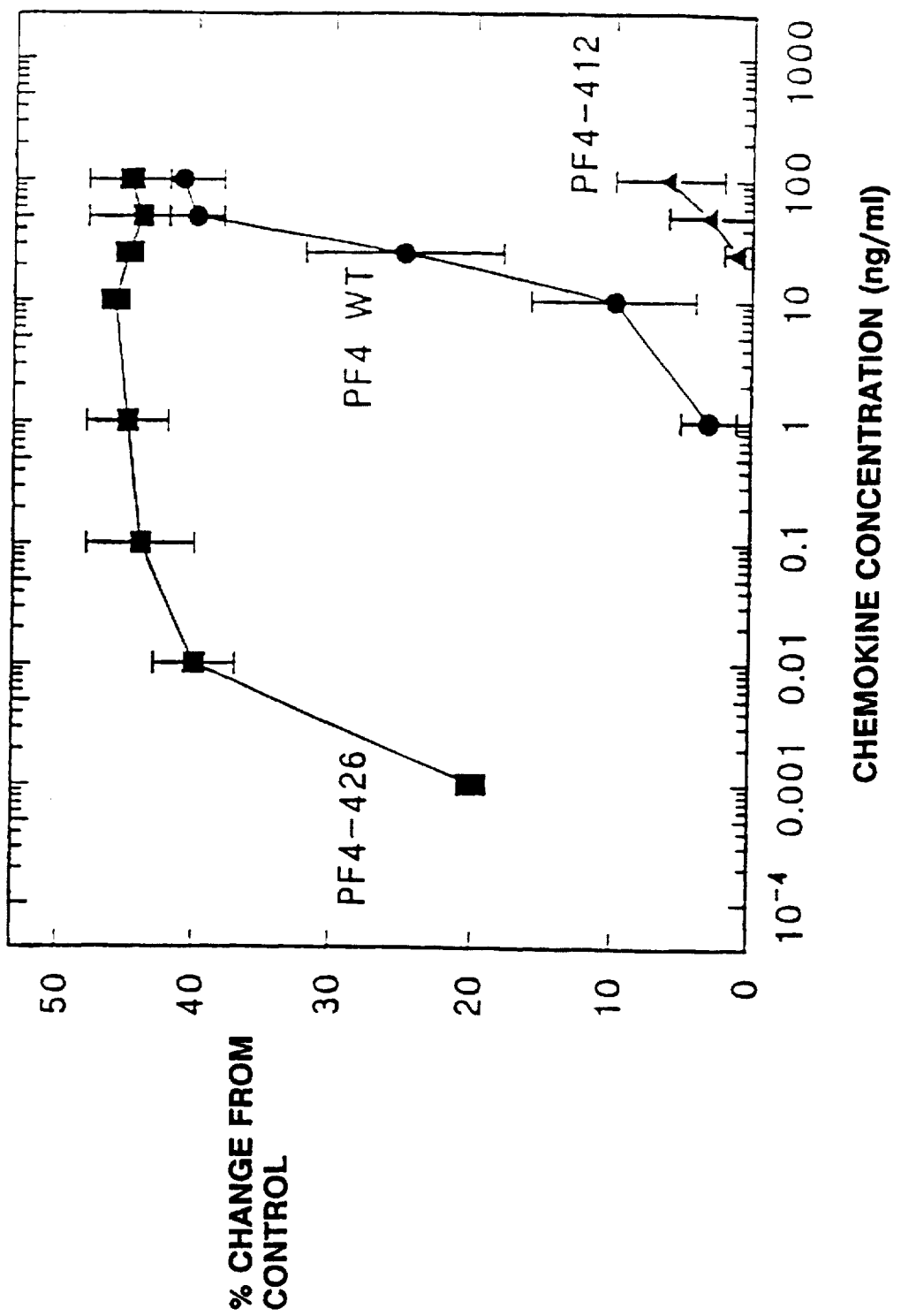
Figure 6C:
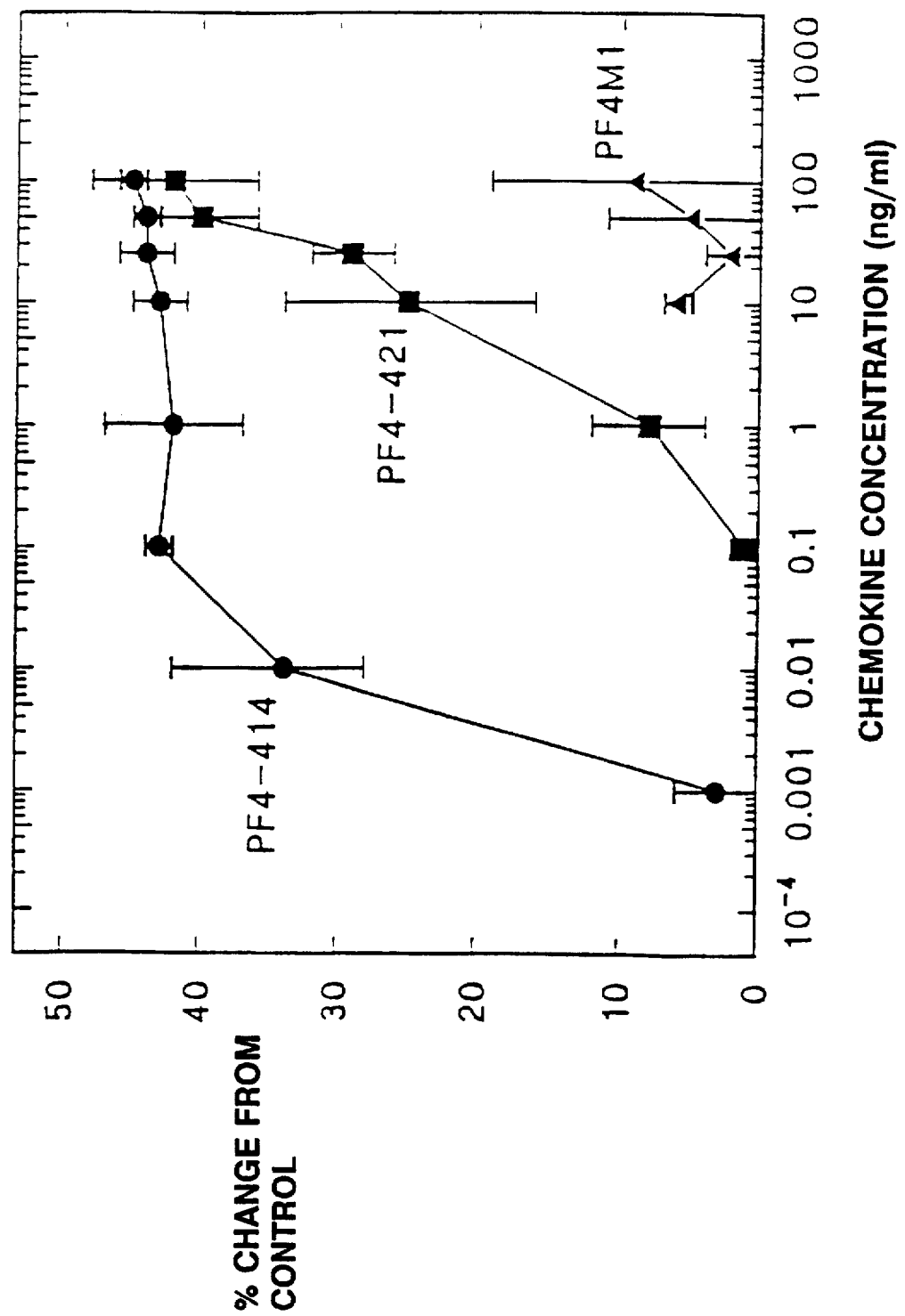
Figure 6D:
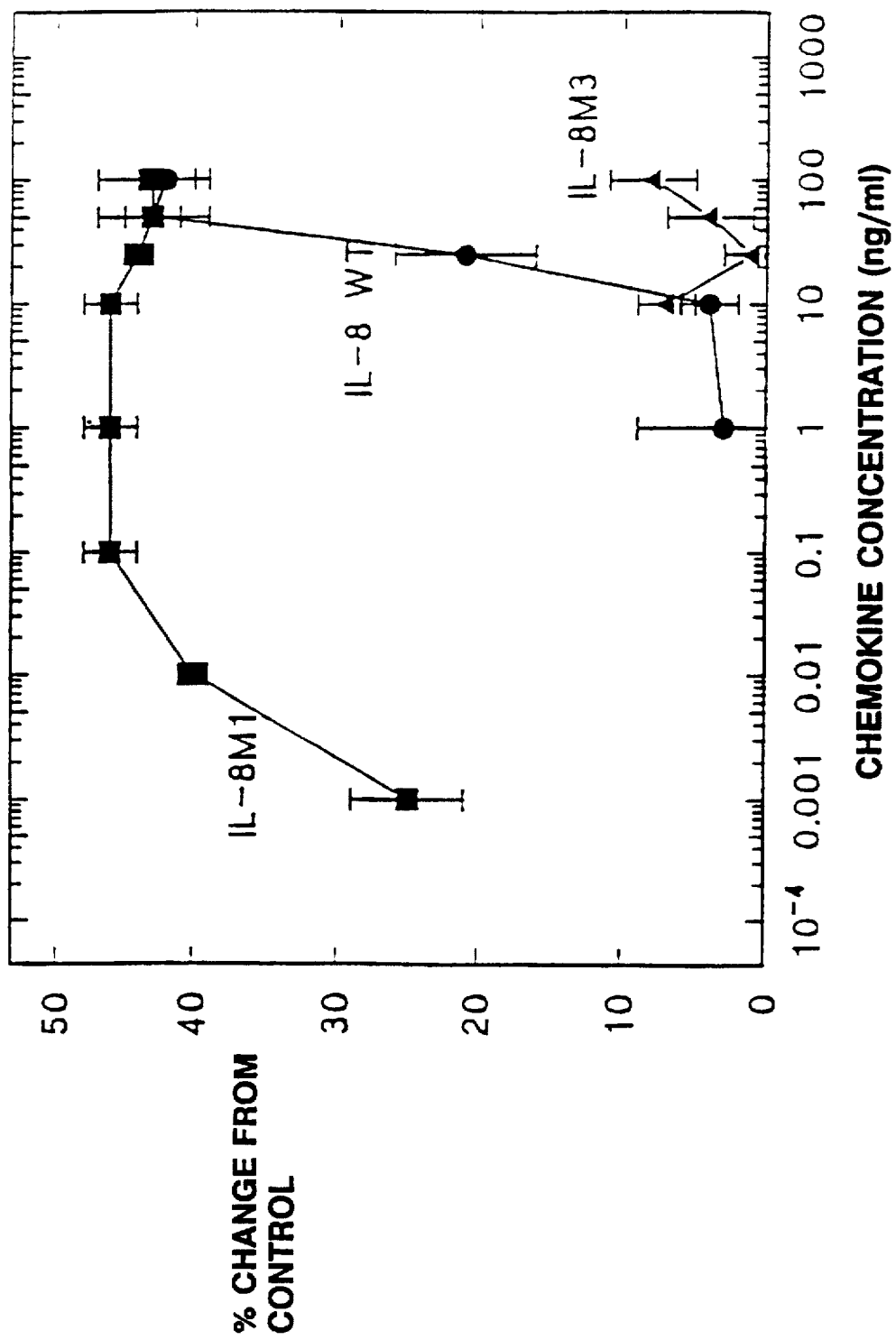
Figure 6E:
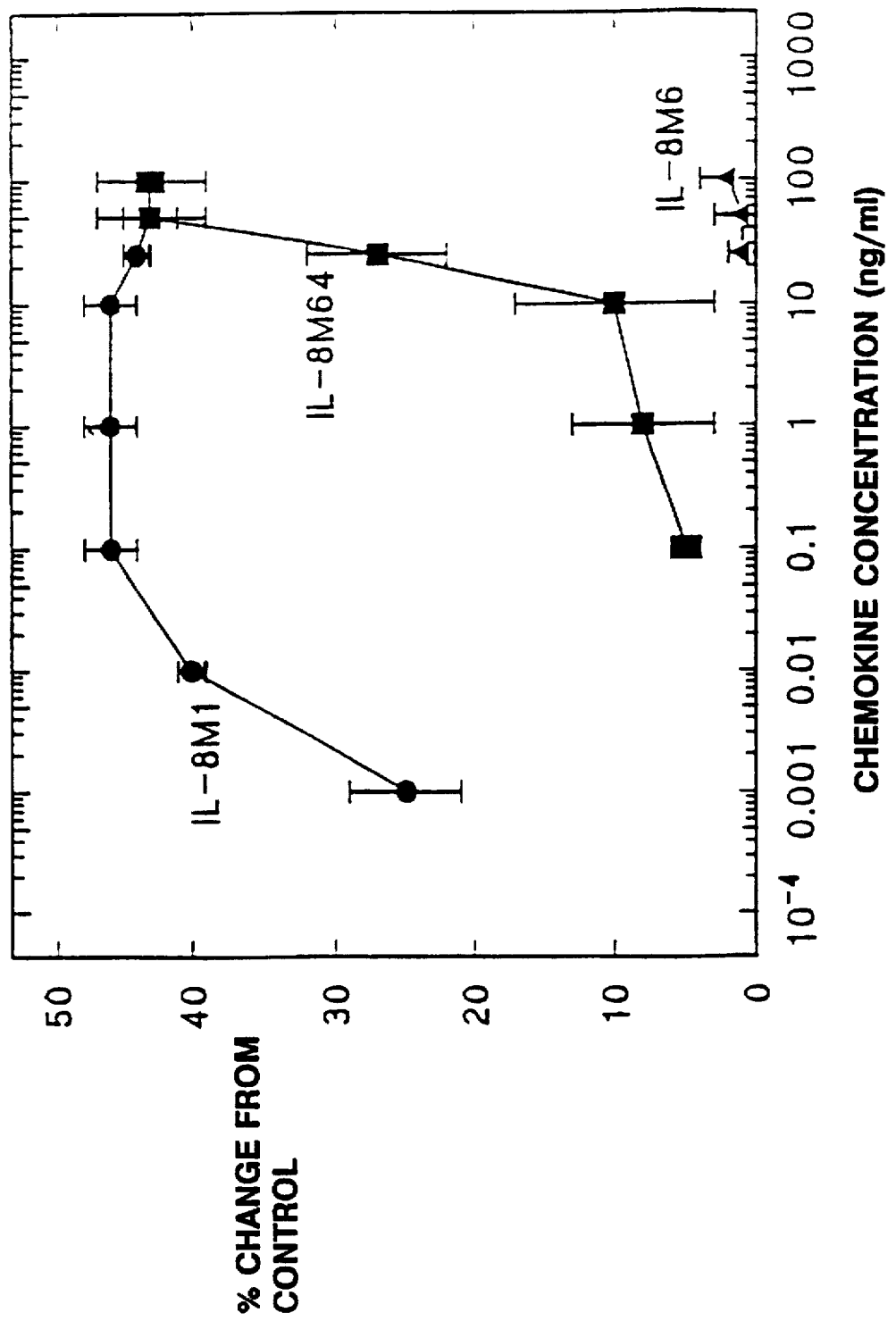
Figure 6F:
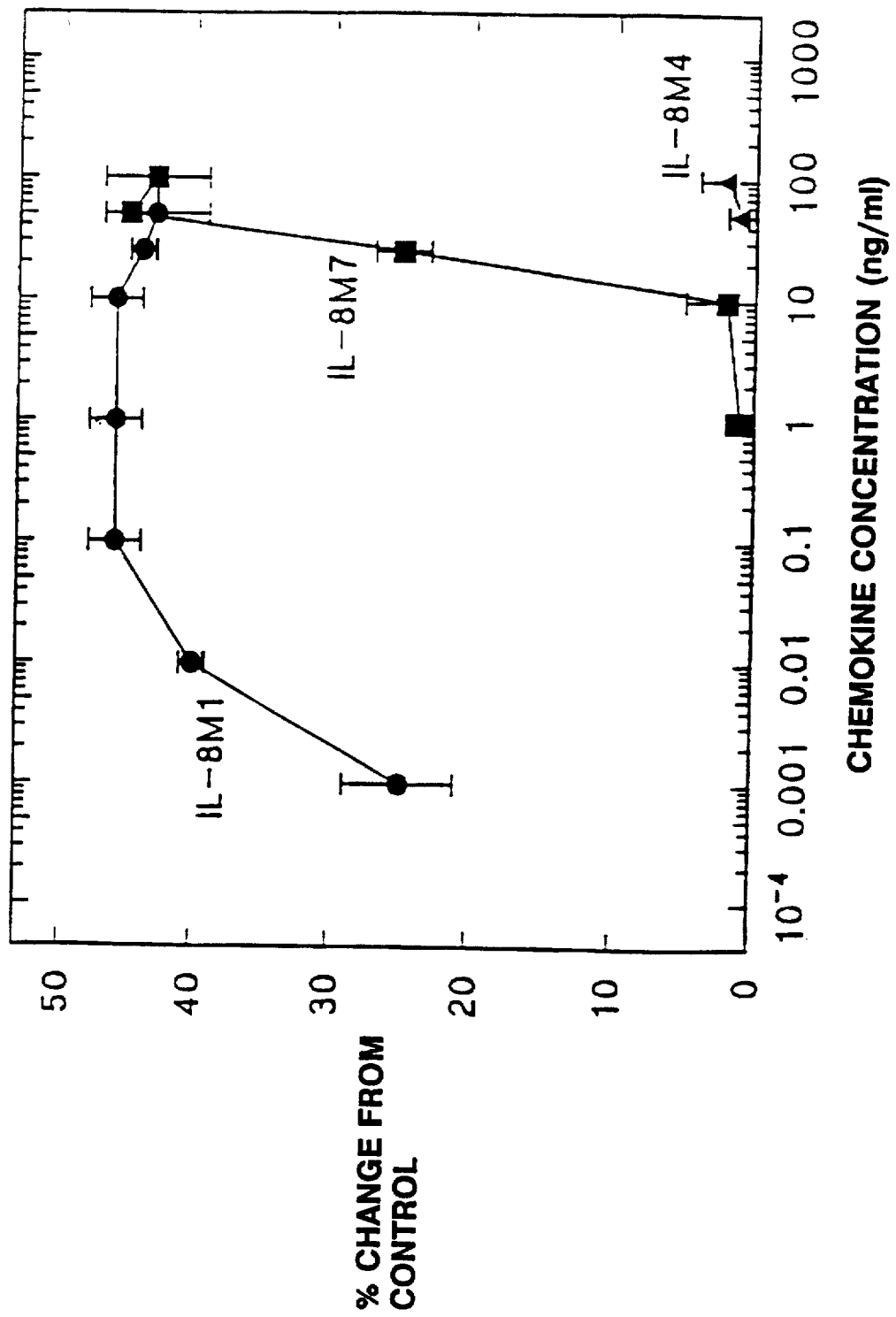
Figure 6G:
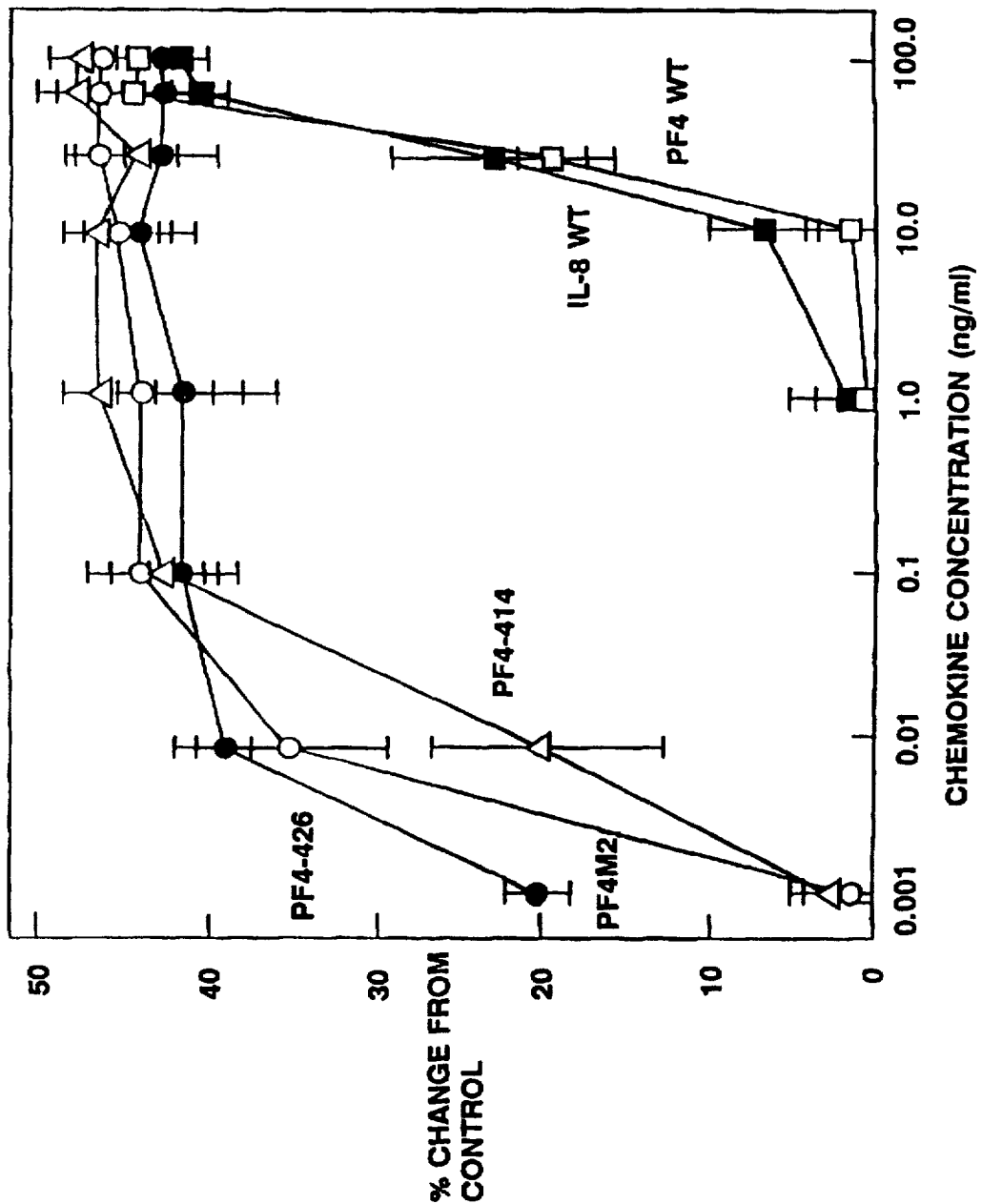

The data in Table IA are also represented in graphical form in FIGS. 6A to 6G. FIG. 6A shows the percent inhibition of myeloid progenitor colony formation by PF4M2 and PF4-413 compared to wild-type PF4 (PF4 WT). FIG. 6B shows the percent inhibition by PF4-426 and PF4-412 compared to PF4 WT. FIG. 6C shows the percent inhibition by PF4-414, PF4-421, and PF4M1. FIG. 6D shows the percent inhibition by IL-8M1 and IL-8M3 compared to IL-8 WT. FIG. 6E shows the percent inhibition by IL-8M1, IL-8M64, and IL-8M6. FIG. 6F shows the percent inhibition by IL-8M1, IL-8M7, and IL-8M4. FIG. 6G shows the percent inhibition by wild-type PF4, PF4-414, PF4-426, PF4M2, and wild-type IL-8. These graphs are all on the same scale, therefore, the activity of different new proteins can be directly compared.

The relative activities of IL-8M1, IL-8M8, IL-8M9, IL-8M10, wild-type IL-8, and wild-type PF4 in myelosuppression of colony formation by granulocyte macrophages (GM) (CFU-GM), erythroid cells (BFU-E), and multipotential cells (CFU-GEMM) were tested in an in vitro assay similar to the assay described above (Lord et al., *Blood*, between cell lineages. These data indicate that chemokine-dependent suppression is not cell lineage-specific, but rather affects multiple progenitor cell populations. IL-8M8 and IL-8M9 exhibited myelosuppressive activities comparable to the myelosuppressive activities of wild-type IL-8 and PF4 wild-type. IL-8M10 was highly active in myelosuppression, and had activity comparable to that of IL-8M1, suggesting that replacement of $Arg_6$ of wild-type IL-8 with either glutamine or asparagine can mediate enhanced myelosuppressive activity if aspartic acid is present at position 4 of the IL-8 wild-type sequence.

TABLE IB

| Chemokine | Chemokine Concentration (ng/ml) | | | | | | | | |
|---|---|---|---|---|---|---|---|---|---|
|  | 100 | 50 | 25 | 10 | 1 | 0.1 | 0.01 | 0.001 | 0.0001 |
| CFU-GM | | | | | | | | | |
| IL-8 WT | −48 ± 6[a] | −49 ± 5[a] | −26 ± 5[a] | −5 ± 3 | | | | | |
| PF4 WT | −48 ± 5[a] | −49 ± 6[a] | −34 ± 7[a] | −8 ± 4 | −3 ± 1 | | | | |
| IL-8M1 | −51 ± 4[a] | −51 ± 5[a] | −50 ± 5[a] | −49 ± 4[a] | −49 ± 5[a] | −47 ± 5[a] | −48 ± 3[a] | −28 ± 3[a] | −7 ± 3 |
| IL-8M8 | −53 ± 4[a] | −51 ± 4[a] | −34 ± 5[a] | −18 ± 8[b] | −13 ± 8 | −4 ± 2 | | | |
| IL-8M9 | −52 ± 4[a] | −50 ± 4[a] | −32 ± 7[a] | −17 ± 10 | −16 ± 8 | −3 ± 2 | | | |
| IL-8M10 | −54 ± 4[a] | −52 ± 3[a] | −51 ± 5[a] | −49 ± 4[a] | −54 ± 4[a] | −49 ± 3[a] | −48 ± 1[a] | −32 ± 5[a] | −3 ± 4 |
| BFU-E | | | | | | | | | |
| IL-8 WT | −51 ± 6[a] | −48 ± 8[a] | −21 ± 6[b] | +5 ± 6 | +2 ± 7 | | | | |
| PF4 WT | −47 ± 4[a] | −48 ± 2[a] | −23 ± 17 | −2 ± 5 | −5 ± 2 | | | | |
| IL-M81 | −50 ± 1[a] | −50 ± 2[a] | −50 ± 1[a] | −46 ± 1[a] | −48 ± 2[a] | −46 ± 5[a] | −45 ± 2[a] | −14 ± 6 | −4 ± 9 |
| IL-8M8 | −49 ± 5[a] | −46 ± 8[a] | −29 ± 4[b] | −1 ± 2 | −7 ± 1 | | | | |
| IL-8M9 | −48 ± 4[a] | −48 ± 3[a] | −28 ± 2[a] | −10 ± 6 | −6 ± 3 | | | | |
| IL-8M10 | −51 ± 5[a] | −50 ± 2[a] | −47 ± 3[a] | −47 ± 7[a] | −43 ± 7[a] | −43 ± 7[a] | −38 ± 7[a] | −22 ± 5[b] | +2 ± 5 |
| CFU-GEMM | | | | | | | | | |
| IL-8 WT | −66 ± 7[a] | −64 ± 0[a] | −24 ± 2[a] | −7 ± 2 | 0 ± 0 | | | | |
| PF4 WT | −64 ± 0[a] | −62 ± 7[a] | −27 ± 9[b] | −7 ± 2 | 0 ± 0 | | | | |
| IL-8M1 | −64 ± 0[a] | −66 ± 1[a] | −66 ± 2[a] | −60 ± 2[a] | −62 ± 3[a] | −62 ± 3[a] | −55 ± 0[a] | −36 ± 0[a] | −12 ± 3 |
| IL-8M8 | −64 ± 0[a] | −64 ± 0[a] | −39 ± 7[a] | −27 ± 18 | −5 ± 5 | | | | |
| IL-8M9 | −64 ± 0[a] | −64 ± 0[a] | −32 ± 14[b] | −18 ± 18 | −6 ± 3 | | | | |
| IL-8M10 | −66 ± 2[a] | −65 ± 2[a] | −64 ± 0[a] | −63 ± 3[a] | −64 ± 0[a] | −60 ± 5[a] | −50 ± 5[a] | −30 ± 7[b] | −5 ± 5 |

79:2605–2609, 1992); and Maze et al., *J. Immunol.*, 149:1004–1009, 1992).

Briefly, the effects of chemokines upon CFU-GM were assessed by plating $1 \times 10^5$ low density (<1.077 gm/cm$^3$) normal human bone marrow cells in 0.3% agar culture medium with 10% FBS (Hyclone, Logan, Utah) with 100 U/ml recombinant human (rhu) GM-CSF plus 50 ng/ml rhu Steel factor (Immunex Corp., Seattle, Wash.). The effects of chemokines upon CFU-GEMM and BFU-E were assessed by growing the cells in 0.9% methylcellulose culture medium in the presence of recombinant human erythropoietin (rhuEpo) (1 to 2 U/ml) in combination with 50 ng/ml rhu Steel factor. Three plates were scored per concentration per experiment for CFU-GM, CFU-GEMM, and BFU-E colonies after incubation at 37° C. in lowered (5%) $O_2$ for 14 days. The combination of GM-CSF and Steel factor, or erythropoietin and Steel factor, allowed detection of large colonies (usually >1,000 cells/colony) which are derived from early, more immature subsets of CFU-GM, CFU-GEMM, and BFU-E. Levels of significance were determined using Student's t-distribution (two-tailed test). The data are presented in Table IB, with "a" denoting a significant change from control with p<0.01, and "b" denoting a significant change from control at p<0.05 (student's t test).

Figure 6H:
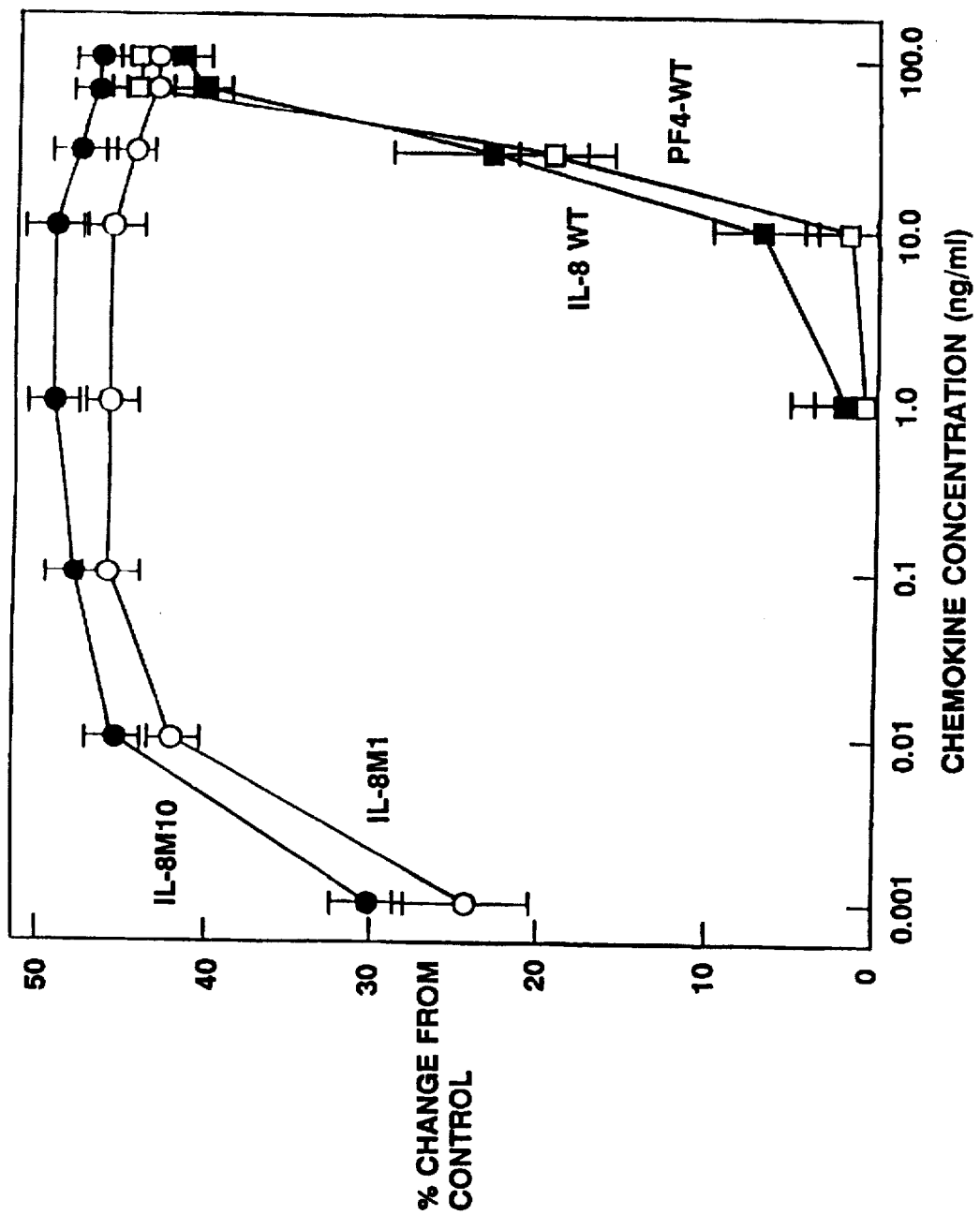

As shown in Table IB, there were no observable differences in the myelosuppressive activities of the chemokines The data in Table IB are also represented in graphical form in FIG. 6H, which shows the percent inhibition of GM colony formation by IL-8M1 and IL-8M10 compared to wild-type IL-8 (IL-8 WT) wild-type PF4 (PF4 WT).

As noted above, all of the results, taken together, show that there are two active domains within IL-8 involved in myelosuppressive activity ($E_4L_5R_6$ and $E_{24}L_{25}R_{26}V_{27}$). Moreover, the amino acid sequences DLN (IL-8M10), ELQ (IL-8M8), or DLR (IL-8M9) can also function as active domains. Likewise, PF4 also has two active domains ($D_7L_8Q_9$ and $D_{54}L_{55}Q_{56}$). Furthermore, the data obtained from PF4-426 shows that the amino acid sequence IATLKNGQK (SEQ ID NO:43) from wild-type Gro-β is responsible, in conjunction with PF4's first active domain, for the high myelosuppressive activity observed. This sequence, which is present in Gro-β, but not in Gro-α or Gro-γ, is therefore believed to contain an active domain of this protein.

In addition, the data obtained from PF4-414 shows that the amino acid sequence ACLNPASPIVK (SEQ ID NO:44) from wild-type Gro-α is responsible, in conjunction with PF4's first active domain, for a high myelosuppressive activity. Although Gro-α is itself inactive in suppressing myeloid cell proliferation, it competes with IL-8 and PF4 for progenitor cell suppression, which suggests that it is able to interact on the cell surface and block activity. Thus, it is possible that Gro-α lacks some activation sequence required for myelosuppression, but includes a sequence responsible for binding. Without the activation sequence, wild-type Gro-α has no myelosuppressive activity, but remains a competitive binding protein. However, when combined with an active domain from PF4 as described herein, the resulting new protein has very potent myelosuppressive activity. This sequence ACLNPASPIVK (SEQ ID NO:44) is therefore believed to contain an active domain of Gro-α.

New Chemokine-Like Proteins That Inhibit Myelosuppression Do Not Elicit Neutrophil Degranulation The ability of the new chemokine-like proteins to mediate neutrophil degranulation was tested in an in vitro assay as described by Hebert, et al., *J. Immunol.*, 145:3033, 1990, with some modifications. Isolated human neutrophils were suspended in PBS containing 0.02M $Na_2HPO_4$, pH 7.4, 0.15M NaCl, 0.2M Hepes, 1 mg/ml BSA, 5 mM glucose, $5 \times 10^{-3}$ mg/ml cytochalasin B (5 mg/ml stock in DMSO; Sigma) at a concentration of $2 \times 10^6$ cells/ml. 0.5 ml aliquots of the resuspended neutrophils were added to 0.5 ml of the PBS solution. Following incubation, the cells were reequilibrated at 37° C. for 15 min.

Varying concentrations of wild-type IL-8 or IL-8 polypeptide antagonist were added to the neutrophils with gentle mixing. Following addition of the IL-8 or IL-8 polypeptide antagonist, the cells were pelleted and 0.75 ml of the resulting supernatant was added to 2.25 ml PBS in the presence of $5 \times 10^{-3}$ mg/ml of the fluorescent elastase substrate MeO-Suc-Ala-Ala-Pro-Val-aminomethylcoumarin (5 mg/ml stock in DMSO; Peninsula Laboratories, Inc., Belmont, Calif.). Cleavage of the fluorescent elastase substrate releases a molecule which, upon excitation at 380 nm, emits light at a wavelength of 460 nm. The samples were incubated for 1 h at 37° C., placed on ice, and analyzed using a spectrofluorometer. Elastase levels were determined as the amount of fluorescent probe released from the elastase substrate. Uncleaved substrate displayed minimal fluorescence intensity relative to the cleaved product. Backgrounds, which were typically less than 2% of the maximum fluorescence released at the highest chemokine concentration were subtracted from each sample. The activities of compounds in this in vitro neutrophil degranulation assay are predictive of the ability of the compounds to elicit neutrophil degranulation in vivo.

Figure 7A:
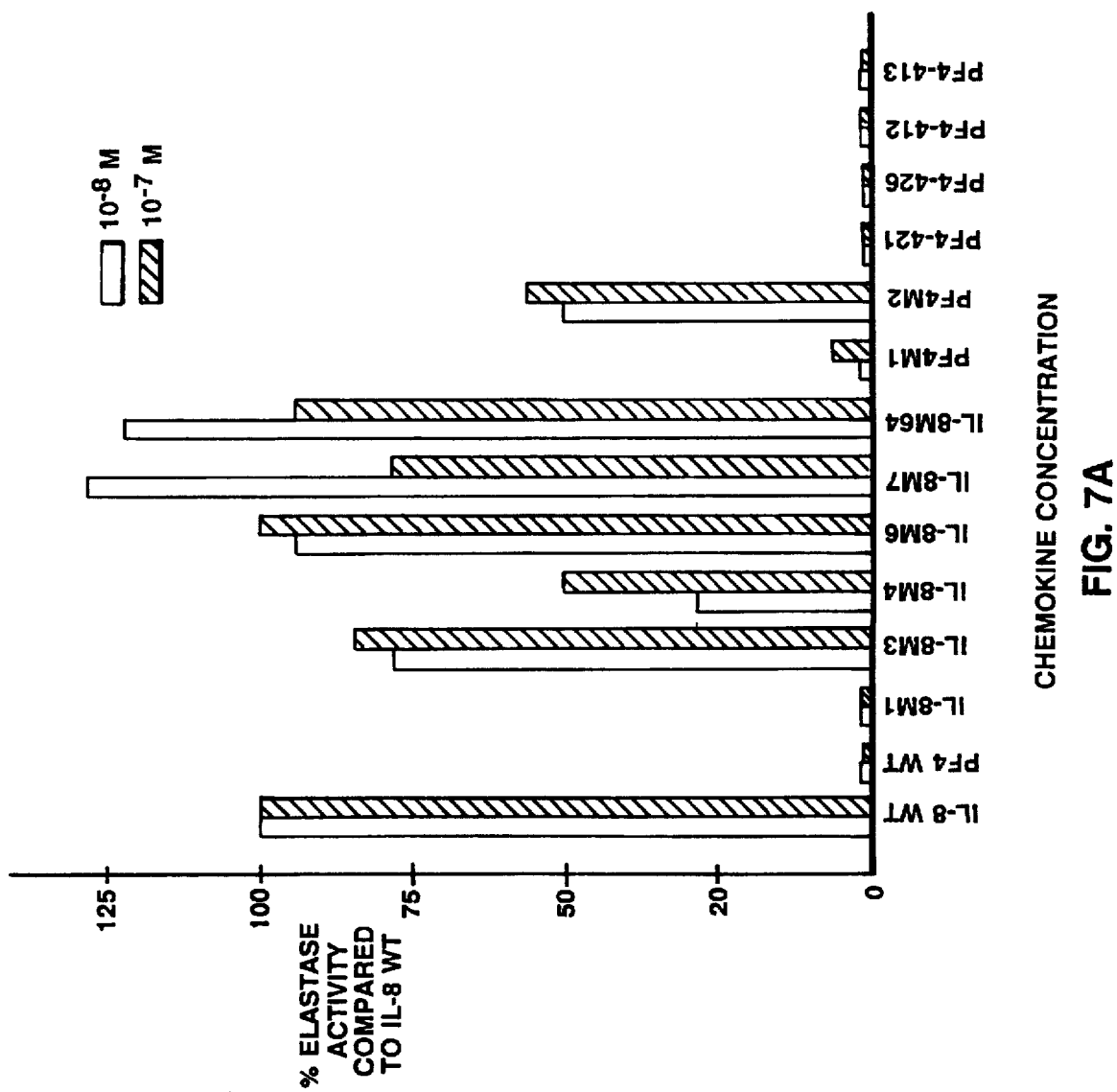
FIG. 7A is a bar graph comparing the ability of the new chemokine-like proteins to elicit neutrophil degranulation as detected by release of elastase activity from neutrophils.
Figure 7B:
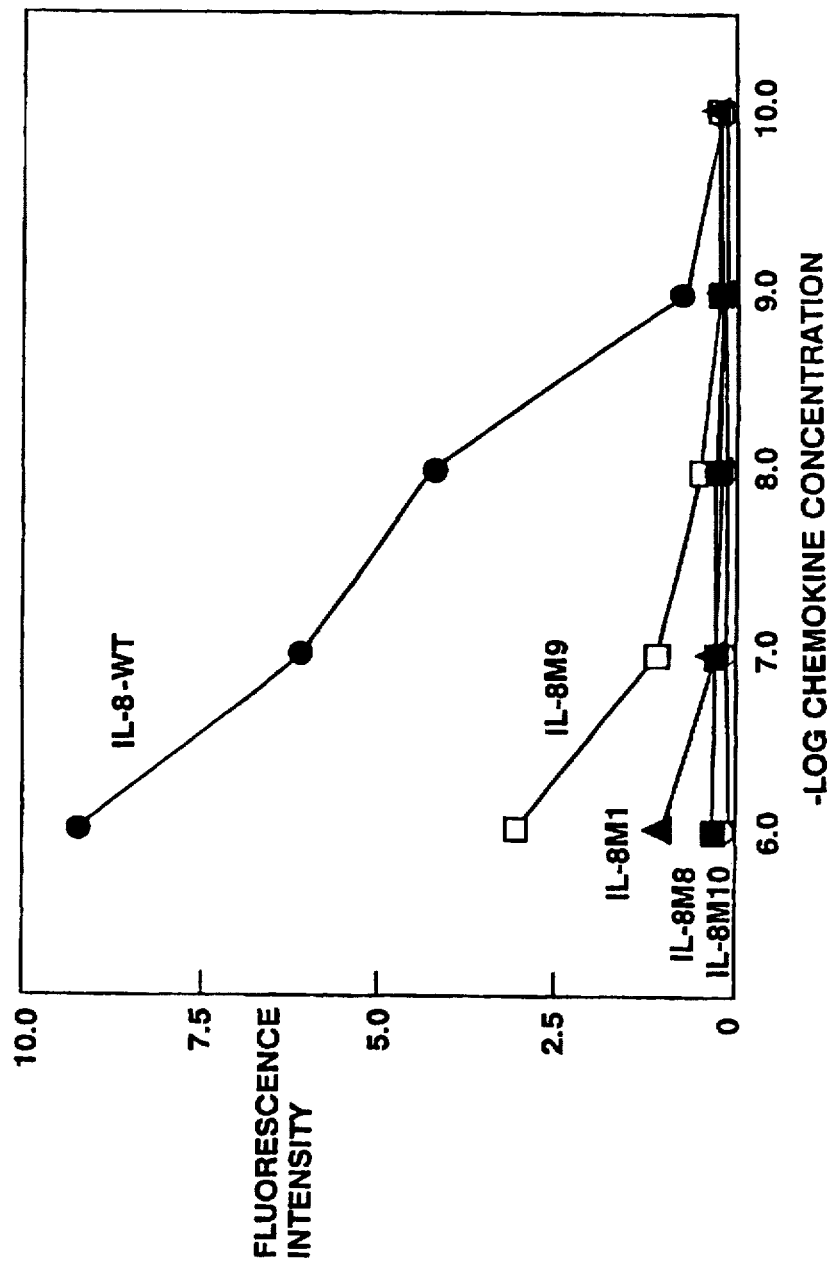
FIG. 7B is a graph comparing elastase release activity of IL-8M1, IL-8M8, IL-8M9, IL-8M10, and wild-type IL-8 in an in vitro assay.

As shown in FIG. 7A, the antagonist, IL-8M1 was significantly inhibited in its ability to activate neutrophils, which was quite surprising given this protein's potent myelosuppressive activity. Without being held to theory, the $D_7L_8Q_9$ amino acids (first active domain) from wild-type PF4 appear to make this new chemokine-like protein act as if PF4 and IL-8 were both present and acting synergistically, but with a much higher activity per total amount of protein than can be achieved by merely combining the two wild-type proteins. With the exception of PF4M2, which possesses the ELR domain of IL-8, none of the new chemokine-like proteins based on PF4, including the highly active PF4-414 and PF4-426, elicited any response on human neutrophils (FIG. 7A). New chemokine-like proteins IL-8M1, IL-8M8, IL-8M9, and IL-8M10, which are able to suppress proliferation of myeloid progenitor cells, elicited no or little neutrophil degranulation relative to wild-type IL-8 (FIG. 7B).

Since IL-8M1 and IL-8M10 are highly active at inhibiting proliferation of progenitor cells, yet do not activate neutrophils, these new chemokine-like proteins will not elicit the adverse neutrophil activation and concomitant inflammatory effects observed with wild-type IL-8.

New Chemokine-Like Proteins Inhibit Progenitor Cell Proliferation In Vivo

Wild-type PF4 and IL-8, and new chemokine-like protein IL-8M1 were also tested in an in vivo model as follows. Murine models for assessing progenitor cell proliferation were carried out substantially as described in Cooper et al., *Exp. Hematol.*, 22:186–193 (1994). The results of this in vivo model, together with the in vitro assay results described above, are predictive of the efficacy of the new proteins in treating patients, e.g., humans.

Control medium, control diluent, wild-type IL-8 and PF4, and the new chemokine-like protein IL-8M1 were evaluated for effects on myelopoiesis in vivo in mice, with endpoints being nucleated cellularity and differentials in the bone marrow, spleen, and peripheral blood, and absolute numbers and cycling status of myeloid progenitor cells in the marrow and spleen. In each test, groups of three C3H/HeJ mice or $BDF_1$ mice were exposed to a particular test sample. C3H/HeJ mice were used because they are relatively insensitive to the effects of endotoxin. Thus, any potential endotoxin contamination in the chemokine samples did not influence the in vivo results. $BDF_1$ mice were used in addition to C3H/H3J mice to make certain that the observed phenomena were not mouse strain-specific.

C3H/HeJ and $BDF_1$ mice were purchased from the Jackson Laboratory (Bar Harbor, Me.), were housed in a conventional animal facility, and were injected intravenously with 0.2 ml/mouse sterile pyrogen-free saline, or the stated amount of a specific chemokine or chemokine-like protein, as described in Mantel et al., *P.N.A.S. USA*, 90:2232 (1993). The mice were sacrificed 24 hours later.

The cycling status of hematopoietic progenitor cells, i.e., the proportion of progenitor cells in DNA synthesis (S phase of the cell cycle), was estimated as described in Maze et al., *J. Immunol.*, 149:1004 (1992) and Cooper et al., *Exp. Hematol.*, 22:186 (1994). The high specific activity (20 Ci/mM)-tritiated thymidine (50 μCi/mL) (New England Nuclear, Boston, Mass.) kill technique was used, and is based on a calculation in vitro of the reduction in the number of colonies formed after pulse exposure of cells for 20 minutes to "hot" tritiated thymidine as compared with a control such as McCoy's medium or a comparable amount of non-radioactive "cold" thymidine.

In brief, femoral bone marrow was removed from the sacrificed mice, treated with high-specific-activity tritiated thymidine, and plated in 0.3% agar culture medium with 10% FBS in the presence of 10% volume/volume pokeweed mitogen mouse spleen cell cultured medium. Colonies (>40 cells/aggregate) and clusters (3–40 cells) were scored after 7 days of incubation.

Three plates were scored for each sample for a statistical analysis. Each mouse was evaluated separately in groups of three mice each. Results for two experiments with three mice per group (each analyzed individually) are shown in Table II below, and are expressed as the mean ±1 standard deviation (SD). The results are derived from the averages of each of the individual mice within a group. The probability of significant differences between groups was determined by Student's t-test (two-tailed). Parentheses indicate the percent change from control. In the table, those data marked with a "c" represent a significant percent change from control, $p<0.005$ (Students t test), while those data marked with a "d"

represent a significant percent change from control, p<0.025, and those data marked with an "*" represent a significant percent change from control, p<0.01. All other differences are not significantly different from control, p>0.1.

Briefly, IL-8 was iodinated as previously described (Thomas et al., *J. Biol. Chem.*, 266:14839–14841, 1991), or purchased from NEN-Dupont. A stable transfectant CHO cell line, 4ABCH033 (LaRosa et al., *J. Biol. Chem.*, 267:25402–25406, 1992), expressing human neutrophil IL-8

TABLE II

Influence of IL-8, IL-8M1, and PF4 on Absolute Numbers and Cycling Status of Granulocyte
-Macrophage Progenitor Cells (CFU-GM) In Vivo in Femurs of C3H/HeJ and BDF$_1$ Mice.

| | nucleated cells/Femur × 10$^{-6}$ | | Absolute No. CFU-CM/Femur × 10$^{-3}$ | | Percent CFU-GM in Cycle | |
|---|---|---|---|---|---|---|
| | BDF$_1$ | C3H/HeJ | BDF$_1$ | C3H/HeJ | BDF$_1$ | C3H/HeJ |
| control saline | 13.3 ± 1.6 | 25.7 ± 2.5 | 9.1 ± 0.5 | 28.1 ± 3.7 | 57.0 ± 6.8 | 55.0 ± 5.1 |
| IL-8M 10 ug | 13.3 ± 1.8 | 23.2 ± 4.7 | 6.1 ± 0.8 (−33)$^e$ | 14.6 ± 1.6 (−48.1)$^e$ | 3.2 ± 6.4 (−94)$^e$ | 0.5 ± 2.9 (−99)$^e$ |
| IL-8M 1 ug | 10.0 ± 1.0 | 21.3 ± 1.4 | 7.7 ± 0.5 (−15)$^d$ | 26.3 ± 3.9 (−6.3) | 48.9 ± 3.3 (−14) | 48.5 ± 8.7 (−12) |
| IL-8M 0.01 ug | 10.7 ± 0.7 | 23.7 ± 0.4 | 8.1 ± 1.1 (−12) | 29.5 ± 2.2 (+4.8) | 49.0 ± 1.8 (−14) | 51.6 ± 5.9 (−6) |
| IL-8M1 10 ug | 11.5 ± 2.0 | 23.0 ± 3.9 | 5.1 ± 0.3 (−44)$^e$ | 16.2 ± 2.4 (−42.4)$^e$ | 0.7 ± 4.5 (−99)$^e$ | 2.2 ± 4.3 (−96)$^e$ |
| IL-8M1 1 ug | 12/9 ± 2.2 | 22.1 ± 2.4 | 5.6 ± 0.5 (−38)$^e$ | 15.6 ± 0.6 (−44.7)$^e$ | 3.5 ± 7.7 (−94)$^e$ | 2.9 ± 3.0 (−95)$^e$ |
| IL-8M1 0.01 ug | 12.3 ± 1.9 | 23.1 ± 5.4 | 6.7 ± 0.8 (−26)$^e$ | 16.9 ± 4.2 (−39.7)$^d$ | 17.7 ± 5.3 (−69)$^e$ | 14.7 ± 11.7 (−73)$^e$ |
| PF4 10 ug | 12.6 ± 1.0 | 25.0 ± 6.7 | 6.1 ± 0.3 (−33)$^e$ | 17.1 ± 4.2 (−39.3)$^d$ | 3.3 ± 5.6 (−94)$^e$ | 1.5 ± 6.1 (−97)$^e$ |
| PF4 1 ug | 12.4 ± 2.6 | 21.6 ± 1.0 | 8.8 ± 1.7 (−3) | 29.7 ± 2.4 (+5.5) | 52.0 ± 6.8 (−9) | 50.9 ± 7.6 (−8) |
| PF4 0.01 ug | 12.1 ± 1.0 | 21.8 ± 2.1 | 8.6 ± 0.4 (−5) | 26.8 ± 3.4 (−4.8) | 48.6 ± 1.9 (−15) | 50.8 ± 5.8 (−8) |

Figure 8A:
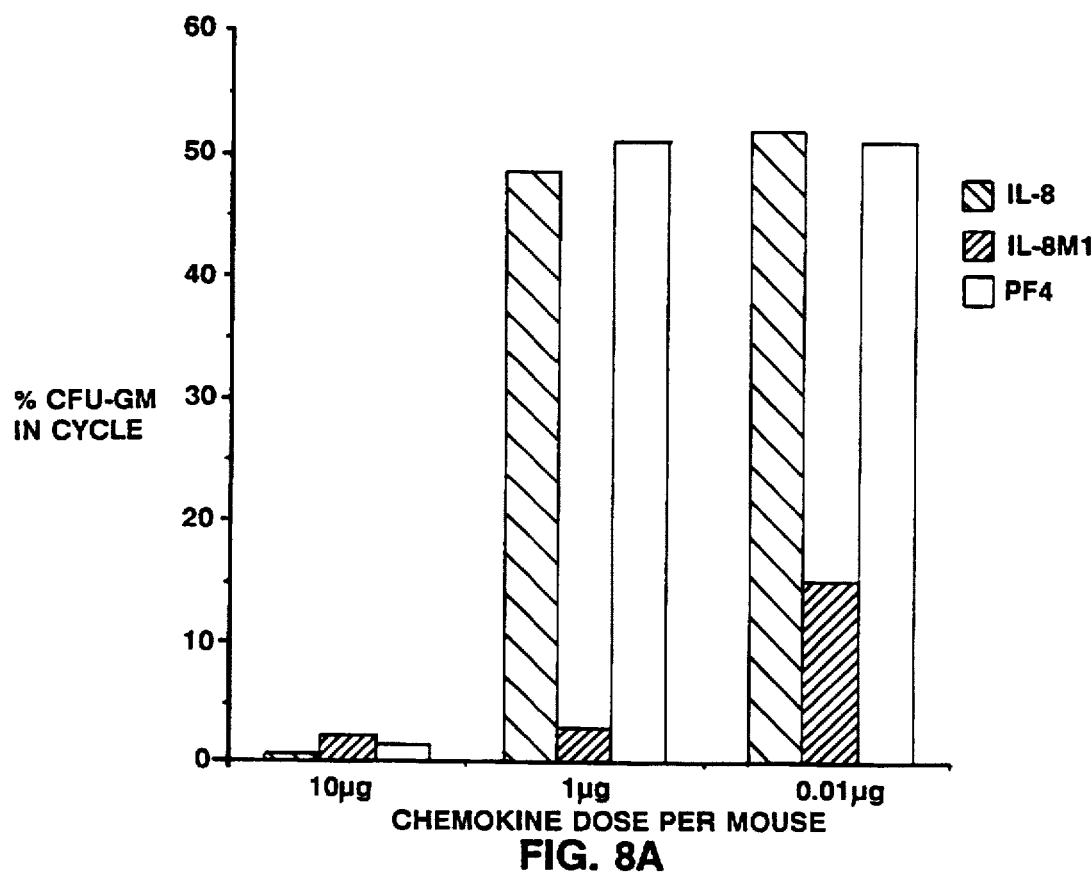
FIG. 8A is a bar graph comparing the influence of wild-type IL-8 and PF4 and new chemokine-like protein IL-8M1 on the cycling status of granulocyte-macrophage progenitor cells in vivo.
Figure 8B:
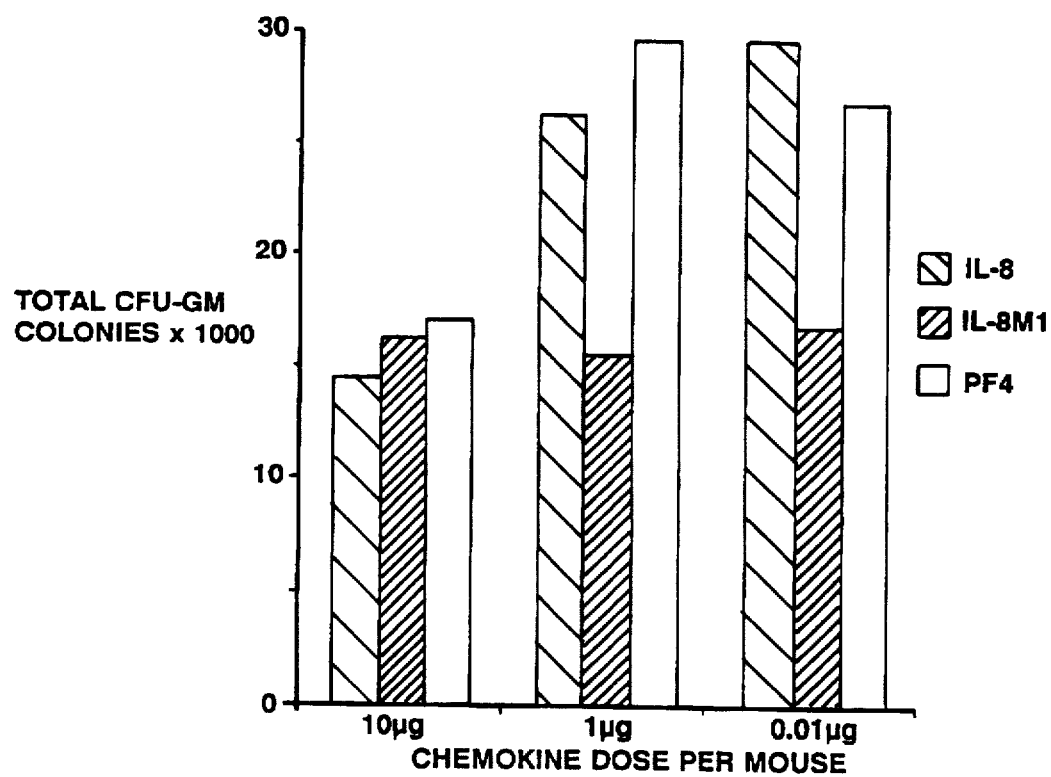
FIG. 8B is a bar graph comparing the influence of wild-type IL-8 and PF4 and new chemokine-like protein IL-8M1 on the absolute numbers of granulocyte-macrophage progenitor cells in vivo.

The in vivo results are shown in Table II above (and are represented in graphical form in FIGS. 8A and 8B). As shown, wild-type IL-8 and PF4 were effective at a dosage of 10 μg/mouse, but were not significantly effective at lower dosages of 1.0 or 0.01 μg/mouse. Similarly, cell cycling was completely inhibited at a dosage of 10 μg/mouse. As expected, these in vivo data confirmed the results of the in vitro assay described above.

The new chemokine-like protein IL-8M1, however, was effective at a dosage as low as 0.01 μg/mouse. At this dosage, progenitor cell cycling was suppressed from approximately 55% down to 14.7% +/−11.7%, for a total reduction of 73.3% compared to control. The results were similar for the two studies of absolute number of colony forming units per mouse femur (top of Table II), and the percentage of cells in the replicating cycle (bottom of Table II).

The results of the in vivo tests are also depicted in graphical form in FIGS. 8A and 8B. As shown in FIG. 8A, dosages of 1.0 and 0.01 μg of wild-type IL-8 and PF4 had little effect on the percentage of CFU-GM in cycle, which is normally about 50 to 55 percent. However, even at a dosage of 0.01 μg, new chemokine-like protein IL-8M1 reduced the percentage of cells in cycle to less than 15 percent, and to less than 5.0 percent at a dosage of 1.0 μg. IL-8M1 also reduced the percentage of cells in cycle to less than 5.0 percent at a dosage of 10.0 μg, as did wild-type IL-8 and PF4.

As shown in FIG. 8B, absolute numbers of CFU-GM progenitor cells were also affected by the presence of chemokines. Wild-type PF4 and IL-8 decreased total cell numbers only at the 10 μg doses, while IL-8M1, being the more potent agent, inhibited the proliferation of progenitor cells at doses as low as 0.01 μg/mouse. The decrease in absolute numbers of progenitor cell in vivo indicates that cell proliferation has been inhibited, and is a good correlate of the cell cycling assay described above.

Binding of New Chemokine-Like Proteins to IL-8 Receptor Subtype B In Vitro

The ability of the IL-8 derived chemokines to competitively bind IL-8 receptor subtype B in the presence of wild-type IL-8 was examined in vitro.

receptor subtype B (huIL8Rb), was used in binding assays to test mutant chemokine binding. Approximately 5×10$^3$ cells were plated in the wells of a 96 well plate and grown for 2 to 3 days. The medium was replaced with phosphate-buffered saline (PBS) supplemented with 0.5% BSA (PBS/BSA), 0.5 nM $^{125}$I-labeled IL-8, and increasing concentrations of the various unlabeled chemokines. The plates were incubated on ice for 90 minutes, the binding mixture was removed, and the cells were washed three times with ice-cold PBS/BSA. The cells were removed from the plates with trypsin-EDTA (Gibco), and the radioactivity of the entire contents of the well determined by gamma counting. Binding of each chemokine to untransfected cells, or binding in the presence of 2 μM unlabeled IL-8, was determined and the value obtained used as the background value. Binding data was plotted as percent of mean specific binding (total binding minus background/specific binding with no competitor). The Ki (the chemokine concentration to inhibit 50% of $^{125}$I-labeled wild-type IL-8 binding) for each chemokine was calculated and is presented in Table III. "NC" indicates no competition.

TABLE III

| Chemokine | Ki (nM) |
|---|---|
| IL-8 | 3.0 ± 0.5 |
| IL-8M1 | 661.0 ± 189 |
| IL-8M3 | 22.1 ± 4.4 |
| IL-8M4 | 29.3 ± 7.2 |
| IL-8M64 | 35.3 ± 6.2 |
| PF4 | NC |
| PF4M1 | 839.4 ± 202 |
| PF4M2 | 52.0 ± 11.8 |

Wild-type IL-8, as well as other "ELR"-containing chemokines including Gro-α, Gro-β, and NAP-2, bound the IL-8 subtype B receptor with high affinity. As shown in Table III, competition binding experiments utilizing $^{125}$I-labeled IL-8 and unlabeled mutant chemokine competitors demonstrated that the IL-8 receptor subtype B binding and myelosuppressive activity are not correlated. For example, IL-8M1 and PF4-M2 have comparable myelosuppressive activity, yet neither chemokine effectively competes with wild-type IL-8 for IL-8 receptor subtype B binding. Moreover, the chemokines that most effectively competed with wild-type IL-8 for IL-8 receptor subtype B binding exhibited the lowest levels of myelosuppressive activity (e.g., IL-8M3, IL-8M4, and IL-8M64). These data suggest that myelosuppression is not mediated by chemokine binding to the IL-8 receptor subtype B.

Heparin Binding by PF4 and PF4-based Chemokines

In addition to its myelosuppressive activities, wild-type PF4 is characterized by high affinity binding and neutralization of heparin. Wild-type PF4 binds heparin with a binding constant between $3 \times 10^{-8}$ and $1 \times 10^{-7}$M. The heparin binding affinity for the PF4-derived chemokines was determined according to methods well known in the art. The PF4-derived chemokines bound heparin with a dissociation constants approximating $1 \times 10^{-7}$M, suggesting that the mutant proteins, including PF4-426, had properly refolded and bound heparin in a manner analogous to wild-type PF4. All of the IL-8 related proteins, including wild-type IL-8, bound heparin at levels at least 20-fold lower than PF4, suggesting that the IL-8-derived chemokines were also folded in the proper conformation.

Examination of Chemokine-like Competitors of Myelosuppression

Chemokine-like proteins that were inactive in the progenitor proliferation assays above were tested for their ability to inhibit the myelosuppressive activity of either IL-8 or PF4. Varying concentrations of chemokine mutants IL-8M3, IL-8M4, IL-8M6, and PF4-412 were incubated with either 50 ng/ml wild-type PF4 or 50 ng/ml wild-type IL-8 in the CFU-GM assay described above. Cells were plated in 0.3% agar culture medium with 10% v/v fetal bovine serum, 100 U/ml rhu GM-CSF, and 50 ng/ml rhu steel factor. The results of these experiments, as mean ±1 standard error of the mean (SEM) with percent change from control shown in parenthesis, are shown in Table IV. These results are one of two similar and reproducible experiments. "$^b$" indicates significant change from control at $p<0.001$; "$^c$" indicates significant change from control at $p<0.05$.

IL-8M3 did not exhibit suppression of progenitor cell proliferation at any concentration tested. However, at 250 ng/ml and 500 ng/ml, IL-8M3 blocked the myelosuppressive activity of wild-type IL-8. Under identical conditions, this mutant was unable to inhibit the ability of PF4 to suppress progenitor proliferation. Thus, IL-8M3 can enhance progenitor cell proliferation by inhibiting IL-8 mediated myelosuppression.

IL-8M3 inhibition of IL-8-mediated myelosuppression also suggests that this mutant interacts with a cell-based receptor. The data from the receptor binding studies above, which indicate that IL-8M3 competes with wild-type for IL-8 receptor subtype B binding, suggests that IL-8M3 mediates its anti-myelosuppressive activity by binding this receptor, or a similar, IL-8 subtype B-like receptor. In addition, the inability of IL-8M3 to inhibit PF4-mediated myelosuppression suggests that several different progenitor cell receptors, with different specificities, facilitate progenitor cell myelosuppression.

Uses of New Chemokine-Like Proteins

The new chemokine-like proteins can be used both as diagnostic and therapeutic agents.

Diagnostic Uses

The subclass of progenitor cells that respond to the presence of chemokines has been shown to include a cell population which contains the cell surface marker CD34. Therefore, the new chemokine-like proteins can be used as diagnostic agents to identify CD34$^+$ progenitor cells in a sample population. For example, a solid substrate or matrix coated with a new chemokine-like protein can be used to separate out cells that are responsive to the protein from a sample of cells removed from a patient. After culturing or expansion of these CD34$^+$ cells ex vivo, these cells can be re-introduced into the patient following transplant, chemotherapy, or radiation therapy.

Furthermore, the new chemokine-like proteins can be used as diagnostic screening agents to identify patients with hyperproliferative diseases who would be responsive to therapy with the new chemokine-like proteins. For example, an in vitro assay, e.g., as described above, is used to test whether a particular new chemokine-like protein suppresses the proliferation of myeloid cells, e.g., leukemic cells, in a sample taken from a patient. A positive result, e.g., an inhibition of proliferation of 50 percent compared to a

TABLE IV

| Sample | Concentration | Chemokine alone | | Wild-type IL-8 | | Wild type PF4 | |
|---|---|---|---|---|---|---|---|
| control medium | | 62 ± 1 | | 31 ± 4 | (−50)$^b$ | 32 ± 3 | (−48)$^b$ |
| IL-8M3 | 500 | 60 ± 3 | (−3) | 60 ± 5 | (−3) | 33 ± 1 | (−47)$^b$ |
| IL-8M3 | 250 | 58 ± 2 | (−3) | 63 ± 2 | (+2) | 28 ± 2 | (−55)$^b$ |
| IL-8M3 | 50 | 62 ± 4 | (0) | 26 ± 1 | (−58)$^b$ | 26 ± 2 | (−58)$^b$ |
| IL-8M4 | 500 | 61 ± 2 | (−2) | 33 ± 2 | (−47)$^b$ | 29 ± 3 | (−53)$^b$ |
| IL-8M4 | 250 | 61 ± 1 | (−2) | 34 ± 1 | (−45)$^b$ | 29 ± 2 | (−53)$^b$ |
| IL-8M6 | 500 | 32 ± 4 | (−48)$^b$ | | | | |
| IL-8M6 | 250 | 47 ± 4 | (−24)$^c$ | | | | |
| IL-8M6 | 50 | 61 ± 2 | (−2) | | | | |
| PF4 | 500 | 57 ± 3 | (−8) | 27 ± 2 | (−56)$^b$ | 27 ± 2 (−56)$^b$ | |

Mutants IL-8M4 and PF4-412 had no effect either as suppressors of progenitor proliferation, or as competitors with either wild-type IL-8 or wild-type PF4. IL-8M6 suppressed progenitor cell proliferation at the highest concentration tested (500 ng/ml), thus demonstrating its activity as a weak agonist in this system.

control, indicates that the patient can be treated using the new protein as a therapeutic agent to suppress the proliferation of myeloid leukemias.

Therapeutic Uses

The new chemokine-like proteins of the invention can be administered to a patient as adjunctive agents before and/or during chemotherapy or radiation therapy to protect myeloid progenitor cells from the cytotoxic effects of the chemotherapeutic agents or radiation. The new proteins place myeloid cells into a myeloprotected, slow-cycling state, thereby inhibiting or decreasing cell damage that could otherwise be caused by cell-cycle active chemotherapy drugs such as cytosine arabinoside, 5-fluorouracil, or hydroxyurea. The use of the new proteins also permits the administration of higher doses of chemotherapeutics without compromising the ability of the patient to generate mature functional blood cells. The new chemokines can be used to protect progenitor cells in either an in vivo or in vitro setting.

The new protein IL-8M3 can be administered to a patient to enhance progenitor cell proliferation by inhibition of the myelosuppressive activity of wild-type IL-8, or IL-8-based chemokines having myelosuppressive activity (e.g., IL-8M1 and IL-8M10). IL-8M3, or other chemokines that negatively regulate chemokine-mediated myelosuppression, can be administered to patients in whom myeloid cell proliferation is desirable, e.g., in patients having abnormally low numbers of cells derived from myeloid progenitors as a result of disease, e.g., leukemia or HIV infection, or as a side-effect of a therapeutic regimen such as chemotherapy.

The new chemokine-like proteins are administered to a patient in the same way as normal, wild-type chemokines are administered, e.g., they are injected intravenously or subcutaneously in a pharmaceutically acceptable carrier. For example, sterile saline or 30% acetonitrile/0.1% trifluoroacetic acid (ACN), as suggested for MIP-1α in Cooper et al. supra, can be used as a carrier.

As described above, in vivo murine studies with IL-8M1 have shown that effective suppression of progenitor cell proliferation occurs at dosages of approximately 10.0 to 0.01 µg per animal, although 1.0 to 0.01 µg per animal is preferred. This translates into a dosage of approximately 0.5 to 500 µg/kg. Assuming the average human patient weighs 70 kgs, the effective amount for a human would be approximately 0.035 to 35.0 mg. Thus, a suitable dosage for therapy in a human patient is in the range of about 0.035 to 35.0 mg, with a preferred range of about 0.5 to 5 mg.

Note that in chemotherapy, specific protocols vary, and factors such as tumor size, growth rate, and location of the tumor all affect the course of adjunctive therapy with the new proteins. Administration of chemotherapeutic agents, as well as the new chemokine-like proteins, requires knowledge of the extent of disease, the toxicity of previous treatment courses, and the timing of the expected drug toxicity.

The new chemokine-like proteins also can be used to inhibit hyperproliferative myeloid-based diseases such as chronic myelogenous leukemia, polycythemia vera, and hypermegakaryocytopoietic disorders. Hyperproliferative states in such disorders occur because the progenitor cells are unable to negatively regulate cell growth and replication. Administration of the new chemokine-like proteins is expected to inhibit cell replication resulting in the inhibition of the abnormal cell growth. This expected effect is based on indications that certain populations of myeloid leukemia cells are responsive to the inhibitory effects of wild-type chemokines. Dosages of chemokine-like proteins for treating hyperproliferative myeloid based diseases would be similar to those dosages described above for use of the proteins as adjuncts to chemotherapy.

In addition, the new chemokine-like proteins can be used to prevent myeloid progenitor cells from becoming leukemic as the result of the administration of chemotherapeutic agents. The chemokine-like proteins are administered in the same way described above.

The new chemokine-like proteins also can be used in a method of isolating progenitor cells for, for example, bone marrow transplantation. Bone marrow transplants require collection of a large number of progenitor cells. Because progenitor cells are normally present in peripheral blood in very low numbers, isolation of a sufficient number of cells normally requires a bone marrow tap. The new chemokine-like proteins can be administered to the patient intravenously to mobilize progenitor cells from the bone marrow to the peripheral blood, thus providing a sufficient number of progenitor cells in the peripheral blood and avoiding the need for a bone marrow tap. While intravenous administration of wild-type IL-8 also results in progenitor cell mobilization, wild-type IL-8 also elicits neutrophil degranulation. The new chemokine-like proteins are advantageous for this use because they can elicit progenitor cell mobilization without eliciting neutrophil activation.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated protein having the amino acid sequence of a wild-type interleukin-8 (IL-8) having four cysteine residues and the amino acid sequence ELR on the N-terminus side of and proximal to the first cysteine residue, with the amino acid sequence DLN substituted for said amino acid sequence ELR as the 3 contiguous amino acids on the N-terminus side of and proximal to the first cysteine residue of the wild-type IL-8 chemokine.

2. A protein of claim 1 having the amino acid sequence SAKDLNCQCIKTYSKPFHPKFIKEL-RVIESGPHCANTEIIVKLSDGRELCLDP-KENWVQRVVEKFLKRAENS (SEQ ID NO: 49).

3. An isolated protein having the amino acid sequence of a wild-type interleukin-8 (IL-8) having four cysteine residues and the amino acid sequence ELR on the N-terminus side of and proximal to the first cysteine residue, with the amino acid sequence ELQ substituted for said amino acid sequence ELR as the 3 contiguous amino acids on the N-terminus side of and proximal to the first cysteine residue of the wild-type IL-8 chemokine.

4. A protein of claim 3 having the amino acid sequence SAKELQCQCIKTYSKPFHPKFIKELRV ESGPH-CANTEIIVKLSDGRELCLDPKEN-WVQRVVEKFLKRAENS (SEQ ID NO: 47).

5. An isolated protein having the amino acid sequence of a wild-type interleukin-8 (IL-8) having four cysteine residues and the amino acid sequence ELR on the N-terminus side of and proximal to the first cysteine residue, with the amino acid sequence DLR substituted for said amino acid sequence ELR as the 3 contiguous amino acids on the N-terminus side of and proximal to the first cysteine residue of the wild-type IL-8 chemokine.

6. A protein of claim 5 having the amino acid sequence SAKDLRCQCIKTYSKPFHPKFIKEL-RVIESGPHCANTEIIVKLSDGRELCLDP-KENWVQRVVEKFLKRAENS (SEQ ID NO: 48).

7. An isolated protein having the amino acid sequence of a wild-type interleukin-8 or platelet factor 4 (PF4) having four cysteine residues, with the following modifications:

a) amino acids ELR as the 3 contiguous amino acids on the N-terminus side of and proximal to the first cysteine residue of the wild-type chemokine; and b) amino acids LDLQ as the 4 amino acids on the C-terminus side of and proximal to the fourth cysteine of the wild-type chemokine.

8. A protein of claim 7 having the amino acid sequence SAKELRCQCVKTTSQVRPRHITSLE-VIKAGPHCPTAQLIATLKNGRKICLD-LQAPLYKKIIKKLLES (SEQ ID NO:22).

9. An isolated protein having the amino acid sequence of a wild-type platelet factor 4 (PF4) having four cysteine residues, with amino acids ACLNPASPIVK (SEQ ID NO:44) replacing 11 amino acids including the fourth cysteine of the wild-type chemokine, wherein the C in ACLN-PASPIVK corresponds to the fourth cysteine residue.

10. A protein of claim 9 having the amino acid sequence EAEEDGDLQCLCVKTTSQVRPRHITSLE-VIKAGPHCPTAQLIATLKNGRKACLN-PASPIVKKIIKKLLES (SEQ ID NO:26).

11. An isolated protein having the amino acid sequence of a wild-type platelet factor 4 (PF4) having four cysteine residues, with amino acids IATLKNGQK (SEQ ID NO:43) and Z as the 10 amino acids on the N-terminus side of and proximal to the fourth cysteine of the wild-type chemokine, wherein Z is any amino acid.

12. A protein having the amino acid sequence EAEEDGDLQCLCVKTTSQVQPQHITSLE-VIKAGPHCPTAQLIATLKNGQKICLDLQAPLY KKI-IKKLLES (SEQ ID NO:28).

13. A method of suppressing proliferation of an actively dividing myeloid cell comprising contacting said cell with an effective amount of a protein of any one of claims 1, 3, 5, 7, 9, and 11.

14. An adjunctive method for use with chemotherapy or radiation therapy in a patient comprising administering a protein of any one of claims 1, 3, 5, 7, 9, and 11 to the patient, in an amount effective to suppress proliferation of actively dividing myeloid cells and administering chemotherapy or radiation therapy to the patient in conjunction with said administration of said protein.

15. A method of treating a hyperproliferative myeloid disease in a patient comprising administering to the patient a protein of any one of claims 1, 3, 5, 7, 9, and 11 in an amount effective to suppress proliferation of actively dividing myeloid cells.

16. A method of claim 15, wherein said disease is chronic myelogenous leukemia, polycythemia vera, or a hypermegakaryocytopoietic disorder.

17. A protein having the amino acid sequence SAKELRCQCIKTYSKPFHPKFIKEYRRIESGPHCANTEIIVKLSDGRELCLDPKENWVQR VVEKFL (SEQ ID NO:17).

18. A method of enhancing myeloid cell proliferation by inhibition of IL-8 mediated myelosuppression comprising contacting said cell with an effective amount of a protein of claim 17.

19. An isolated protein having the amino acid sequence of a wild-type interleukin-8 (IL-8) or platelet factor 4 (PF4) having four cysteine residues, the amino acid sequence comprising a heterologous active domain selected from the group consisting of: ELR, DLN, ELQ, DLR, ELRV, DLQ, IATLKNGQK (SEQ ID NO:43), and ACLNPASPIVK (SEQ ID NO:44).

* * * * *